US012584111B2

(12) United States Patent
Deng et al.

(10) Patent No.: US 12,584,111 B2
(45) Date of Patent: Mar. 24, 2026

(54) COMPOSITIONS AND METHODS FOR LONG TERM CULTURE OF HEPATOCYTES

(71) Applicant: Peking University, Beijing (CN)

(72) Inventors: Hongkui Deng, Beijing (CN); Chengang Xiang, Beijing (CN); Yuanyuan Du, Beijing (CN)

(73) Assignee: Peking University, Beijing (CN)

( * ) Notice: Subject to any disclaimer, the term of this patent is extended or adjusted under 35 U.S.C. 154(b) by 1073 days.

(21) Appl. No.: 17/434,284

(22) PCT Filed: Feb. 26, 2019

(86) PCT No.: PCT/CN2019/076151
§ 371 (c)(1),
(2) Date: Aug. 26, 2021

(87) PCT Pub. No.: WO2020/172792
PCT Pub. Date: Sep. 3, 2020

(65) Prior Publication Data

US 2022/0135941 A1 May 5, 2022

(51) Int. Cl.
*C12N 5/071* (2010.01)
*C12N 7/00* (2006.01)

(52) U.S. Cl.
CPC ............... *C12N 5/067* (2013.01); *C12N 7/00* (2013.01); *C12N 2501/15* (2013.01); *C12N 2501/155* (2013.01); *C12N 2501/415* (2013.01); *C12N 2501/42* (2013.01); *C12N 2501/70* (2013.01); *C12N 2502/70* (2013.01); *C12N 2730/10131* (2013.01)

(58) Field of Classification Search
CPC ................ C12N 5/067; C12N 2501/15; C12N 2501/155; C12N 2501/415; C12N 2501/42
See application file for complete search history.

(56) References Cited

U.S. PATENT DOCUMENTS

| | | | |
|---|---|---|---|
| 2016/0152950 A1 | 6/2016 | Zhang | |
| 2017/0198254 A1 | 7/2017 | Zhang | |

FOREIGN PATENT DOCUMENTS

| | | | |
|---|---|---|---|
| CN | 103374546 | 10/2013 | |
| CN | 105121632 | 12/2015 | |
| CN | 105154386 | 12/2015 | |
| JP | 2018013302 | 1/2018 | |
| WO | 2014124527 | 8/2014 | |
| WO | 2017048193 | 3/2017 | |
| WO | WO-2017048193 A1 * | 3/2017 | .......... C12N 5/0606 |
| WO | 2017220586 | 12/2017 | |
| WO | 2018218480 | 12/2018 | |

OTHER PUBLICATIONS

Pettinato, et al., Scientific Reports (2016) 6: 1-17 (Year: 2016).*
Do, et al., Am J Physiol Gastroinest Liver Physiol (2012) 303: G1220-G1227 (Year: 2012).*
Katsuda et al., (2017) Cell Stem Cell 20(1):41-55 (Year: 2017).*
Kimura, et al., European Journal of Pharmacology (1997) 327: 87-95 (Year: 1997).*
Cicchini et al., Liver International (2015) P302-310 (Year: 2015).*
Chen et al., Laboratory Investigation (2012) 92: 676-687 (Year: 2012).*
Xie, et al., Am J Physiol Gastrointest Liver Physiol (2013) 305: G881-G890 (Year: 2013).*
Zhang, et al., Am J Physiol Renal Physiol (2006) 291: F1323-F1331 (Year: 2006).*
Baranczewski, et al., "Introduction to in vitro estimation of metabolic stability and drug interactions of new chemical entities in drug discovery and development", Pharm. Rep., 58(4):453-472 (2006).
Donato, et al., "Cell lines: a tool for in vitro drug metabolism studies", Current Drug Metabolis, 9(1): 1-11 (2008).
Gao, et al., "Distinct Gene Expression and Epigenetic Signatures in Hepatocyte-like Cells Produced by Different Strategies from the Same Donor", Stem Cell Reports, 9(6):1813-1824 (2017).
Gordillo, et al., "Orchestrating liver development", Development, 142:2094-2108 (2015).
Haenseler et al., "A Highly Efficient Human Pluripotent Stem Cell Microglia Model Displays a Neuronal-Co-culture-Specific Expression Profile and Inflammatory Response", Stem Cell Reports, 8(6):1727-1742 (2017).
Hrvatin, et al., "Differentiated human stem cells resemble fetal, not adult, β cells", Proc Natl Acad Sci USA, 111(8):3038-3043 (2014).
International Search Report for PCT/CN2019/076151 dated Dec. 2, 2019.
Kyffin, et al., "Impact of cell types and culture methods on the functionality of in vitro liver systems—A review of cell systems for hepatotoxicity assessment", Toxicol. In vitro. An Int, J Published in assoc with BBIBRA, 48:262-275 (2018).
Liang, et al., "Present and future therapies of hepatitis B: From discovery to cure", Hepatology 62(6):1893-1908 (2015).
Louch, et al., "Methods in cardiomyocyte isolation, culture, and gene transfer", J Mal Cell Cardiol., 51:288-298 (2011).
Lu, et al., "Study of the early steps of the Hepatitis B Virus life cycle", International journal of medical sciences, 1(1):21-33 (2004).
Lucifora, et al., "Specific and nonhepatotoxic degradation of nuclear hepatitis B virus cccDNA", Science, 343(6176):1221-28 (2014).
(Continued)

*Primary Examiner* — Evelyn Y Pyla
*Assistant Examiner* — Katherine R Small
(74) *Attorney, Agent, or Firm* — Pabst Patent Group LLP

(57) ABSTRACT

Provided are compositions for long-term maintenance of functional hepatocytes in culture, a method for improved maintenance of functional hepatocytes in vitro, and functional hepatocytes cultures according to the methods. The culture compositions include at least: one activator of adenylate cyclase, one TGFβinhibitor, one Notch inhibitor, one Wnt inhibitor, and/or one BMP inhibitor. The combinations of compounds are added to any hepatocyte cell culture medium in an effective amount to maintain functional hepatocyte function in vitro, long term. The hepatocytes can be used for in vitro drug research and to model liver disease.

17 Claims, 49 Drawing Sheets

Specification includes a Sequence Listing.

(56) References Cited

OTHER PUBLICATIONS

Office Action CN (China) Application No. 2019/0092053.1 dated Feb. 25, 2022.
Ootani, et al., "Sustained in vitro intestinal epithelial culture within a Wnt-dependent stem cell niche", Nat Med., 15:701-706 (2009).
Shulman, et al., "Long-term culture and coculture of primary rat and human hepatocytes", Methods Mal Biol., 945:287-302 (2013).
Terry, et al., "Cryopreservation-induced nonattachment of human hepatocytes: role of adhesion molecules", Mol. Cell Transplantation, 16(6):639-647 (2017).
Winer, et al., "Long-term hepatitis B infection in a scalable hepatic co-culture system", Nat Comm., 8:125 (2017).
Xia, et al. "Human stem cell-derived hepatocytes as a model for hepatitis B virus infection, spreading and virus-host interactions", J Hepatol., 66(3): 494-503 (2017).
Yan, et al., "Sodium taurocholate cotransporting polypeptide is a functional receptor for human hepatitis B and D virus", eLife, (2012).
Zhao, et al., "Promotion of the efficient metabolic maturation of human pluripotent stem cell-derived hepatocytes by correcting specification defects", Cell Res., 23:157-161 (2013).
Extended European Search Report for application No. 19917487.1-1118/3931305 dated Oct. 6, 2022.
Office Action JP (Japan) Application No. 2021-549702 dated Oct. 31, 2022.
Peng, et al., "Inflammatory Cytokine TNFa Promotes the Long-Term Expansion of Primary Hepatocytes in 3D Culture", Cell, 175:1607-1619 (2018).
Roth, et al., "A comprehensive model for assessment of liver stage therapies targeting Plasmodium vivax and Plasmodium falciparum", Nat. Com., 9(1837):1-16 (2018).
Dunn, et al., "Long-term in vitro function of adult hepatocytes in a collagen sandwich configuration", Biotechnol. Frog., 7(3):237-245 (1991).
Elaut, et al., "Molecular mechanisms underlying the dedifferentiation process of isolated hepatocytes and their cultures", Curr Drug Metab, 7(6):629-660 (2006).
Lee, et al., "Isolation of Human Hepatocytes by a Two-step Collagenase Perfusion Procedure", J Vis Exp, 79:e50615 (2013).
Takayama, et al., "Generation of human pluripotent stem cell-derived hepatocyte-like cells for drug toxicity screening", Drug Metab Pharmacokinet., 32(1): 12-20 (2017).
Zhong, et al., "Quantitation of HBV covalently closed circular DNA in micro formalin fixed paraffin-embedded liver tissue using rolling circle amplification in combination with real-time PCR", Clin. Chim. Acta., 412(21-22):1905-1911 (2011).
English Machine Translation of Second Office Action CN (China) dated May 26, 2023.

* cited by examiner

COMPOSITIONS AND METHODS FOR LONG TERM CULTURE OF HEPATOCYTES

CROSS-REFERENCE TO RELATED APPLICATION

This application is a National Phase application under 35 U.S.C. § 371 of PCT/CN2019/076151, filed Feb. 26, 2019, the disclosure of which is hereby incorporated herein by reference in its entirety.

REFERENCE TO SEQUENCE LISTING

The Sequence Listing submitted as a text file named "PKU_102_371_ST26.txt" created on Jan. 28, 2025, and having a size of 14,309 bytes is hereby incorporated by reference.

FIELD OF THE INVENTION

The present invention generally relates to long-term maintenance of hepatocytes and functional maturation of hepatocytes.

BACKGROUND OF THE INVENTION

Terminally differentiated cells are functionally stable in vivo, a state that is highly dependent on precise spatiotemporal regulation by microenvironmental signals. Once isolated, cells undergo microenvironmental changes resulting in functional retrogression. The long-term maintenance of terminally differentiated cells in vitro has proven challenging. Once isolated, these cells commonly lose their specific functions (Haenseler et al., *Stem Cell Reports* 8, 1727-1742 (2017); Louch, et al., *J Mol Cell Cardiol* 51, 288-298 (2011); Ootani et al., *Nat Med* 15, 701-706 (2009); Shulman, et al., *Methods Mol Biol* 945, 287-302 (2013). In particular, the failure to maintain primary human hepatocytes (PHHs) long-term limits their application in modeling hepatotropic infection, such as HBV infection, a globally prevalent disease (Zhong, et al., *Clin. Chim. Acta:* 412:1905-1911 (2011)). Advances, such as the identification of the Na+-taurocholate co-transporting peptide (NTCP), a functional receptor of Hepatitis B virus (HBV), has allowed the establishment of hepatoma cell lines to study HBV infection (Yan, et al., *eLife* 1, (2012)). However, studies to investigate the HBV life cycle over time, especially the persistence of cccDNA, remain challenging (Liang et al., *Hepatology* 62, 1893-1908 (2015)). Although PHHs have been considered ideal for HBV modeling, sharing highly similar infection characteristics with de novo human HBV infection, their long-term utility is restricted by limited viability and unstable functional maintenance in vitro (Lu, et al., *International journal of medical sciences* 1, 21-33 (2004); Xia et al., *J Hepatol* 66, 494-503 (2017); Elaut et al., *Curr Drug Metab* 7, 629-660 (2006)). Therefore, the establishment of culture conditions for functional maintenance of authentic human hepatocytes may benefit HBV studies.

Furthermore, the lack of efficient culture conditions for stabilizing the function of terminally differentiated cells also limited the generation of functional mature cells from human pluripotent stem cells (hPSCs) differentiation and direct lineage reprogramming. Although hPSCs are considered an ideal potential cell source for generating a large amount of various human cell types, most hPSC-derived cells presented immature phenotypes when generated by current protocols (Hrvatin, et al., *Proc Natl Acad Sci USA.*

111 (8) 3038-3043 (2014) Takayama, et al., *Drug Metab Pharmacokinet* 32 (1): 12-20 (2017)). One major reason for the functional immaturity of hPSC-derived cells is the lack of available culture conditions, allowing them to capture the final differentiation stage. Therefore, identification of a culture condition supporting functional maintenance of terminally differentiated cells could benefit both their in vitro applications and their generation.

There remains a need for cell culture methods that provide a solution to the long-term, functional maintenance of differentiated cell types, including human hepatocytes.

It is an object of the present invention to provide methods for long-term in vitro culture of functional differentiated cells.

It is also an object of the present invention to provide compositions to maintaining functional differentiated cells in vitro, long term.

It is also an object of the present invention to provide differentiated cells with improved maintenance of function in vitro.

SUMMARY OF THE INVENTION

Compositions for long-term maintenance of functional hepatocytes in culture, a method for improved maintenance of functional hepatocytes in vitro, and functional hepatocytes cultures according to the methods disclosed herein, are provided.

The compositions include at least: an activator of adenylate cyclase, a TGFβ inhibitor, a Notch inhibitor, a Wnt inhibitor, and/or a BMP inhibitor. In some preferred embodiments, the composition includes a combination of an activator of adenylate cyclase, and TGFβ inhibitor. In a particularly preferred embodiment, the composition includes a combination of at least one activator of adenylate cyclase, one TGFβ inhibitor, one Notch inhibitor, one Wnt inhibitor, and one BMP inhibitor (herein, "5C"). A most preferred activator of adenylate cyclase activator is forskolin (FSK); a preferred TGFβ inhibitor is SB431542 (SB43); a preferred Notch inhibitor is DAPT; a preferred Wnt inhibitor is IWP 2 and a preferred BMP inhibitor is LDN193189 (LDN). The combinations of compounds are added to any hepatocyte cell culture medium in an effective amount to maintain functional hepatocyte function in vitro, long term.

The composition is used to improve maintenance of functional hepatocytes in vitro.

Also provided are hepatocytes obtained according to the methods disclosed herein ("herein, 5C hepatocytes"). The hepatocytes show improved maintenance of hepatocyte function in vitro, when cultured according to the methods disclosed herein. In a preferred embodiment, the 5C hepatocytes express at least six hepatocyte functional proteins following at least 60 days in culture, at the same levels as freshly isolated primary hepatocytes from the same organism. In a particularly preferred embodiment, 5C hepatocytes express at least six hepatocyte functional proteins following at least 90 days in culture, at the same levels as freshly isolated primary hepatocytes from the same organism. In a particularly preferred embodiment, exemplary hepatocyte functional proteins include albumin (ALB), APOA2, APOB, F2, F10, Cytochrome P450 (CYP)3A4, CYP1A2, CYP2C9 and UGT2B7.

Kits for long-term maintenance of functional hepatocytes in culture are provided. The kit includes one activator of adenylate cyclase, one TGFβ inhibitor, one Notch inhibitor, one Wnt inhibitor, and one BMP inhibitor (herein, "5C"). A most preferred activator of adenylate cyclase activator is forskolin; a preferred TGFβ inhibitor is SB43; a preferred Notch inhibitor is DAPT; a preferred Wnt inhibitor is IWP 2 and a preferred BMP inhibitor is LDN.

Also disclosed are methods for identifying agents which improve maintenance of functional differentiated cells, for example, hepatocytes in vitro. The method includes comparing global gene expression profiles for freshly isolated primary hepatocytes with hepatocytes that have been cultured for only 24 hrs, and screening small molecule targets that participate in hepatic cell fate patterning, differentiation and reprogramming.

BRIEF DESCRIPTION OF THE DRAWINGS

FIG. 2A shows genes enriched in TGFβ signaling pathways were detected by RNA-Seq in hepatocytes cultured for 24 hours in HCM (24h-Cultured hepatocytes) and freshly isolated hepatocytes (F-PHHs). FIG. 2B shows gene expression of mesenchymal marker genes and hepatocyte functional genes in PHHs cultured under different conditions, detected by qRT-PCR. n=2. Relative gene expression was normalized to F-PHHs.

FIG. 4A is a line graph showing MTT assay to analyze cell survival under different culture conditions. n=3. FIG. 4B shows the synergistic effects between SB43 and FSK (termed as 2C) were observed on the regulation of mesenchymal marker genes and hepatocyte functional gene expression, detected by RT-qPCR. Relative gene expression is normalized to F-PHHs. FIG. 4C shows qRT-PCR analysis of surrogate hepatic functional markers in cultured hepatocytes after 4 weeks in culture. Relative gene expression was normalized to F-PHHs. n=2. (FIG. 4I) Inhibition of CYP450 activities in 2C-PHHs was detected by LC/MS in 2C-cultured hepatocytes. n=3. KC, Ketoconazole; SX, Sulfaphenazole; ANF, α-Naphthoflavone. FIG. 5A is a scheme showing chemical screening to discover candidates that synergistically cooperate with SB43 and FSK. FIG. 5B shows the effect of DAPT, LDN193189 and IWP 2 when individually combined with SB43 and FSK on EMT gene expression (suppressed) or hepatic functional gene expression (increased). Relative gene expression normalized to DMSO. n=2. FIG. 5C shows the effect of three additional small molecules (IWP 2, DAPT and LDN193189), which decreased the expression of mesenchymal marker genes COL1A1 in cultured PHHs when combined with SB43 and FSK. qRT-PCR analysis was performed at day 14. Relative gene expression was normalized to FSK+SB43. n=3. FIG. 5D shows the effect of substituting IWP 2, DAPT, and LDN193189 with small molecules or cytokines targeting the same signaling pathway on suppressing EMT markers. Relative gene expression was normalized to FSK+SB43. n=3. FIG. 5E shows the effect of each small-molecule of 5C on the maintenance of PHHs by single small-molecule omission assay. The expression of hepatic transcription factors and functional genes was detected by qRT-PCR. Relative gene expression was normalized to 5C. n=2.

FIG. 6D shows albumin secretion and urea synthesis assay for 60 days of PHHs cultured under 5C condition. n=3. Similar results were obtained in 2 independent batches. FIG. 6E shows qRT-PCR analysis of key hepatic genes in hepatocytes cultured under 5C condition (5C-PHHs) at day 60 and day 90. Relative expression level was normalized to F-PHHs. n=2.

FIG. 9A: Gene expression analysis for NTCP by qRT-PCR. n=3. FIG. 9B: Dynamics of the formation of HBV antigens (HBsAg and HBeAg) in the supernatant of infected PHHs cultured under different conditions. n=3. FIG. 9C: Dynamics of HBV RNA formation in cultured PHHs under different conditions analyzed by qRT-PCR. n=2. FIG. 9D: Dynamics of HBV DNA formation in the supernatant of cultured infected PHHs under different conditions. n=3. FIG. 9E: Dynamics of cccDNA formation in 5C-PHHs detected by qPCR. n=2. FIGS. 9F and 9G show detection of HBeAg (n=3) (FIG. 9F) and viral DNA (n=2) (FIG. 9G) in PHHs inoculated with the supernatant of HBV-infected 5C-PHHs.

FIGS. 11 E-F show the neutralizing antibody (anti-S antibody) block HBV spread in 5C-PHHs.

FIGS. 12A-D show the effect of anti-HBV drugs (ETV, LAM and IFN-$\alpha$) on HBV antigens (HBsAg and HBeAg) (FIG. 12A), HBV RNA (detected at 16 Dpi) (FIG. 12B), HBV DNA (detected at 21 Dpi) (FIG. 12C) and HBV cccDNA (detected at 34 Dpi) (FIG. 12D) in infected 5C-PHHs.

(FIG. 13B) qRT-PCR analysis of expression of hepatic functional genes of PHHs cultured under different culture conditions. n=3. (FIG. 13C) Time-course analysis for human albumin secretion and urea synthesis of PHHs cultured under different culture conditions. n=3. (FIG. 13D) Time course analysis of HBeAg. PHHs were infected with plasma from hepatitis B patients and further cultured under different conditions long-term. n=3. Similar results were obtained in 3 independent batches.

(FIG. 14A) EMT markers and hepatic functional genes were analyzed after 2 weeks of culture. (FIG. 14B) ALB secretion and urea synthesis were detected after 7 and 14 days of culture. (FIG. 14C) HBV infection was performed in microwell plates, and HBsAg and HBeAg were analyzed. n=3. Similar results were obtained in 2 independent batches.

(FIGS. 15A and B) Secreted HCV products (FIG. 15A) and intracellular HCV RNA (FIG. 15B) were measured. n=3. FIG. 15C shows qRT-PCR analysis of ISG expression in 5C-PHHs infected with HCV (shown here as Jc1G) and uninfected 5C-PHHs. n=3.

DETAILED DESCRIPTION OF THE INVENTION

Figure 1:
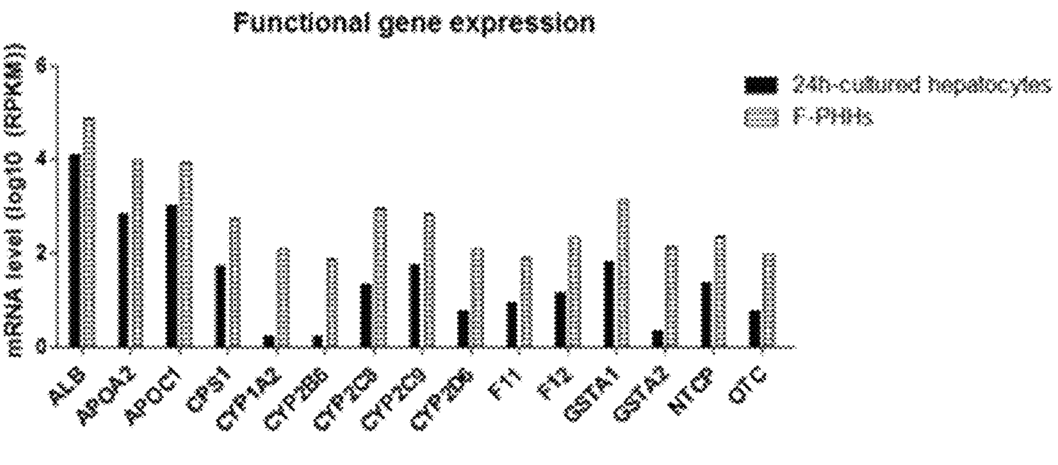
FIG. 1 shows mRNA levels of functional marker genes in hepatocytes cultured for 24 hours in HCM (24h-Cultured hepatocytes) and in freshly isolated hepatocytes (F-PHHs), analyzed by RNA-Seq.

Here, we demonstrate that this fundamental problem can be overcome in primary human hepatocytes (PHHs) by modulating cell signaling pathways with a small-molecule combination. A five-chemical condition (5C) was identified for long-term functional maintenance of PHHs. 5C cultured PHHs showed global gene expression profiles and hepatocyte-specific functions resembling freshly isolated human hepatocytes. The 5C cultured PHHs permitted hepatitis B virus (HBV), and efficiently recapitulated the entire course of HBV infection over four weeks, maintaining persistently detectable HBV covalently closed circular DNA (cccDNA). Our study provides an efficient platform for understanding HBV pathology and antiviral drug screening, and this chemical approach could be applicable to maintenance of other functional cell types in vitro.

The disclosed culture condition also maintained and promoted hESC-hepatocytes approaching an adult stage. Under our condition, hESC-hepatocytes could be maintained over one month and functional maturation of prolonged-cultured hESC-hepatocytes was observed. hESC-hepatocytes cultured under our condition progressively expressed a panel of CYP enzymes, indicating the functional maturation of hESC-hepatocytes close to an adult-like stage, which facilitate the generation of functionally mature cells from hPSCs.

I. Definitions

"5C medium" as use herein refers to basal cell culture medium for hepatocytes supplemented with at least one activator of adenylate cyclase, one TGFβ inhibitor, one Notch inhibitor, one Wnt inhibitor, and one BMP inhibitor, for example, HCM (hepatocyte culture medium, Lonza) or William's E medium containing 2% B27 (Gibco), 1% GlutaMAX, supplemented with Forskolin, SB431542, DAPT; IWP 2 and LDN193189.

As used herein a "culture" means a population of cells grown in a medium and optionally passaged. A cell culture may be a primary culture (e.g., a culture that has not been passaged) or may be a secondary or subsequent culture (e.g., a population of cells which have been subcultured or passaged one or more times).

As used herein, "downregulation" or "downregulate" refers to the process by which a cell decreases the quantity and/or activity of a cellular component, for example, DNA, RNA or protein, in response to an external variable.

The term "induced hepatocytes" (iHeps) as used herein refers to cells which are not naturally occurring hepatocytes, and which are artificially derived from non-hepatocyte cells.

The terms "oligonucleotide" and "polynucleotide" generally refer to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The term "nucleic acid" or "nucleic acid sequence" also encompasses a polynucleotide as defined above.

As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

"Reprogramming" as used herein refers to the conversion of a one specific cell type to another. For example, a cell that is not a hepatocyte can be reprogrammed into a cell that is morphologically and functionally like a hepatocyte.

The term "upregulate expression of" means to affect expression of, for example to induce expression or activity, or induce increased/greater expression or activity relative to an untreated cell.

As used herein, "upregulation" or "upregulate" refers to the process by which a cell increases the quantity and/or activity of a cellular component, for example, DNA, RNA or protein, in response to an external variable.

II. Compositions

The compositions include hepatocyte cell culture medium, supplemented with at least: one activator of adenylate cyclase, one TGFβ inhibitor, one Notch inhibitor, one Wnt inhibitor, and/or one BMP inhibitor.

In some preferred embodiments, the composition includes a combination of an activator of adenylate cyclase, and TGFβ inhibitor (herein, 2C).

In a more preferred embodiment, the compositions include an activator of adenylate cyclase, and TGFβ inhibitor in combination with at least one agent selected from the group consisting of a Notch inhibitor, a Wnt inhibitor, and a BMP inhibitor.

In a particularly preferred embodiment, the composition includes a combination of at least one activator of adenylate cyclase, one TGFβ inhibitor, one Notch inhibitor, one Wnt inhibitor, and one BMP inhibitor (herein, "5C"). A most preferred activator of adenylate cyclase activator is forskolin; a preferred TGFβ inhibitor is SB43; a preferred Notch inhibitor is DAPT; a preferred Wnt inhibitor is IWP 2 and a preferred BMP inhibitor is LDN193189.

The combination of compounds are added to any hepatocyte cell culture medium in an effective amount to maintain functional hepatocyte function in vitro, long term, measured in some embodiments as effective amounts of the compounds to maintain expression at least 6 hepatocyte functional proteins following at least 60 days in culture, at the same levels as freshly isolated primary hepatocytes from the same organism.

Useful cell culture media used for hepatocyte cell culture are known in the art (herein, "hepatocyte basal media"). Useful examples include, but at not limited to Williams' medium E containing B27, Glutmax and Pen Strep; hepatocyte medium; Dulbecco's Modified Eagle Medium ("DMEM") and Ham's F12 Medium, alone or in combination; Waymouth's MB-752/1, Ham's F12, RPMI 1640, Dulbecco's modified Eagle's medium, Leibovitz' L15, HBM™ (Lonza), hepatocyte basal medium WAJC 110 (MyBiosouirce.com) and modified Chee's medium.

A. Hepatocyte Cell Culture Medium Supplements

CAMP Agonists

The preferred cAMP agonist is Forskolin, used at concentration ranging from 2-100 μM, preferably from 5 and 50 μM, and more preferably, 18-22 μM. However, any cAMP agonist can be included in the cocktail of CINPs disclosed herein. Examples include, but are not limited to prostaglandin E2 (PGE2), rolipram, genistein and cAMP analogs such as DBcAMP or 8-bromo-cAMP.

TGFβ Inhibitors

The TGFβ inhibitor preferably inhibits the TGFβ type 1 receptor activing receptor-like kinase (ALK) 5 in some embodiments, and can additionally inhibit ALK 4 and the nodal type receptor 1 receptor ALK7 in other embodiments. The TGFβ receptor inhibitor can be SB431542 (4-[4-(1,3-benzodioxol-5-yl)-5-(2-pyridinyl)-1H-imidazol-2-yl]benzamide), the structure of which is shown below, used at a concentration between 2-50 μM, preferably between 2 and 15 M, and more preferably, between 8 and 12 μM.

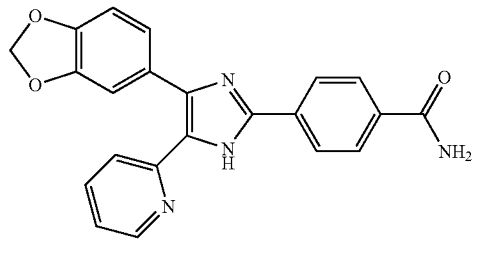 [SMILES: NC(=O)c1ccc(-c2nc(-c3ccc4c(c3)OCO4)c(-c3ccccn3)[nH]2)cc1]

Other TGFβ inhibitors which are known in the art and are commercially available. Examples include E-616452 ([2-(3-(6-Methylpyridin-2-yl)-1H-pyrazol-4-yl)-1,5-naphthyridine]; 83-01 [3-(6-Methyl-2-pyridinyl)-N-phenyl-4-(4-quinolinyl)-1H-pyrazole-1-carbothioamide]; SB 505124 [2-[4-(1,3-Benzodioxol-5-yl)-2-(1,1-dimethylethyl)-1H-imidazol-5-yl]-6-methyl-pyridine]; GW 788388 [4-[4-[3-(2-Pyridinyl)-1H-pyrazol-4-yl]-2-pyridinyl]-N-(tetrahydro-2H-pyran-4-yl)-benzamide]; and SB 525334 [6-[2-(1,1-Dimethylethyl)-5-(6-methyl-2-pyridinyl)-1H-imidazol-4-yl]quinoxaline], and dorsomorphine.

Notch Inhibitors

The compositions preferably include one or more notch inhibitors, more preferably, DAPT ((2S)—N-[(3,5-Difluorophenylacetyl]-L-alanyl-2-phenyl]glycine 1,1-dimethylethyl ester), the structure of which is shown below, used at a concentration between 0.1 and 10 UM, preferably between 0.5 and 2.5 μM, and more preferably, between 1 and 2 μM.

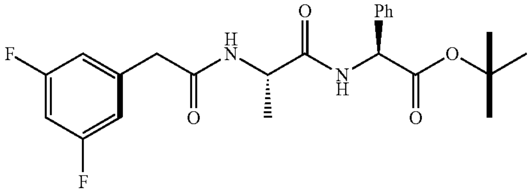

Other notch inhibitors are known in the art. Representative examples include MK 0752 the structure of which is shown below, used at a concentration between 0.02 and 20 μM, preferably, between 0.2 and 10 UM, more preferably, between 1 and 5 μM.

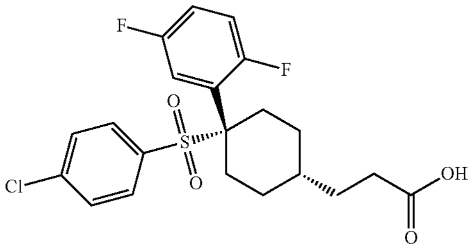 [SMILES: O=C(O)CC[C@H]1CC[C@@](c2cc(F)ccc2F)(S(=O)(=O)c2ccc(Cl)cc2)CC1]

RO4929097, the structure of which is shown below, used at a concentration between 0.02 and 20 UM, preferably, between 0.2 and 10 UM, more preferably, between 1 and 5 μM.

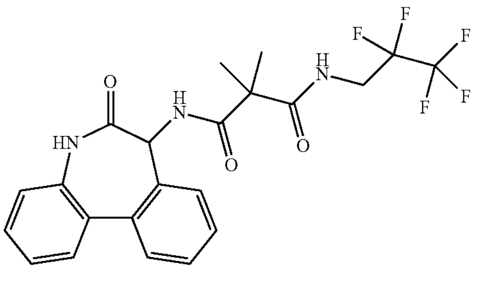 [SMILES: CC(C)(C(=O)NCC(F)(F)C(F)(F)F)C(=O)NC1C(=O)Nc2ccccc2-c2ccccc21]

XXi (S,S)-2-[2-(3,5-Difluorophenyl)-acetylamino]-N-(1-methyl-2-oxo-5-phenyl-2,3-dihydro-1H-benzo[e][1,4]diazepin-3-yl)-propionamide), used at preferred concentration between 0.2 and 1 μM; DBZ (N-[(1S)-2-[[(7S)-6,7-Dihydro-5-methyl-6-oxo-5H-dibenz[b,d]azepin-7-yl]amino]-1-methyl-2-oxoethyl]-3,5-difluorobenzeneacetamide); SAHM1 (peptide sequence AERLRRRIXLCRXHHST, with the following modifications: Ala-1=N-terminal Ac, Ala-1=β-Ala, X=(S)-2-(4-pentenyl) alanine, X-9 and X-13 stapled together with a double bond); and FLI 06 (Cyclohexyl 1,4,5,6,7,8-hexahydro-2,7,7-trimethyl-4-(4-nitrophenyl)-5-oxo-3-quinolinecarboxylate).

Wnt Inhibitors

The disclosed compositions can include one or more Wnt inhibitors. A preferred Wnt inhibitor is IWP 2 (N-(6-Methyl-2-benzothiazolyl)-2-[(3,4,6,7-tetrahydro-4-oxo-3-phenylthieno[3,2-d]pyrimidin-2-yl)thio]-acetamide) the structure of which is shown below, used, for example, at a concentration between 0.01 and 2.5 μM, preferably between 0.1 and 1 μM, and more preferably, between 0.5 and 1 μM.

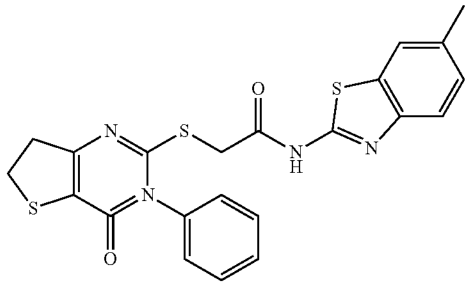

IWP 2 inhibits Wnt processing and secretion. It inactivates PORCN, a membrane-bound O-acyltransferase (MBOAT), and selectively inhibits palmitoylation of Wnt. Blocks Wnt-dependent phosphorylation of Lrp6 receptor and Dv12, and β-catenin accumulation.

Other Wnt signaling inhibitors are known in the art. Representative examples include Dickkopf-related protein 1 (DKK1), used at a preferred concentration between 10 and 1000 ng/ml, more preferably, between 50 and 150 ng/ml; IWR1 (4-(1,3,3a,4,7,7a-hexahydro-1,3-dioxo-4,7-methano-2H-isoindol-2-yl)-N-8-quinolinyl-benzamide), used at a preferred concentration between 0.1 and 5 μM, more preferably, between 1 and 2 μM; Wnt-C59 (4-(2-Methyl-4-pyridinyl)-N-[4-(3-pyridinyl)phenyl]benzencacetamide), used at a preferred concentration between 0.01 and 5 μM, more preferably, between 0.05 and 1 μM IWP L6 (N-(5-Phenyl-2-pyridinyl)-2-[(3,4,6,7-tetrahydro-4-oxo-3-phenylthieno[3,2-d]pyrimidin-2-yl)thiolacetamide) and IWP 12 (N-(6-Methyl-2-benzothiazolyl)-2-[(3,4,6,7-tetrahydro-3,6-dimethyl-4-oxothieno[3,2-d]pyrimidin-2-yl)thio]acetamide).

BMP Inhibitors

The composition includes one or more BMP inhibitors. A preferred BMP inhibitor is LDN193189 2HCL (4-[6-[4-(1-Piperazinyl)phenyl]pyrazolo[1,5-a]pyrimidin-3-yl]quinoline dihydrochloride), the structure of which is shown below, used for example, at a concentration between 0.01 and 0.5 μM, preferably between 0.05 and 0.25 UM, and more preferably, between 0.1 and 0.2 μM.

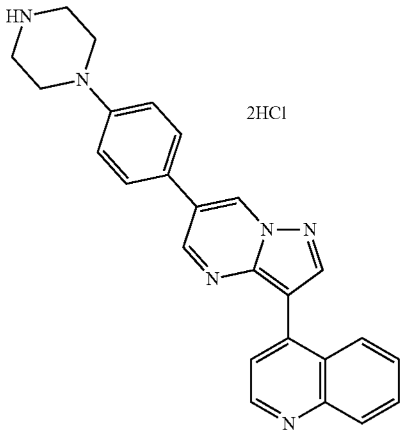 [SMILES: c1ccc2c(-c3cnn4cc(-c5ccc(N6CCNCC6)cc5)cnc34)ccnc2c1]

2HCl

LDN193189 is a potent and selective ALK2 and ALK3 inhibitor ($IC_{50}$ values are 5 and 30 nM, respectively); inhibits BMP4-mediated Smad1/5/8 activation. Exhibits >200-fold selectivity for BMP signaling over TGF-β signaling. Also exhibits selectivity over AMPK, PDGFR and MAPK signaling.

Other useful BMP inhibitors are known in the art. Representative examples include, but are not limited to LDN 212854 (5-[6-[4-(1-Piperazinyl)phenyl]pyrazolo[1,5-a]pyrimidin-3-yl]-quinoline); the structure of which is shown below, used at a preferred concentration between 0.05 and 5 μM, more preferably, between 0.1 and 2 μM.

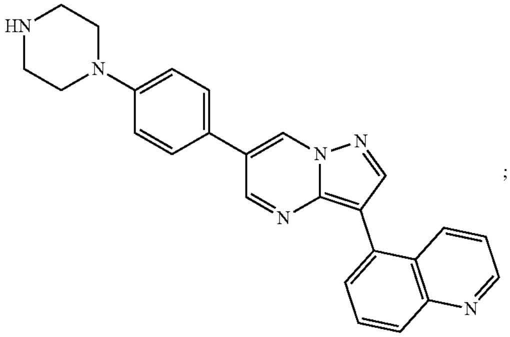 [SMILES: c1cc(-c2cnn3cc(-c4ccc(N5CCNCC5)cc4)cnc23)c2cccnc2c1]

;

Noggin, used at a preferred concentration between 10 and 1000 ng/ml, more preferably, between 50 and 500 ng/ml; Dorsomorphin dihydrochloride (6-[4-[2-(1-Piperidinyl)ethoxy]phenyl]-3-(4-pyridinyl)-pyrazolo[1,5-a]pyrimidine dihydrochloride); and K 02288 (3-[(6-Amino-5-(3,4,5-trimethoxyphenyl)-3-pyridinyl]phenol.

B. Hepatocytes Cultured in Small Molecule-Supplemented Media

Hepatocytes cultured using the supplemented hepatocyte culture media disclosed herein maintain functional hepatocytes long term in vitro, measured in terms of the hepatocytes having at least one characteristic selected from the group consisting of hepatocyte morphology (polygonal shape), established hepatocyte functions such as albumin secretion and urea synthesis, and expression at least one known hepatocyte marker. Expression levels of hepatocyte markers can be determined by measuring the expression levels of oligonucleotides encoding the hepatocyte markers or by measuring the protein levels, using methods known in the art and exemplified herein.

In one embodiment, the ability to maintain long-term maintenance of functional hepatocytes in vitro is measured in terms of the hepatocytes possessing at least one of the characteristics listed above, following at least two weeks in culture. In some embodiments, the hepatocytes possess at least one of the characteristics listed above, following three weeks in culture. For example, the hepatocytes possess at least one of the characteristics listed above following four weeks in culture, 5 weeks in culture, 6 weeks in culture, 7 weeks in culture, 8 weeks, 9 weeks and up to 90 days or more, in culture at improved levels, when compared hepatocytes obtained from the same organism and cultured without supplementing the cell culture medium using the hepatocyte cell culture supplements disclosed herein.

Hepatocyte markers that can be used to determine long term maintenance of functional hepatocytes in culture include, but are not limited to cytochrome P450 (CYP) 3A4; CYP1A2; CYP2C9; CYP2D6; CYP2B6; CYP2C8, CSP1, CYP2C19; UDP-glucuronosyltransferase (UGT) 1A3; UGT1A4; UGT2B15; UGT2B7, NTCP ($Na^+$-taurocholate cotransporting polypeptide); ABCG2 (ATP-binding cassette super-family G member 2,aka BCRP); MRP2 (Multidrug resistance-associated protein 2); organic-anion-transporting polypeptide (OATP) 1B1, APOA2, APOB, F2 (coagulation factor II), F10 (coagulation factor X). Thus, hepatocytes cultured in hepatocyte cell culture media supplemented as disclosed herein show improved expression of at least one of P450 (CYP) 3A4; CYP1A2; CYP2C9; CYP2D6; CYP2B6; CYP2C19 when compared to hepatocytes from the same organism, cultured with the same basal hepatocyte cell culture medium, not supplemented with the disclosed small molecules. Improved expression can be measured as a statistically significant difference in levels of expression.

In some preferred embodiment, hepatocytes cultured according to the methods disclosed herein express at least one of the hepatocyte markers listed above at levels that are comparable (measured as no statistically significant difference) or more, when compared to the levels expressed by freshly isolated hepatocytes from the same organism.

In a particularly preferred embodiment, hepatocytes maintained in vitro using the supplemented cell culture medium disclosed herein express at least one, at least two, at least 3, at least four, at least five or at least six of the following hepatocyte markers: APOA2, APOB, F2, F10, CYP3A4, CYP1A2, CYP2C9 and UTG2B7 at levels comparable to freshly isolated hepatocytes obtained from the same organism, at 90 days in culture.

The hepatocytes cultured in 5C have metabolically active CYP3A4, CYP1A2, CYP2C9, CYP2D6 and CYP2B6, after 2 weeks in culture, at levels comparable to those of F-PHHs. In contrast, the metabolizing activities of PHHs cultured in control groups (hepatocyte culture media without 5C supplementation) are almost undetectable at the same time point.

III. Methods of Using

A. Hepatocyte Culture

The disclosed cell culture compositions are used for hepatocyte culture for long-term maintenance of functional hepatocytes in vitro. The disclosed cell culture compositions can be used not only for maintenance of hepatocytes, but also for functional maturation of hepatocytes (such as hepatocytes generated from differentiation or reprogramming).

The disclosed methods in some embodiments do not rely on co-culture of the hepatocytes with a second cell type, for example stellate cells. However, other embodiments may use a co-culture format which includes a second cell type such as satellite cells. In some embodiments the cell culture is a sandwich culture format, disclosed for example, in Dunn, et al., *Biotechnol. Prog.,* 7:237-245 (1991).

Hepatocytes from any source can be cultured using the supplemented cell culture media disclosed herein. The hepatocytes can be isolated from an animal, for example, mouse, domestic animal, primates or humans. In a preferred embodiment, the hepatocytes are isolated from a human. The hepatocytes can also be induced hepatocytes (iHeps). For example, the iHeps can be obtained by reprogramming or differentiation. In some preferred embodiments, the hepatocytes are primary hepatocytes, and in some embodiments, the hepatocytes can be cryopreserved hepatocytes.

Primary hepatocytes can be isolated from a donor using methods known in the art, for example, using a twostep collagenase perfusion procedure (Lee et al., *J Vis Exp,* 79, e50615 (2013)) For example, liver samples are perfused with an appropriate perfusion buffer (PB) to remove blood cells, followed by treatment with perfusion buffer plus EDTA (PBE) and then perfusion buffer plus collagenase (PBC). An exemplary perfusion buffer is 0.15 M NaCl; 5 mM KCl; 25 mM $NaHCO_3$; 5 mM Glucose; 20 mM Hepes). The hepatocyte suspension is washed with a hepatocyte basal medium, for example, Williams' Medium E, filtered, and the isolated hepatocytes seeded in a tissue culture plate/matrix used for hepatocyte cell culture, and cultured with basal hepatocyte cell culture medium supplemented with one activator of adenylate cyclase, one TGFβ inhibitor, one Notch inhibitor, one Wnt inhibitor, and/or one BMP inhibitor.

In some embodiments, the isolated hepatocytes are seeded on a single layer of collagen, and a second layer of collagen may or may not be added to provide a sandwich type hepatocyte culture. Hepatocytes can also be cultured in forms like hepatic spheroids. When cultured on soft or non-adhesive extracellular matrix.

Preferable culture conditions include in a humidified incubator under 5% CO2 at 37° C.

The basal hepatocyte cell culture medium is supplemented with at least one of an adenylate cyclase, a TGFβ inhibitor, a Notch inhibitor, a Wnt inhibitor, and a BMP inhibitor. In some preferred embodiments, the basal hepatocyte cell culture medium is supplemented with a combination of an activator of adenylate cyclase, and TGFβ inhibitor.

In more preferred embodiments, the basal hepatocyte cell culture medium is supplemented with an activator of adenylate cyclase, and a TGFβ inhibitor in combination with at least one agent selected from the group consisting of a Notch inhibitor, a Wnt inhibitor, and a BMP inhibitor.

In a particularly preferred embodiment, the basal hepatocyte cell culture medium is supplemented with a combination of at least one activator of adenylate cyclase, one TGFβ inhibitor, one Notch inhibitor, one Wnt inhibitor, and one BMP inhibitor (herein, "5C"). A most preferred activator of adenylate cyclase activator is forskolin; a preferred TGFβ inhibitor is SB431542 (SB43); a preferred Notch inhibitor is DAPT; a preferred Wnt inhibitor is IWP 2 and a preferred BMP inhibitor is LDN193189.

B. Research Related Uses

The studies disclosed herein show that human hepatocytes cultured according to the methods disclosed herein could preserve drug metabolizing activities for long-term, thus providing a platform for pharmaceutical applications.

(i) Drug Testing

Liver parenchymal cells play a key role in drug development because the liver plays a central role in the metabolic activity of the drug. At present, the main cause of failure of a drug candidate is its ADME (absorption, distribution, metabolism, excretion) is not ideal. An essential part of drug discovery research is to the metabolic and toxicological effects of the candidate drug on liver cells, human liver parenchymal cells with full participation of drug metabolism. Currently the main hepatocytes used for in vitro drug development are human adult primary hepatocytes. Due to the difficulty of maintaining primary hepatocyte function in vitro, their application in drug development is quite limited. Hepatocytes cultured according to the methods disclosed herein which express drug-metabolizing genes long term in culture, and maintain the metabolizing activities long term in culture, and can be used to in vitro drug metabolism studies. As noted above, hepatocytes cultured in 5C have metabolically active CYP3A4, CYP1A2, CYP2C9, CYP2D6 and CYP2B6, after 2 weeks in culture, at levels comparable to those of F-PHHs. In contrast, the metabolizing activities of PHHs cultured in control groups (hepatocyte culture media without 5C supplementation) are almost undetectable at the same time point.

(ii) Liver Disease Models

The problem encountered in studies involving infectious diseases is the lack of adequate models. In vitro cultured hepatocytes can be used as cell models for study of parasitic infection of the liver, for example, infection by the hepatitis virus (hepatitis B, C, or D infections), malaria causing parasites. These models can provide an effective platform for the development of vaccines and drugs for treating infectious diseases, particularly diseases that infect the liver.

Hepatocytes cultured according to the method disclosed herein can as an in vitro model to study liver disease, for example, viral infection of the liver. Preferred examples infection by hepatitis virus and disease progression. In a particularly preferred embodiment, the hepatocytes can service as models for hepatitis B and C infection and disease progression.

Accordingly, the hepatocytes disclosed herein can be use as an in vitro hepatic parasitic infection model, produced by a method which includes inoculating the disclosed hepatocytes a hepatic parasite for a time effective for parasite infection and culturing the parasite-infected cells in vitro in HC supplemented hepatic basal medium.

The data in this application shows that inoculation of PHHs (cultured according to the methods disclosed herein) with plasma from HBV-infected patients or HBV particles generated in cell culture, led to successful HBV infection, with HBV products (secreted HBsAg, HBeAg and DNA particles) detected in the supernatant of 5C-PHH culture. The high-level generation of HBV products persisted for at least one month in 5C-PHHs. Formation of HBV cccDNA was detectable at 4 weeks in culture under 5C condition. Efficient HBV infection of 5C-PHHs was demonstrated by immunostaining for HBV core antigen (HBcAg) (data not shown). Furthermore, 5C-PHHs were still sensitive to HBV infection when MOI (multiplicity of infection) was reduced to 10. HBV infection could be achieved at MOI=10, indicating that 5C-PHHs was a very sensitive system for HBV infection.

Importantly, 5C can stably support HBV infection from various sources, including HBV of various genotypes and from in vitro producer cell line HepAD38. 5C-PHHs can support the entire HBV life cycle and generate infectious particles of HBV.

Furthermore, the 5C-PHH can also be infected with other hepatitis viruses, such as the hepatitis C virus (HCV).

Hepatocytes cultured according to the methods disclosed herein can also be used to text efficacy of treatment options/new therapeutic agents for liver disease.

The data in this application exemplifies hepatocytes, cultured as disclosed herein, which respond to viral therapy. The 5C-PHH infection model sensitively responded to two classes of clinical anti-HBV drugs.

The successful inoculation of hepatocytes with hepatitis virus, can be extended to other parasites which infect the liver, for example, malaria parasite.

Malaria is a mosquito-borne infectious disease caused by microorganisms belonging to the *Plasmodium* group; it affects humans and other animals. Five species of *Plasmodium* can infect and be spread by humans. Most deaths are caused by *P. falciparum* because *P. vivax, P. ovale*, and *P. malariae* generally cause a milder form of malaria. The disease is most commonly transmitted by an infected female *Anopheles* mosquito. The mosquito bite introduces the parasites from the mosquito's saliva into the blood of the subject bitten. The parasites travel to the liver where they mature and reproduce.

V. Kits

Kits for long-term maintenance of functional hepatocytes in culture are provided. The kit includes one activator of adenylate cyclase, one TGFβ inhibitor, one Notch inhibitor, one Wnt inhibitor, and one BMP inhibitor (herein, "5C"). A most preferred activator of adenylate cyclase activator is forskolin; a preferred TGFβ inhibitor is SB431542 (SB43); a preferred Notch inhibitor is DAPT; a preferred Wnt inhibitor is IWP 2 and a preferred BMP inhibitor is LDN193189. The kits include instructions for supplementing basal hepatocyte cell culture media with the at least one activator of adenylate cyclase, one TGFβ inhibitor, one Notch inhibitor, one Wnt inhibitor, and one BMP inhibitor.

Examples

Materials and Methods

Human Hepatocyte Isolation and Culture

The present study was approved by the Research Ethics Committee of China-Japan Friendship Hospital (Ethical approval No: 2009-50). PHHs were obtained from human donors. Human hepatocytes were isolated from discarded human livers. A modified two-step collagenase perfusion procedure was used to isolate primary human hepatocytes from these tissues (OOtani, et al., *Nat Med.,* 15:701-706 (2009)). Briefly, the liver tissue was perfused with PB (perfusion buffer: 0.15 M NaCl; 5 mM KCl; 25 mM $NaHCO_3$; 5 mM Glucose; 20 mM Hepes) to remove remaining blood cells, followed by PBE (perfusion buffer plus 1 mM EDTA) perfusion. The tissue was then perfused with PBC (perfusion buffer plus 1 mg/mL collagenase type IV, 5 mM CaCl2, Gibco). All the buffers were prewarmed to 37° C. prior to the isolation process. The hepatocytes suspension was collected and washed with Williams' Medium E (Gibco), then filtered through a 40 μm Nylon cell strainer (Falcon). The isolated hepatocytes were then seeded on collagen type I-coated (Rat tail collagen type I, Gibco) plates at a density of $2.5\times10^5$/cm2.

Commercial Hepatocytes: Plateable cryopreserved human hepatocytes (Lot: HVN and HNN) were purchased from BioreclamationIVT (Product number: M00995-P).

Serum-free medium used for hepatocyte culture (Null): Williams' medium E containing B27 (50×, Gibco), Glutmax (Gibco) and Pen Strep (Gibco). DMSO vehicle control: Null supplemented with nearly 0.035% DMSO. 5C condition: Null supplemented with Forskolin (10 μM), SB431542 (10 μM), IWP 2 (1 μM), DAPT (1 μM), and LDN193189 (0.5 μM). 24h-Cultured hepatocytes were cultured in commercial medium HCM (Lonza).

Cryopreservation and Recovery of Human Hepatocytes

The hepatocytes were cryopreserved at a concentration of $1*10^7$ cells/mL (1 mL/vial), with a cryopreservation medium containing 60% Williams' Medium E (Gibco), 30% HypoThermosol FRS (BioLife Solutions) and 10% DMSO (Sigma-Aldrich). The vials were then transferred into a Cryo 1° C. freezing Container (Nalgene) immediately and frozen in a −80° C. freezer for 24 hr. Subsequently, the vials were transferred into liquid nitrogen for long-term storage.

For recovery, cryopreserved hepatocyte vials were thawed in a 37° C. water bath. 1 mL cell suspension was then added to 5 mL Null, followed by centrifugation at 160 g for 5 min at 4° C., then resuspension in culture medium. Cell viability was verified by Trypan blue (Gibco).

Small Molecule Compounds and Cytokines

The small molecule compounds and cytokines used for screening were purchased or synthesized as described in Table 1. Their concentrations are shown in Table 1.

TABLE 1
Small molecules or cytokines used in hepatocytes culture.
| Full Name | Abbreviation | Concentration | Source | Molecular Weight | Structure |
|---|---|---|---|---|---|
| Forskolin | FSK | 20 μM | Enzo, Cat.No. BML-CN100-0100 | 410.50 | 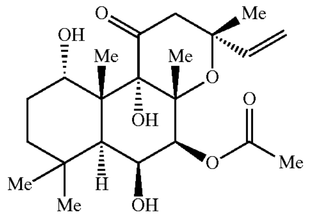 |
| SB431542 | SB43 | 10 μM | TOCRIS, Cat.No. 1614 | 384.39 | 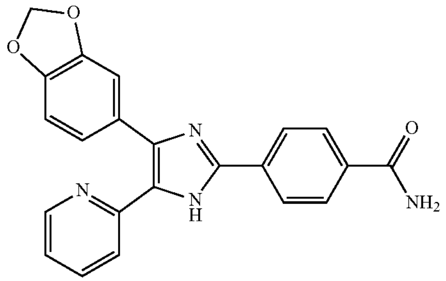 [SMILES: NC(=O)c1ccc(-c2nc(-c3ccc4c(c3)OCO4)c(-c3ccccn3)[nH]2)cc1] |
| DAPT | | 1 μM | TOCRIS, Cat.No. 2634 | 432.46 | 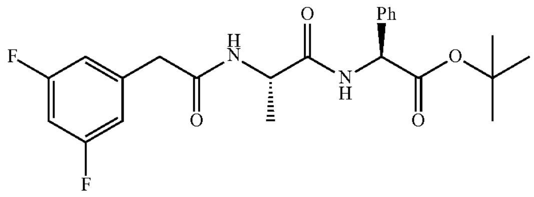 [SMILES: C[C@H](NC(=O)Cc1cc(F)cc(F)c1)C(=O)N[C@H](C(=O)OC(C)(C)C)c1ccccc1] |

TABLE 1-continued
| Small molecules or cytokines used in hepatocytes culture. | | | | | |
|---|---|---|---|---|---|
| Full Name | Abbreviation | Concentration | Source | Molecular Weight | Structure |
| IWP 2 | | 0.5 μM | TOCRIS, Cat.No. 3533 | 466.60 | 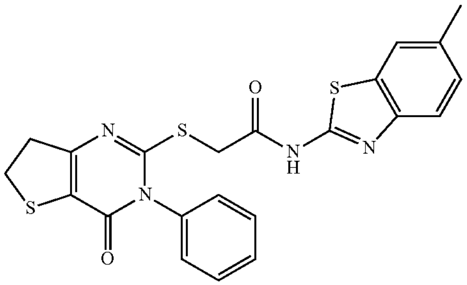 [SMILES: Cc1ccc2nc(NC(=O)CSc3nc4c(c(=O)n3-c3ccccc3)SCC4)sc2c1] |
| LDN193189 dihydrochloride | LDN | 0.1 μM | TOCRIS, Cat.No. 6053 | 479.40 | 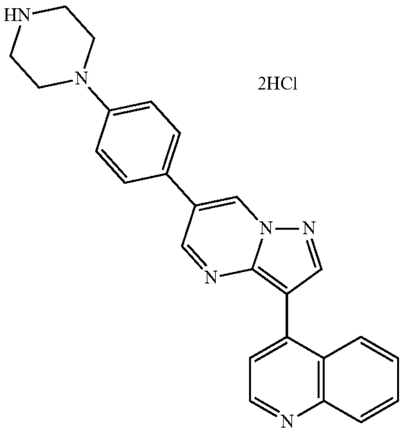 [SMILES: c1ccc2c(-c3cnn4cc(-c5ccc(N6CCNCC6)cc5)cnc34)ccnc2c1] 2HCl |

TABLE 1-continued
Small molecules or cytokines used in hepatocytes culture.
| Full Name | Abbreviation | Concentration | Source | Molecular Weight | Structure |
|---|---|---|---|---|---|
| Dibutyryl-cAMP, sodium salt | db-cAMP | 50 μM | TOCRIS, Cat.No. 1141 | 491.37 | 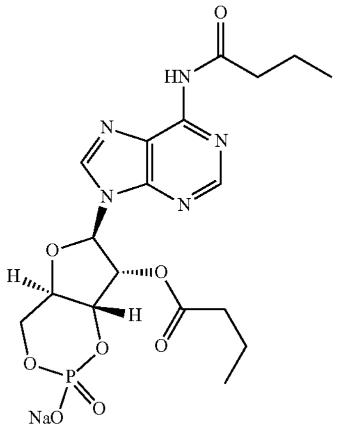 |
| FGF2 | | 20 ng/mL | Origene, Cat.No. TP750002 | | |
| PD173074 | | 1 μM | Selleckchem, Cat.No. S1264 | 523.67 | 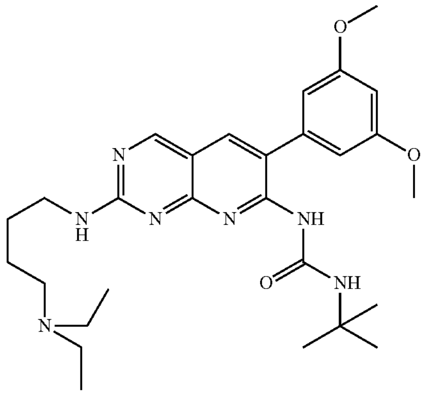 [SMILES: CCN(CC)CCCCNc1ncc2cc(-c3cc(OC)cc(OC)c3)c(NC(=O)NC(C)(C)C)nc2n1] |
| BMP4 | | 20 ng/mL | Stemimmune, Cat.No. HST-B4-0100 | | |
| Noggin | | 100 ng/mL | peprotech, Cat.No. 120-10C | | |

TABLE 1-continued

| Small molecules or cytokines used in hepatocytes culture. | | | | | |
|---|---|---|---|---|---|
| Full Name | Abbreviation | Concentration | Source | Molecular Weight | Structure |
| Recombinant Human Activin A | Activin A | 100 ng/mL | Stemimmune, Cat.No. HST-A-0100 | | |
| Recombinant Human IGF-I | IGF1 | 50 ng/ml | peprotech, Cat.No. 100-11 | | |
| Wortmannin | | 1 μM | Selleckchem, Cat.No. S2758 | 428.43 | 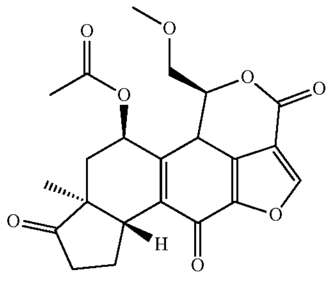 [SMILES: COC[C@H]1OC(=O)c2coc3c2C1C1=C(C3=O)[C@@H]2CCC(=O)[C@@]2(C)C[C@H]1OC(C)=O] |
| Recombinant Human EGF | EGF | 20 ng/mL | Stemimmune, Cat.No. EME-EF-0100 | | |
| Recombinant Human Wnt3a | Wnt3a | 25 ng/ml | R&D, Cat.No. 5036-WN-010 | | |
| SHH | | 20 ng/ml | Peprotech, Cat.No. 100-45 | | |
| SANT1 | | 1 μM | Selleckchem, Cat.No. S7092 | 373.49 | 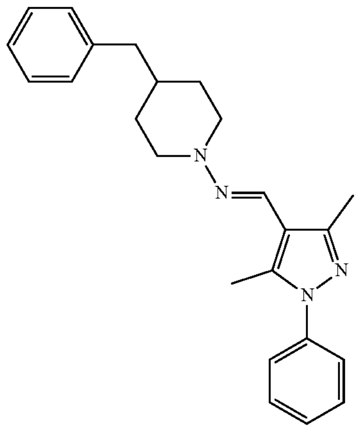 [SMILES: Cc1nn(-c2ccccc2)c(C)c1/C=N/N1CCC(Cc2ccccc2)CC1] |

TABLE 1-continued
| Small molecules or cytokines used in hepatocytes culture. | | | | | |
|---|---|---|---|---|---|
| Full Name | Abbreviation | Concentration | Source | Molecular Weight | Structure |
| H89 dihydrochloride | H89 | 210 μM | TOCRIS, Cat.No. 2910 | 519.28 | 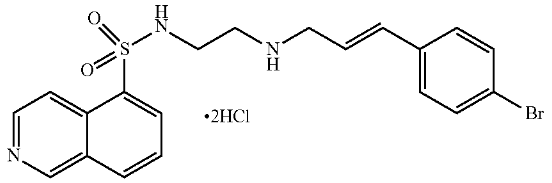 [SMILES: O=S(=O)(NCCNC/C=C/c1ccc(Br)cc1)c1cccc2cnccc12] •2HCl |
| TPB | a-Amyloid Precursor Protein Modulator | 0.5 μM | Santa cruz, Cat.No. sc-204424 | 501.55 | 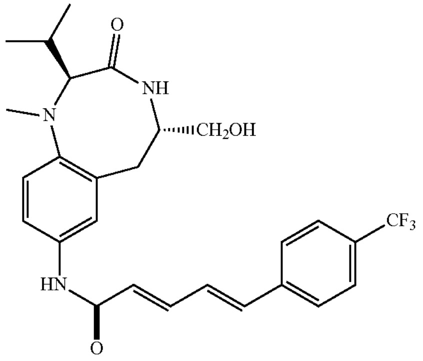 [SMILES: CC(C)[C@H]1C(=O)N[C@H](CO)Cc2cc(N[C@H](O)/C=C/C=C/c3ccc(C(F)(F)F)cc3)ccc2N1C] |
| Go6983 | | 2 μM | Selleckchem, Cat.No. S2911 | 442.51 | 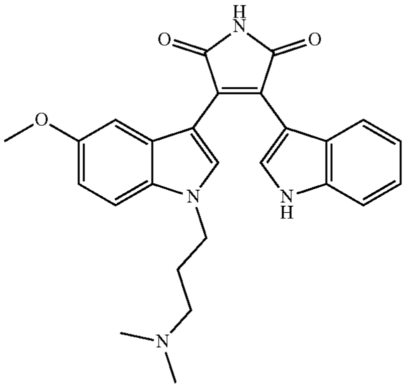 [SMILES: COc1ccc2c(c1)c(C1=C(c3c[nH]c4ccccc34)C(=O)NC1=O)cn2CCCN(C)C] |

TABLE 1-continued
Small molecules or cytokines used in hepatocytes culture.
| Full Name | Abbreviation | Concentration | Source | Molecular Weight | Structure |
|---|---|---|---|---|---|
| SB203580 | | 10 µM | Selleckchem, Cat.No. S1076 | 377.43 | 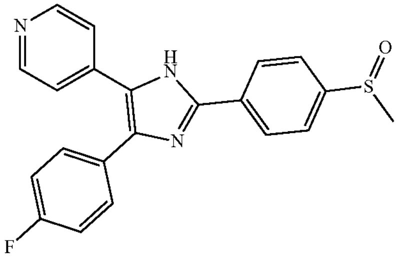 [SMILES: CS(=O)c1ccc(-c2nc(-c3ccc(F)cc3)c(-c3ccncc3)[nH]2)cc1] |
| PS48 | | 5 µM | SIGMA, Cat.No. P0022 | 286.75 | 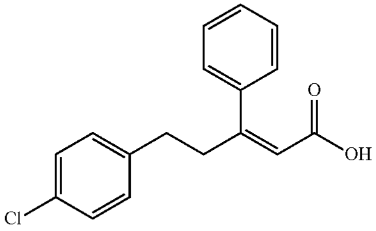 [SMILES: O=C(O)/C=C(/CCc1ccc(Cl)cc1)c1ccccc1] |
| TTNPB | | 2 µM | TOCRIS, Cat.No. 0761 | 348.48 | 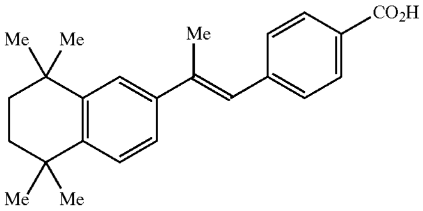 [SMILES: C/C(=C\c1ccc(C(=O)O)cc1)c1ccc2c(c1)C(C)(C)CCC2(C)C] |

TABLE 1-continued
| Small molecules or cytokines used in hepatocytes culture. | | | | | |
|---|---|---|---|---|---|
| Full Name | Abbreviation | Concentration | Source | Molecular Weight | Structure |
| WH4023 | | 1 μM | Synthesized by WUXI APPTEC | 568.28 | 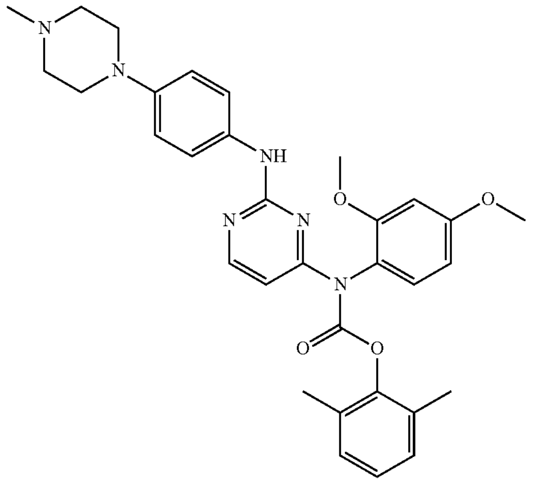 |
| Tranylcypromine | | 10 μM | Enzo, Cat.No. BML-EI217-0005 | 182.20 | 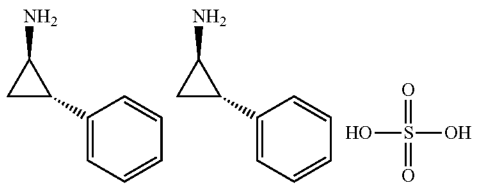 |

TABLE 1-continued
| Small molecules or cytokines used in hepatocytes culture. | | | | | |
|---|---|---|---|---|---|
| Full Name | Abbreviation | Concentration | Source | Molecular Weight | Structure |
| EPZ04777 | EPZ | 5 μM | Synthesized by WUXI APPTEC | 539.67 | 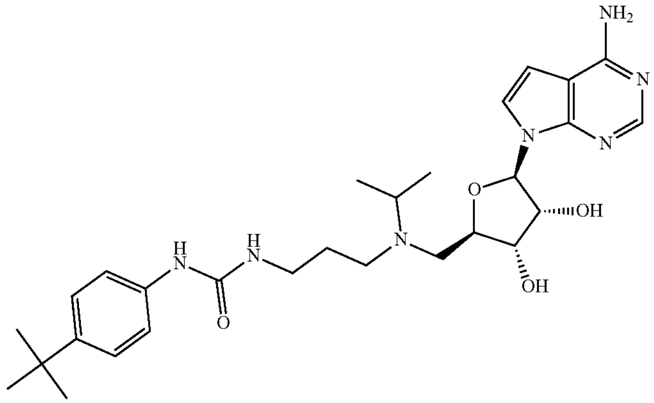 [SMILES: CC(C)N(CCCNC(=O)Nc1ccc(C(C)(C)C)cc1)C[C@H]1O[C@@H](n2ccc3c(N)ncnc32)[C@H](O)[C@@H]1O] |
| 3-deazaneplanocin A | Dznep | 0.05 μM | Synthesized by WUXI APPTEC | 262.26 | 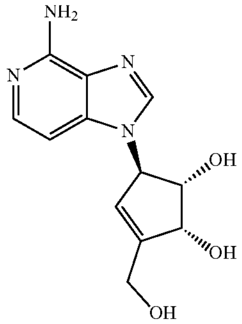 [SMILES: Nc1nccc2c1ncn2[C@@H]1C=C(CO)[C@@H](O)[C@H]1O] |

TABLE 1-continued
| Small molecules or cytokines used in hepatocytes culture. | | | | | |
|---|---|---|---|---|---|
| Full Name | Abbreviation | Concentration | Source | Molecular Weight | Structure |
| Bix01294 | | 1 μM | Stemgent, Cat.No. 04-0002 | 490.64 | 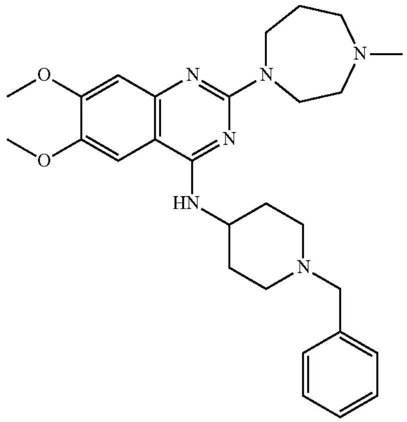 |
| LY294002 hydrochloride | Ly294002 | 2 μM | TOCRIS, Cat.No. 1130 | 343.81 | 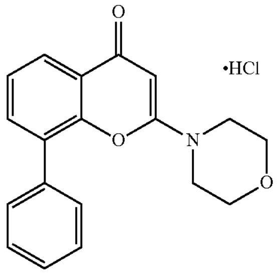 [SMILES: O=c1cc(N2CCOCC2)oc2c(-c3ccccc3)cccc12 ; Cl] |

TABLE 1-continued
Small molecules or cytokines used in hepatocytes culture.
| Full Name | Abbreviation | Concentration | Source | Molecular Weight | Structure |
| --- | --- | --- | --- | --- | --- |
| Sorafenib | | 5 μM | Selleckchem, Cat.No. S7397 | 464.82 | 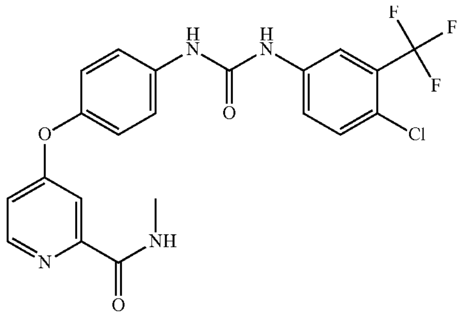 [SMILES: CNC(=O)c1cc(Oc2ccc(NC(=O)Nc3ccc(Cl)c(C(F)(F)F)c3)cc2)ccn1] |
| PD0325901 | | 0.5 μM | Synthesized by WUXI APPTEC | 482.00 | 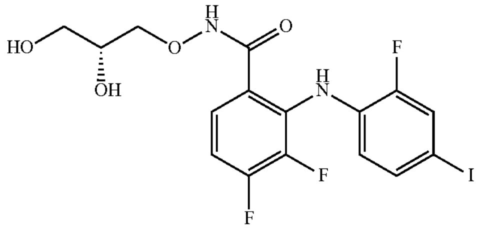 [SMILES: O=C(NOC[C@H](O)CO)c1ccc(F)c(F)c1Nc1ccc(I)cc1F] |
| PMA | | 0.1 μM | TOCRIS, Cat.No. 1201 | 616.83 | 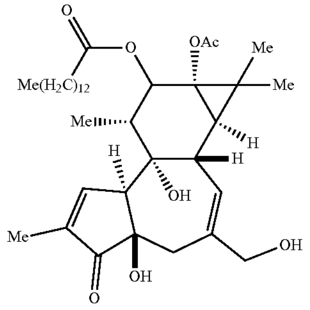 |

TABLE 1-continued
| Small molecules or cytokines used in hepatocytes culture. | | | | | |
|---|---|---|---|---|---|
| Full Name | Abbreviation | Concentration | Source | Molecular Weight | Structure |
| Rapamycin | | 0.1 μM | Selleckchem, Cat.No. S1039 | 914.18 | 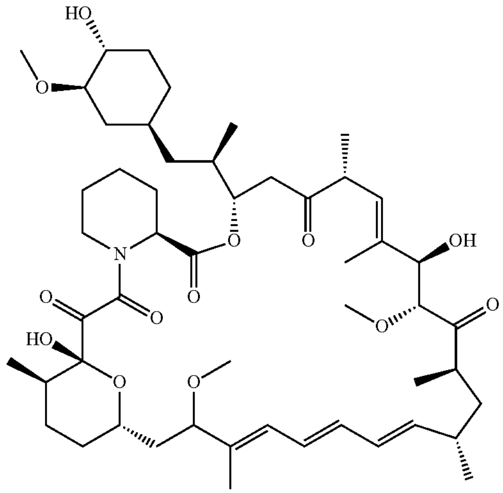 [SMILES: COC1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C] |
| SP600125 | | 5 μM | BIOCHEMPARTNER, Cat.No. 129-56-6 | 220.23 | 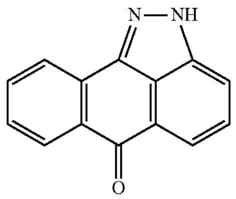 [SMILES: O=C1c2ccccc2-c2n[nH]c3cccc1c23] |
| Sunitinib Malate | Sunitinib | 2 μM | Selleckchem, Cat.No. S1042 | 532.56 | 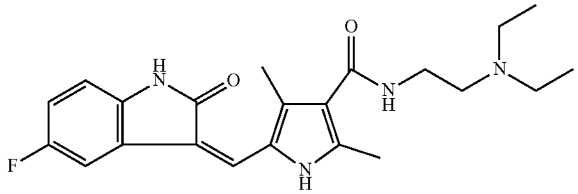 [SMILES: CCN(CC)CCNC(=O)c1c(C)[nH]c(/C=C2\C(=O)Nc3ccc(F)cc32)c1C] |

TABLE 1-continued
| Small molecules or cytokines used in hepatocytes culture. | | | | | |
|---|---|---|---|---|---|
| Full Name | Abbreviation | Concentration | Source | Molecular Weight | Structure |
| SB202190 | | 2 μM | MEDCHEM, Cat.No.152121-30-7 | 331.34 | 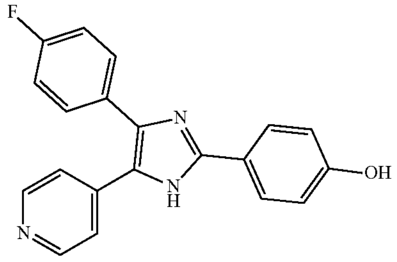 [SMILES: Oc1ccc(-c2nc(-c3ccc(F)cc3)c(-c3ccncc3)[nH]2)cc1] |
| interferon-a | IFN-a | 3.7 ng/mL | GENWAY | | |
| entecavir | ETV | 0.5 μM | Selleckchem, Cat.No. S1252 | 295.29 | 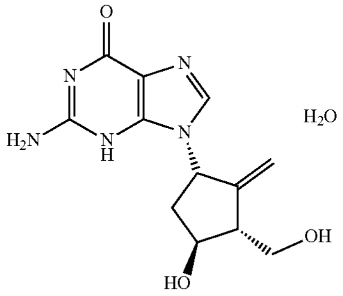 |
| lamivudine | LAM | 1 μM | Selleckchem, Cat.No. S1706 | 229.26 | 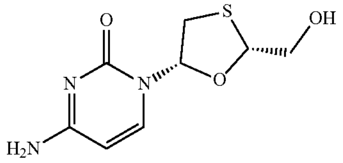 |

TABLE 1-continued
Small molecules or cytokines used in hepatocytes culture.
| Full Name | Abbreviation | Concentration | Source | Molecular Weight | Structure |
|---|---|---|---|---|---|
| 1,9-Dideoxyforskolin | 1,9d-FSK | 10 μM | santa cruz,cat.No.sc201 560A | 378.50 | 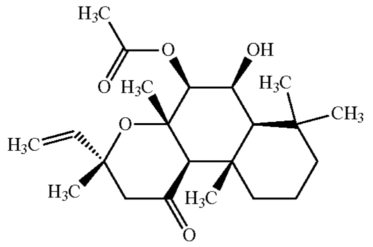 [SMILES: C=C[C@@]1(C)CC(=O)[C@@H]2[C@@]3(C)CCCC(C)(C)[C@@H]3[C@H](O)[C@H](OC(C)=O)[C@@]2(C)O1] |
| Dibutyryl-cAMP, sodium salt | db-cAMP | 50 μM | TOCRIS,cat.No.1 141 | 491.37 | 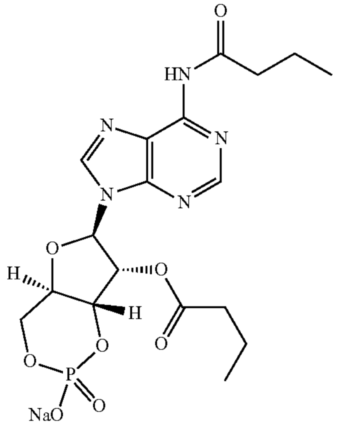 |
| NKH477 | | 10 μM | TOCRIS, cat.No.1 603 | 546.10 | 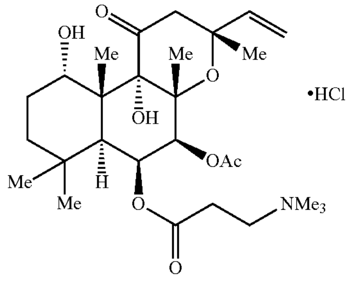 |

TABLE 1-continued
| Small molecules or cytokines used in hepatocytes culture. | | | | | |
|---|---|---|---|---|---|
| Full Name | Abbreviation | Concentration | Source | Molecular Weight | Structure |
| A83-01 | | 1 μM | TOCRIS,cat.No.2 939 | 421.52 | 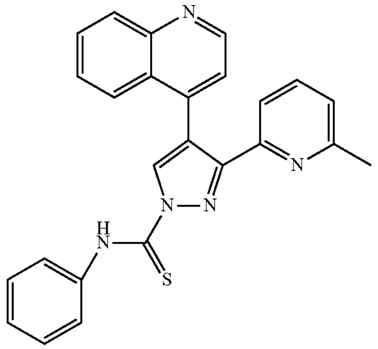 [SMILES: Cc1cccc(-c2nn(C(=S)Nc3ccccc3)cc2-c2ccnc3ccccc23)n1] |
| 616452 | | 5 μM | Synthesized by WUXI APPTEC | 400.34 | 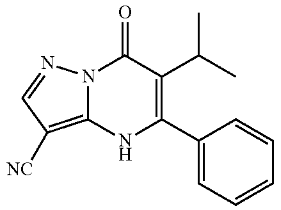 [SMILES: CC(C)c1c(-c2ccccc2)[nH]c2c(C#N)cnn2c1=O] |

TABLE 1-continued
| Small molecules or cytokines used in hepatocytes culture. | | | | | |
|---|---|---|---|---|---|
| Full Name | Abbreviation | Concentration | Source | Molecular Weight | Structure |
| Daclatasvir | DCV | 10 μM | Selleckchem, Cat.No. S1482 | 738.88 | 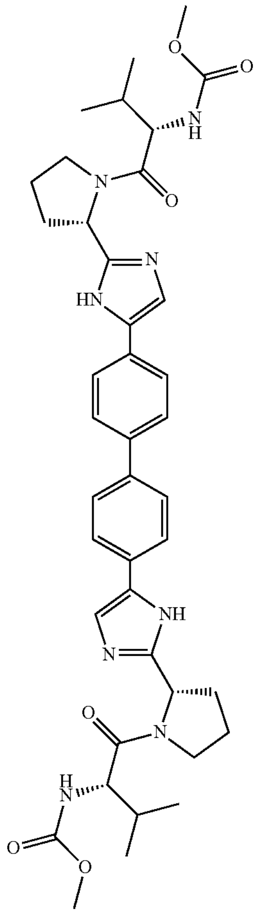 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C] |

TABLE 1-continued
| Small molecules or cytokines used in hepatocytes culture. | | | | | |
|---|---|---|---|---|---|
| Full Name | Abbreviation | Concentration | Source | Molecular Weight | Structure |
| 5 (and 6)-carboxy-2’ ,7’ -dichlorofluorescein diacetate | CDFDA | 2 µM | AAT Bioquest, Cat.No.22025 | 529.28 | 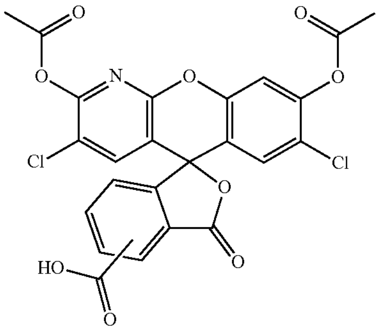 |
| Wnt-C59 | | 0.1 µM | Selleckchem, Cat.No. S7037 | 379.45 | 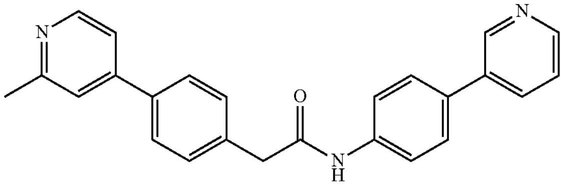 [SMILES: Cc1cc(-c2ccc(CC(=O)Nc3ccc(-c4cccnc4)cc3)cc2)ccn1] |
| IWR-1-endo | | 0.5 µM | Selleckchem, Cat.No. S7086 | 409.44 | 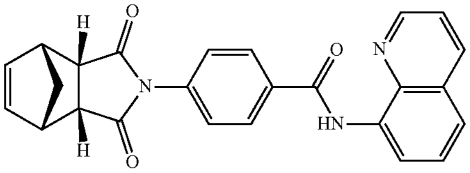 [SMILES: O=C(Nc1cccc2cccnc12)c1ccc(N2C(=O)[C@@H]3[C@H](C2=O)[C@@H]2C=C[C@H]3C2)cc1] |
| DKK1 | | 100 ng/mL | Peprotech Cat.No. 120-30-2 | | |

TABLE 1-continued
Small molecules or cytokines used in hepatocytes culture.
| Full Name | Abbreviation | Concentration | Source | Molecular Weight | Structure |
|---|---|---|---|---|---|
| MK-0752 | | 2 μM | Selleckchem, Cat.No. S2660 | 442.9 | 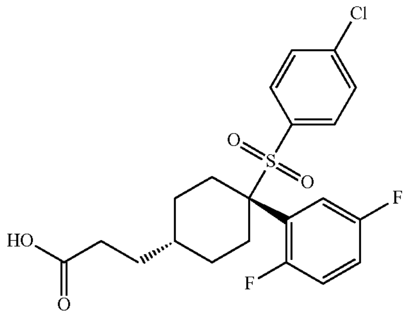 [SMILES: O=C(O)CC[C@H]1CC[C@@](c2cc(F)ccc2F)(S(=O)(=O)c2ccc(Cl)cc2)CC1] |
| RO4929097 | | 2 μM | Selleckchem, Cat.No. S1575 | 469.4 | 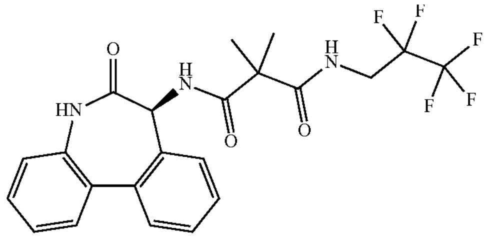 |
| γ -Secretase inhibitor XX | XXi | 0.1 μM | Sigma Cat.No. SML0649-5MG | 463.48 | 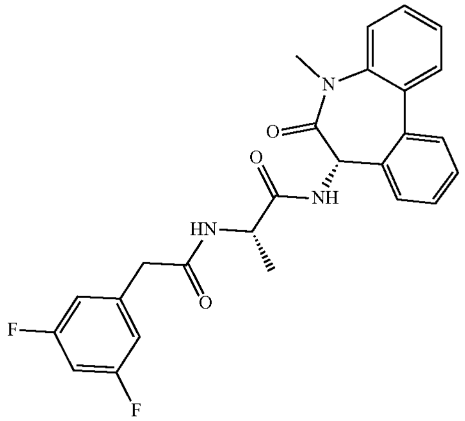 [SMILES: C[C@H](NC(=O)Cc1cc(F)cc(F)c1)C(=O)N[C@@H]1C(=O)N(C)c2ccccc2-c2ccccc21] |

TABLE 1-continued
| Small molecules or cytokines used in hepatocytes culture. | | | | | |
|---|---|---|---|---|---|
| Full Name | Abbreviation | Concentration | Source | Molecular Weight | Structure |
| LDN-212854 | | 0.5 μM | Selleckchem, Cat.No. S7147 | 406.48 | 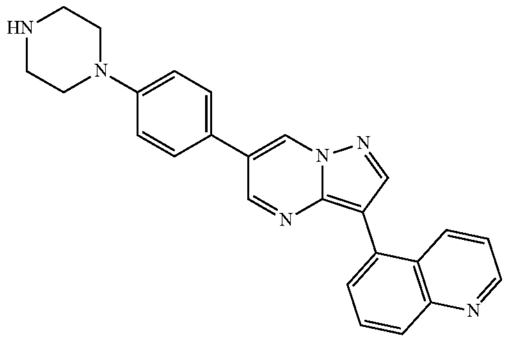 [SMILES: c1cc(-c2cnn3cc(-c4ccc(N5CCNCC5)cc4)cnc23)c2cccnc2c1] |
| Noggin | | 100 or 200 ng/mL | Peprotech Cat.No. 120-10C-1000 | | |

Drug Metabolizing Activity Assay

Drug metabolic activity was evaluated using a previously described method (Kyffin et al., *Toxicol. In vitro. An Int, J. Published in assoc with BBIBRA,* 48:262-275 (2018).). Briefly, hepatocytes were collected as cell suspensions to evaluate drug metabolizing activities. 1 mL of prewarmed incubation medium (Williams Medium E, 10 mM Hepes, PH 7.4, GlutaMAX) was added to $1\times10^6$ cells. Substrate solution was prepared by adding the substrate individually to incubation medium. Metabolizing reactions were initiated by mixing 250 μl substrate solution with 250 μl cell suspension in a 5 mL polystyrene round-bottom tube (BD Falcon). The tube was put on an orbital shaker set to shaker speed of 210 rpms in the incubator. After 15 to 120 min incubation at 37° C., the reaction tube was centrifuged at room temperature and the supernatant was collected. Drug metabolizing reactions were stopped by adding triple volumes of methanol to the collected supernatant and freezing at −80° C. To quantify the metabolites, an internal reference of 1% of each substrate was added and Liquid Chromatography/Mass Spectrometry (LC/MS) analysis was performed. The results were normalized to pmol of metabolite formed per minute per million cells. The specific substrates for each CYP enzyme and their concentration were shown in Table 2. Isotope-labeled reference metabolites and standard metabolites were listed Table 2.

and pelleted through 10-15% sucrose for 15 h at 112,000 g in a SW32 rotor. Pellets were resuspended in 2 ml of Null medium.

For CsCl density gradient purification, plasma was loaded on CsCl step gradients at densities from 1.1 to 1.5 g/ml (five step, each 2 ml). after centrifugation at 174,000 g for 35 h at 4° C. in a SW41 rotor (Beckman), gradient fractions were collected and the virus containing fraction was detected by the kit (KHB, Shanghai, China) though realtime PCR.

HBV Infection

Viral infections of HBV were conducted at genome equivalents of 200—i.e., $2\times10^7$ copies of genome equivalent HBV inoculated with $1\times10^5$ cells. The inoculum media was made fresh by initially dissolving PEG in Null for a final PEG concentration of 4% and without the addition of DMSO. The inoculum volume was adjusted to the plating format (25 μl for 384-well plates, 100 μl for 96-well plates and 500 μl for 24-well plates). After 20 h, inoculum was removed and cells were washed with PBS three times, followed by another three washes after 3 hr, and cultured in different conditions (Null/DMSO/5C) with medium change every 3 days. Cells were cultured (PEG free, DMSO free) for the indicated time before harvesting and further analysis. In some comparative experiments, inoculation was performed with MOI titration (10/50/100/200/400).

TABLE 2

CYP enzyme-selective substrates used for HPLC.

| CYP | Substrate | Concentration (μM) | Metabolite | Internal reference |
|---|---|---|---|---|
| CYP3A4 | Testosterone | 200 | Testosterone 6β-hydroxylation | 6β-Hydroxytestosterone-[D7] |
| CYP2D6 | Dextromethorphan | 15 | Dextromethorphan O-demethylation | Dextrorphan-[D3] |
| CYP1A2 | Phenacetin | 100 | Phenacetin-O-deethylation | Acetaminophen-[13C2, 15N] |
| CYP2B6 | Bupropion | 500 | Bupropion-hydroxylation | Hydroxybupropion-[D6] |
| CYP2C9 | Diclofenac | 25 | Diclofenac 4'-hydroxylation | 4'-Hydroxydiclofenac-[13C6] |

Preparation of HBV Stock

HBV virus was obtained from the plasma of chronic HBV carriers with written consent. HepAD38 cells were cultured in Dulbecco's modified minimal essential medium (DMEM) supplemented with 10% FBS and 0.1 mM non-essential amino acids (NEAA). After three days, when cells were confluent, the medium was changed to medium consisting of 3% FBS, 0.1 mM NEAA, and 2% DMSO. Supernatants were collected every three days and fresh medium was added. Collected media were pooled and concentrated 100-fold via centrifugation using centrifugal filter devices (Amicon Ultra-15, Regenerated Cellulose 100.000, Merck Millipore Corp.). The concentrated virus stock was aliquoted and stored at −80° C.

HBV purification by sucrose density gradient centrifugation was performed as described in Bremer et al. 2009 and Glebe and Gerlich, 2004. Briefly, HBV-infected patient plasma was loaded onto an ultracentrifuge tube containing a discontinuous sucrose gradient at densities 60%, 45%, 35%, 25% and 15%. Sucrose solutions were prepared with TNE (20 mM Tris-Hcl, 149 mM NaCl, 1 mM EDTA, pH 7.4). The plasma loaded tubes were then centrifuged in a SW32 rotor (Beckman) at 112,000 g for 15 h, 10° C. After centrifugation, the virus containing fraction (between the 45% and 35% fractions, as determined with detection kit (KHB, Shanghai, China) though real-time PCR) was diluted in TNE For reinfection, the supernatants of the HBV-infected 5C-PHHs were collected, concentrated 100-fold using centrifugal filter devices (Amicon Ultra-15, Regenerated Cellulose 100.000, Merck Millipore Corp.) via centrifugation at 3,000 g for 1 h at 4° C., and then used to inoculate naïve PHHs as the infection methods described above.

Detection of HBV Products

HBV viral antigens HBsAg and HBeAg were detected using 50 μl supernatants of cultured PHHs with commercial ELISA Kits (Autobio, Zhengzhou, China) following manufacturer's instructions.

For quantification of HBV DNA, viral DNA was isolated using the DNeasy Blood & Tissue Kit (QIAGEN, Cat No: 69504). The isolated DNA was quantified with detection kit (KHB, Shanghai, China) though real-time PCR. The viral genome equivalent copies were calculated based on a standard curve generated with known copy numbers.

For quantification of HBV-specific RNAs, total RNA from HBV-infected cells was isolated using the RNeasy Plus Mini Kit (QIAGEN). Approximately 400 ng total RNA was reverse transcribed into cDNA with TransScript First-Strand cDNA Synthesis SuperMix (TransGen Biotech). Primers 5'-GAGTGTGGATTCGCACTCC-3' (SEQ ID NO: 73) and 5-GAGGCGAGGGAGTTCTTCT-3' (SEQ ID NO: 74) were used for HBV 3.5 kb transcripts; primers 5'-TCACCAGCACCATGCAAC-3' (SEQ ID NO: 75) and 5'-AAGCCACCCAAGGCACAG-3' (SEQ ID NO: 76) were used for total HBV-specific transcripts. Amplification of a 123-bp fragment for 3.5 kb transcripts and 92-bp product for total HBV-specific transcripts were both conducted by denaturation at 95° C. for 30 s, followed by 40 cycles of 95° C. denaturation at 3 s/cycle, and 60° C. annealing/elongation for 30 s.

cccDNA detection method used in this study was performed. Briefly, DNA was isolated using the DNeasy Blood & Tissue Kit (QIAGEN, Cat No: 69504). Extracted DNA was digested with Plasmid-safe ATPdependent DNase (Epicentre Technologies) at 37° C. for 0.5 h and inactivated at 70° C. for 30 min. 0.5 μl of the 10 μl reaction was then added to a 10 μl real-time PCR reaction. The viral genome equivalent copies were calculated based on a standard curve generated with known copy numbers. Real-Time PCRs were carried out using Power SYBR® Green PCR Master Mix (Applied Biosystems) and performed on a CFX384™ Real-Time PCR detection system (Bio-Rad). For Southern Blot analysis of HBV cccDNA, HBV DNA was extracted by core DNA extraction method and an improved Hirt DNA extraction method. For Southern Blot, the prepared DNA sample was separated on a 0.8% agarose gel and then transferred to a nylon membrane (Amersham). To confirm the identity of cccDNA, Hirt DNA preparations from 5C-PHHs without treatment and with SpeI digestion were separated on an agarose gel. 1.7k-bp, 2.1k-bp and 3.1k-bp HBV DNA fragments containing labeled HBV probe (HBV DNA fragment from 370 bp to 705 bp, Southern Blot probe) was also run on the same agarose gel to serve as molecular markers for relaxed circular DNA (rcDNA), cccDNA and single-stranded DNA (ssDNA) in Southern Blot analysis. Southern Blot was performed with the DIG High Prime DNA Labeling and Detection Starter Kit II (Roche, 11 585 614 910). The primer sequences for preparation of DNA markers (genotype D, kindly provided by Professor Wenhui Li) are as follows: HBV 3.2 kb marker: HBV-D-EcorI-F 5'-GAATTCCACAACCTTTCACCAAA (SEQ ID NO: 77) HBV-D-EcorI-R 5'-GAATTCCACTGCATGGCCTGAGGATGA (SEQ ID NO: 78) HBV 2.1 kb marker: HBV-D-EcorI-F 5'-GAATTCCACAACCTTTCACCAAA (SEQ ID NO: 77) QYH-2.1 kb-R 5'-CCCAGGTAGCTAGAGTCATTAGT (SEQ ID NO: 79) HBV 1.7 kb marker: HBV-D-EcorI-F 5'-GAATTCCACAACCTTTCACCAAA (SEQ ID NO: 77) QYH-1.7 kb-R 5'-AAGGTCGGTCGTTGACATTGCAGAGA (SEQ ID NO: 80)

HCV Infection and Detection of HCV Products

The Huh7.5 cell line was kindly provided by Professor Charles Rice and was routinely maintained in Dulbecco modified medium supplemented with 10% fetal bovine serum (Biological industries), 25 mM HEPES (Gibco) and Non-Essential Amino Acid (Gibco). For generating the cell cultured HCV, the plasmid encoding HCV Jc1FLAG2 (p7-nsGluc2A) (Jc1G in the text) was first linearized by XbaI digestion, and used as template for in-vitro-transcription by using MEGAscript (Invitrogen). HCVcc was generated as described previously by electroporation of the in-vitro-transcribed Jc1G RNA into Huh7.5 cells. Virus containing supernatants were harvested each day after 3 days post electroporation' and up to 7 days post electroporation. Supernatants were combined and the virus was concentrated by centrifugation using Amicon® Ultra-15 (100K) Centrifugal Filter Devices (Millipore) at 5000 g for 30 min at 4° C. The buffer was exchanged into PBS by repeated centrifugation with Amicon® Ultra-15. The concentrated virus was titered in Huh7.5 by limited dilution method.

For quantification of intracellular HCV RNA, cells were lysed in Trizol reagent (Invitrogen). RNAs were purified from Trizol extraction and reverse transcribed using PrimeScript™ RT reagent Kit with gDNA Eraser (Perfect Real Time) from TaKaRa according to the manufacturer's instructions. The cDNA samples were subjected to real-time PCR (SYBR® Premix Ex Taq™ Tli RNaseH Plus) using primers for specific genes as listed. GAPDH: (s) GGT ATC GTG GAA GGA CTC ATG A (SEQ ID NO: 81), (as) ATG CCA GTG GCT TCC CGT TCA GC (SEQ ID NO: 82); HCV: (s) CCC TGT GAG GAA CTA CTG TCT TCA CGC (SEQ ID NO: 83), (as) GCT CAT GGT GCA CGG TCTA CGA GAC CT (SEQ ID NO: 84). The relative RNA levels were calculated using the 2-AACt method. GAPDH was used as a housekeeping gene for loading normalization.

For quantification of luciferase activity, supernatants from each well were taken and mixed with equal volume of 2× passive lysis buffer (Promega). Luciferase activity was measured with *Renilla* luciferase substrate (Promega) according to manufacturer's protocol.

Immunohistochemical Staining and Immunofluorescence Staining

The cells were fixed in 4% paraformaldehyde (DingGuo, AR-0211) at room temperature for 20 min, then permeabilized and blocked with PBS containing 3% normal donkey serum (Jackson Immuno Research, 017-000-121) and 0.25% Triton X-100 (Sigma-Aldrich, T8787) at room temperature for 60 min. Cells were then incubated with primary antibodies at 4° C. overnight. Secondary antibodies (Jackson ImmunoResearch) were incubated at room temperature for 1 hr. Nuclei were stained with DAPI (Roche Life Science, 10236276001). The primary antibodies used were listed in Table 3.

TABLE 3

Antibodies used for immunofluorescence staining.

| Gene | Antibody | Catalog Number |
|---|---|---|
| ALB | Human Albumin Antibody | A80-129A (Bethyl Laboratories, Inc.) |
| CYP3A4 | CYTOCHROME P450 3A4 | AHP622Z (AbD Serotec) |
| CYP1A2 | CYTOCHROME P450 1A2 | AHP610Z (AbD Serotec) |
| AAT | RABBIT ANTI HUMAN AAT | ZA-0007 (ZSGB-BIO) |
| CPS1 | Rabbit Anti Human CPS1 Antibody | ab45956 (Abcam) |
| HBcAg | Rabbit Anti-Hepatitis B Core Antigen (HBcAg) | B0586 (Dako) |

For detecting spread of HBV infection, immunohistochemical staining for HBcAg was performed. Briefly, the cells were fixed with 3.7% paraformaldehyde for 10 min at room temperature. After PBS wash, the cells were treated with 50% Ethanol in distilled water, and then with 70% ethanol in distilled water for at least 1 hour at 4° C. After blocking (blocking solution: PBS added with 10% FBS) for at least 2 hours, cells were incubated with anti-HBcAg (diluted 200 fold in blocking solution) overnight at 4° C. Primary antibodies were washed out and cells were treated with post-primary for 30 min at room temperature. Cells were incubated with secondary antibody for 30 min at RT. The staining media was made fresh by diluting 50×DAB in DAB diluent, then 150 μL substrate solution was added into each well. After DAB reaction, the cells were counterstained with hematoxylin for 5-10 min.

qRT-PCR

Total RNA was isolated using the RNeasy Micro Kit (QIAGEN). RNA was converted to cDNA using First-Strand Synthesis SuperMix for qRT-PCR (Invitrogen). PCR was carried out using Power SYBR® Green PCR Master Mix (Applied Biosystems) and performed on an MX3000P Sequence Detection System (Stratagene). The data were analyzed using the delta-delta Ct method. The primers used for qRT-PCR were listed in Table 4.

TABLE 4

Primers used for qRT-PCR.

| Gene | Forward Primer (5' to 3') | Reverse Primer (5' to 3') |
|---|---|---|
| ALB | GCACAGAATCCTTGGTGA ACAG (SEQ ID NO: 1) | ATGGAAGGTGAATGTTT CAGCA (SEQ ID NO: 2) |
| APOA2 | CTGTGCTACTCCTCACCA TCT (SEQ ID NO: 3) | CTCTCCACACATGGCTC CTTT (SEQ ID NO: 4) |
| APOB | TGCTCCACTCACTTTACC GTC (SEQ ID NO: 5) | TAGCGTCCAGTGTGTAC TGAC (SEQ ID NO: 6) |
| APOC1 | TCCAGTGCCTTGGATAAG CTG (SEQ ID NO: 7) | GGCTGATGAGTTCCCGA GC (SEQ ID NO: 8) |
| ARG1 | GTGGAAACTTGCATGGAC AAC (SEQ ID NO: 9) | AATCCTGGCACATCGGG AATC (SEQ ID NO: 10) |
| ASMA | CAGCCAAGCACTGTCAGG (SEQ ID NO: 11) | CCAGAGCCATTGTCACA CAC (SEQ ID NO: 12) |
| ATF5 | CTATGAGGTCCTTGGGGG AG (SEQ ID NO: 13) | CTCGCTCAGTCATCCAG TCA (SEQ ID NO: 14) |
| BCRP | CTGAGATCCTGAGCCTTT GG (SEQ ID NO: 15) | AAGCCATTGGTGTTTCC TTG (SEQ ID NO: 16) |
| CAR | GTCCCACCTGCCCCTTTG (SEQ ID NO: 17) | AGTGGCGCCTCTGAGTC TTG (SEQ ID NO: 18) |
| CEBPA | ACAAGAACAGCAACGAGT ACCG (SEQ ID NO: 19) | CATTGTCACTGGTCAGC TCCA (SEQ ID NO: 20) |
| COL1A1 | CACACGTCTCGGTCATGG TA (SEQ ID NO: 21) | AAGAGGAAGGCCAAGTC GAG (SEQ ID NO: 22) |
| CPS1 | AATGAGGTGGGCTTAAAG CAAG (SEQ ID NO: 23) | AGTTCCACTCCACAGTT CAGA (SEQ ID NO: 24) |
| CREB3L3 | GCCCTGCCTCTCCTATCA TC (SEQ ID NO: 25) | ACGGTGAGATTGCATCG TGG (SEQ ID NO: 26) |
| CYP1A2 | CTTCGTAAACCAGTGGCA GG (SEQ ID NO: 27) | AGGGCTTGTTAATGGCA GTG (SEQ ID NO: 28) |
| CYP2A6 | GAGTTCCTGTCACTGTTG CG (SEQ ID NO: 29) | GTCCTGGCAGGTGTTTC ATC (SEQ ID NO: 30) |
| CYP2B6 | CCGGGGATATGGTGTGAT CTT (SEQ ID NO: 31) | CCGAAGTCCCTCATAGT GGTC (SEQ ID NO: 32) |
| CYP2C19 | GAAGAGGAGCATTGAGGA CCG (SEQ ID NO: 33) | GCCCAGGATGAAAGTGG GAT (SEQ ID NO: 34) |
| CYP2C8 | CTCGGGACTTTATGGATT GC (SEQ ID NO: 35) | CAGTGCCAACCAAGTTT TCA (SEQ ID NO: 36) |
| CYP2C9 | GCCACATGCCCTACACAG ATG (SEQ ID NO: 37) | TAATGTCACAGGTCACT GCATGG (SEQ ID NO: 38) |
| CYP2D6 | GTGTCCAACAGGAGATCG ACG (SEQ ID NO: 39) | CACCTCATGAATCACGG CAGT (SEQ ID NO: 40) |
| CYP3A4 | AGCCTGGTGCTCCTCTAT CT (SEQ ID NO: 41) | CCCTTATGGTAGGACAA AAT (SEQ ID NO: 42) |
| F10 | CACTGGTCGCCATCTTTG TA (SEQ ID NO: 43) | AGTGCATGGAAGAGACC TGC (SEQ ID NO: 44) |
| F2 | GGCTCTTCATGACAAAGG GT (SEQ ID NO: 45) | ATCCGCATCACTGACAA CAT (SEQ ID NO: 46) |
| FOXA1 | GTGGCTCCAGGATGTTAG GA (SEQ ID NO: 47) | AGGCCTGAGTTCATGTT GCT (SEQ ID NO: 48) |
| FOXA3 | GAGATGCCGAAGGGGTAT CG (SEQ ID NO: 49) | TGATTCTCCCGGTAGTA AGGG (SEQ ID NO: 50) |

TABLE 4-continued

Primers used for qRT-PCR.

| Gene | Forward Primer (5' to 3') | Reverse Primer (5' to 3') |
|---|---|---|
| HNF1A | CCATCCTCAAAGAGCTGG AG (SEQ ID NO: 51) | GTGCTGCTGCAGGTAGG ACT (SEQ ID NO: 52) |
| HNF4A | CCAAAACCCTCGTCGACA TG (SEQ ID NO: 53) | TTCTCAAATTCCAGGGT GGTGTA (SEQ ID NO: 54) |
| HNF6A | TGTGGAAGTGGCTGCAGG A (SEQ ID NO: 55) | TGTGAAGACCAACCTGG GCT (SEQ ID NO: 56) |
| HNF6B | CGAACACTCTTCGCCATC TTC (SEQ ID NO: 57) | GTTGCTGACGGTTGTGA GCTC (SEQ ID NO: 58) |
| KLF15 | GTGAGAAGCCCTTCGCCT (SEQ ID NO: 59) | CACACAGGACACTGGTA CGG (SEQ ID NO: 60) |
| MRP2 | GGGATCTCTTCCACACTG GAT (SEQ ID NO: 61) | CATACAGGCCCTGAAGA GGA (SEQ ID NO: 62) |
| NAGS | GTTGGAGAAGCTGCCATC AC (SEQ ID NO: 63) | CGGGACCTTCAGACACT TTT (SEQ ID NO: 64) |
| NR0B2 | AGGGACCATCCTCTTCAA CC (SEQ ID NO: 65) | ACTTCACACAGCACCCA GTG (SEQ ID NO: 66) |
| NTCP | AGGGGGACATGAACCTCA G (SEQ ID NO: 67) | AGGTCCCCATCATAGAT CCC (SEQ ID NO: 68) |
| OATP1B1 | TTCAATCATGGACCAAAA TCAA (SEQ ID NO: 69) | TGAGTGACAGAGCTGCC AAG (SEQ ID NO: 70) |
| PROX1 | ACAGGGCTCTGAACATGC AC (SEQ ID NO: 71) | GGCATTGAAAAACTCCC GTA (SEQ ID NO: 72) |

RNA-Seq

Total RNA was isolated using the RNeasy Plus Mini Kit (QIAGEN). RNA sequencing libraries were constructed using the Illumina mRNA-Seq Prep Kit (Illumina). Fragmented and randomly primed 150 bp paired-end libraries were sequenced using Illumina HiSeq 4000.

Software and algorithms used for transcriptome analysis are including Cutadapt 1.16 (http://cutadapt.readthedocs.io/en/stable/guide.html), Salmon 0.8.2 (https://combinelab.github.io/salmon/), and R 3.5.0 (https://www.r-project.org). The expression profiles of HepG2, F-PHHs-3 and F-PHHs-4 were downloaded as raw data. The expression profiles of PHH Od, hiPSC-Hep rep1, hiPSC-Hep rep2, hiPSC-Hep rep3 and hiPSC-Hep rep4 (Gordillo, et al., *Development,* 142:2094-2108 (2015)) were downloaded as raw sequencing reads from GEO database (GSM2817112, GSM2753376, GSM2753377, GSM2753378, GSM2753379). To compare gene expression profile between paired-end and single end libraries, we used the read1 from our generated sequencing paired-end reads. The read1 and the downloaded single-end read were trimmed to the same 40 bp length by using Cut adapt. The expression values for each sample were quantified by Salmon. Unsupervised hierarchical clustering of RNA-Seq data was generated by hclust package in R.

Biochemical Assays

Human albumin was measured using the Human Albumin ELISA Quantitation kit (Bethyl Laboratories). Urea concentration was measured by the QuantiChrom™ Urea Assay Kit (BioAssay Systems). The MTT assay was done at indicated time points according to the manufacturer's instructions (Vybrant® MTT Cell Proliferation Assay Kit, Invitrogen).

Statistical Analysis

For statistical analysis, a two-tailed unpaired t test was used. The results are expressed as the mean±SEM and n indicates the number of replicates from the same batch of PHHs. p values are as follows: * $p<0.05$;  $p<0.01$; * $p<0.001$; **** $p<0.0001$.

Results and Discussion

Figure 2A:
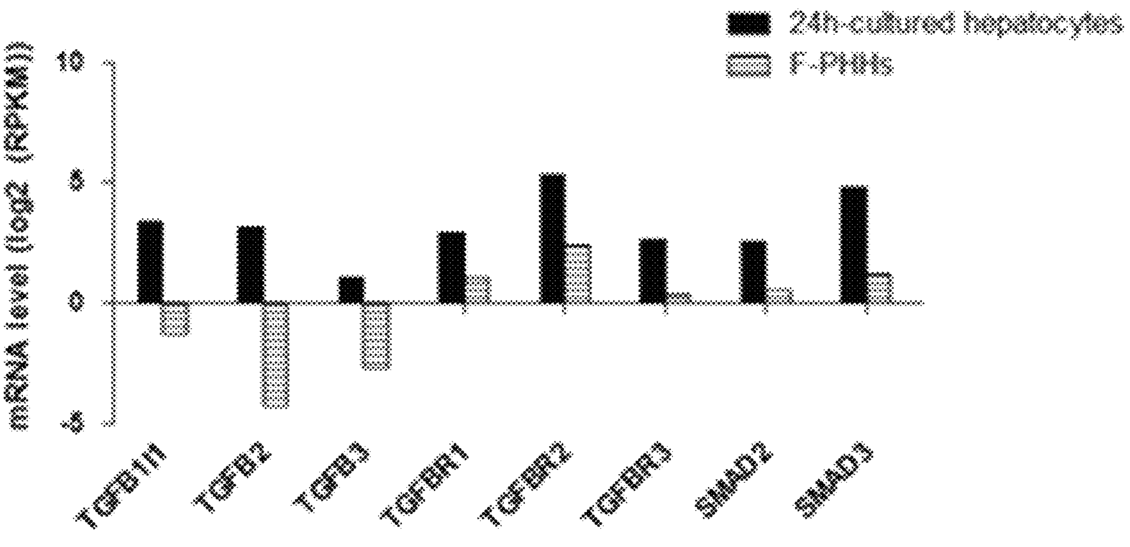
FIGS. 2A and 2B show identification of TGF-β inhibitor (SB431542) as a factor that partially supported PHH maintenance in vitro.

To maintain PHHs in vitro long-term, a new chemical strategy was developed, using small-molecule combinations. Owing to their ability to achieve flexible spatiotemporal modulations of specific cellular targets, small molecules confer the advantage of synergistically orchestrating innate signals in cultured cells. To identify small molecules facilitating PHHs maintenance, RNA sequencing (RNA-Seq) was first used to compare the global gene expression profiles of freshly isolated primary human hepatocytes (F-PHHs) with hepatocytes that had been cultured for only 24 hours in vitro. In line with previous studies, key hepatocyte functional genes were dramatically down regulated after a 24-hour culture (FIG. 1). Remarkably, the expression of major components of the TGF-β signaling pathway was up-regulated in the 24-hour cultured hepatocytes (FIG. 2A).

Previous studies had shown that TGF-β signaling was the master inducer of epithelial-mesenchymal transition (EMT) for hepatocytes. Therefore, the TGF-β inhibitor SB431542 (SB43) was used to block TGF-β signaling-induced EMT, and with SB43 treatment, cultured hepatocytes maintained an epithelial morphology with the expression of E-cadherin even after 2 weeks (data not shown). However, the blockage of TGF-β signaling failed to suppress the expression of EMT-associated transcription factors Snail Family Transcriptional Repressor 2 (SNAI2); Twist-related protein 1

Figure 2B:
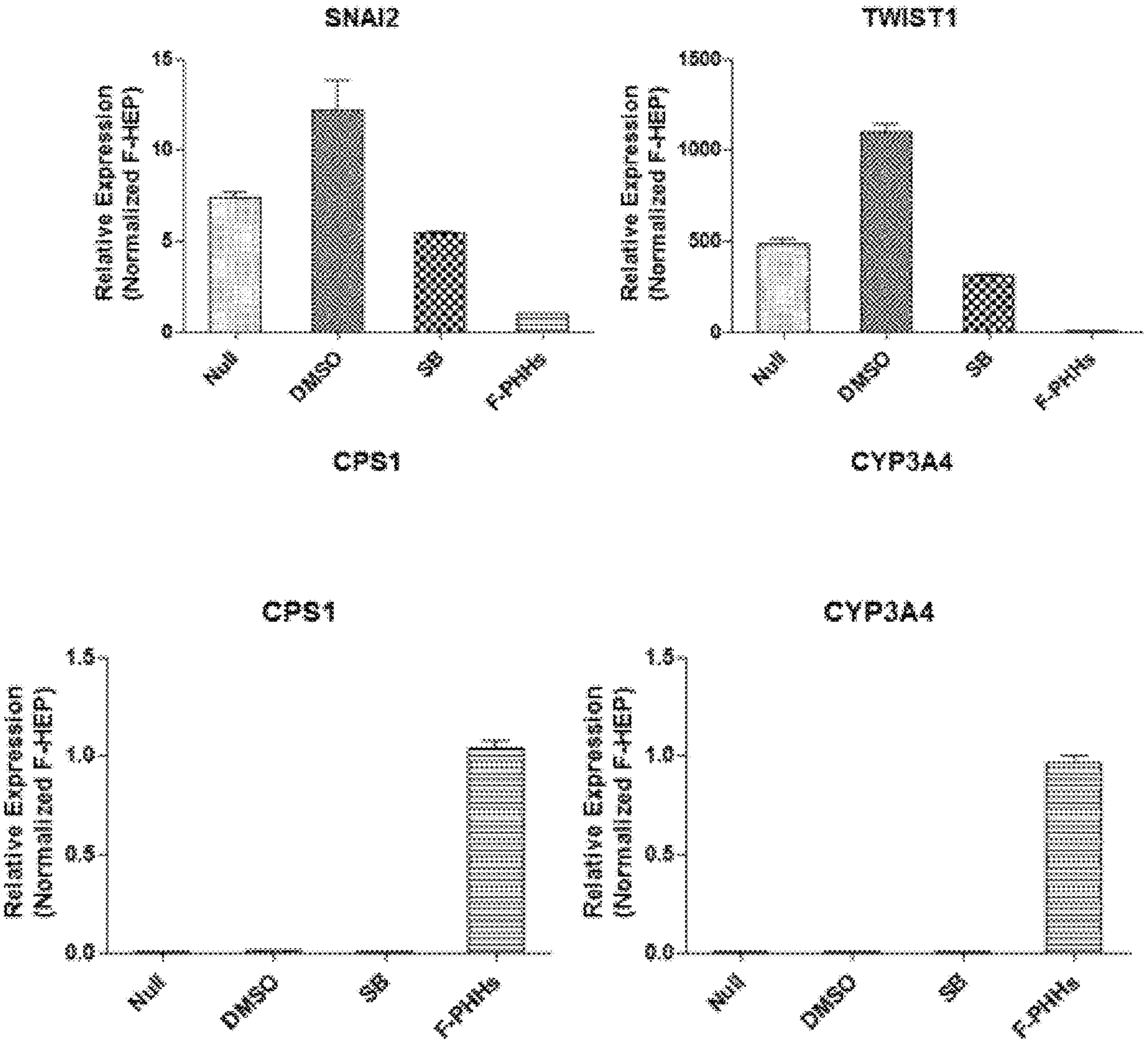
Figure 2B:
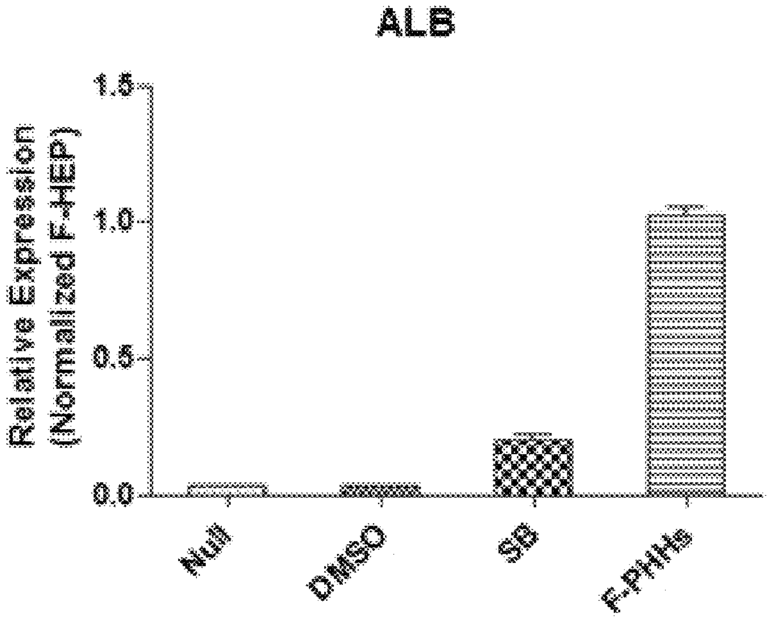
Figure 2B:
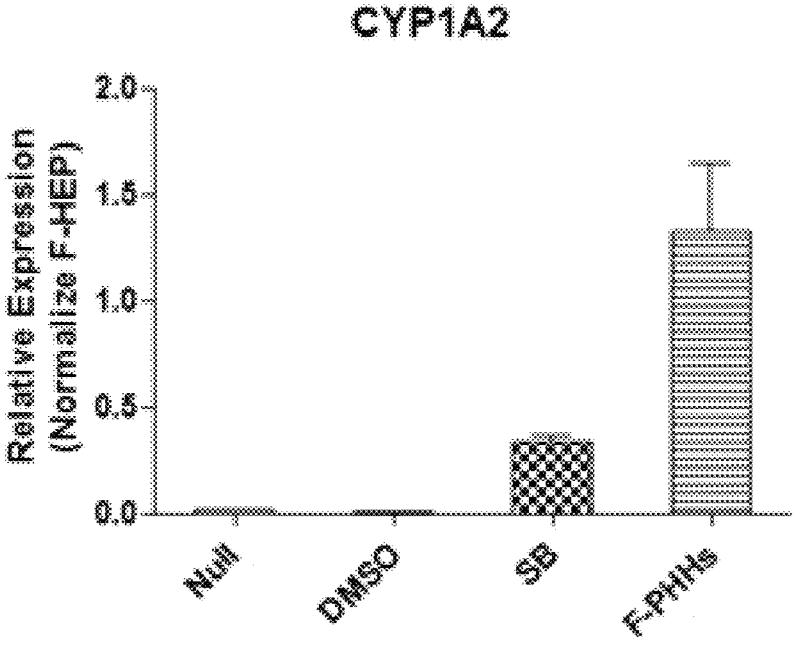

(TWIST1) and to rescue the expression of hepatic functional genes (ALB; CPS1 (carbamoyl phosphate synthetase-1); CYP3A4 and CYP1A2) (FIG. 2B), indicating that blocking TGF-β signaling partially suppressed EMT but had limited effect on maintaining the functional state of PHHs.

Figure 3A:
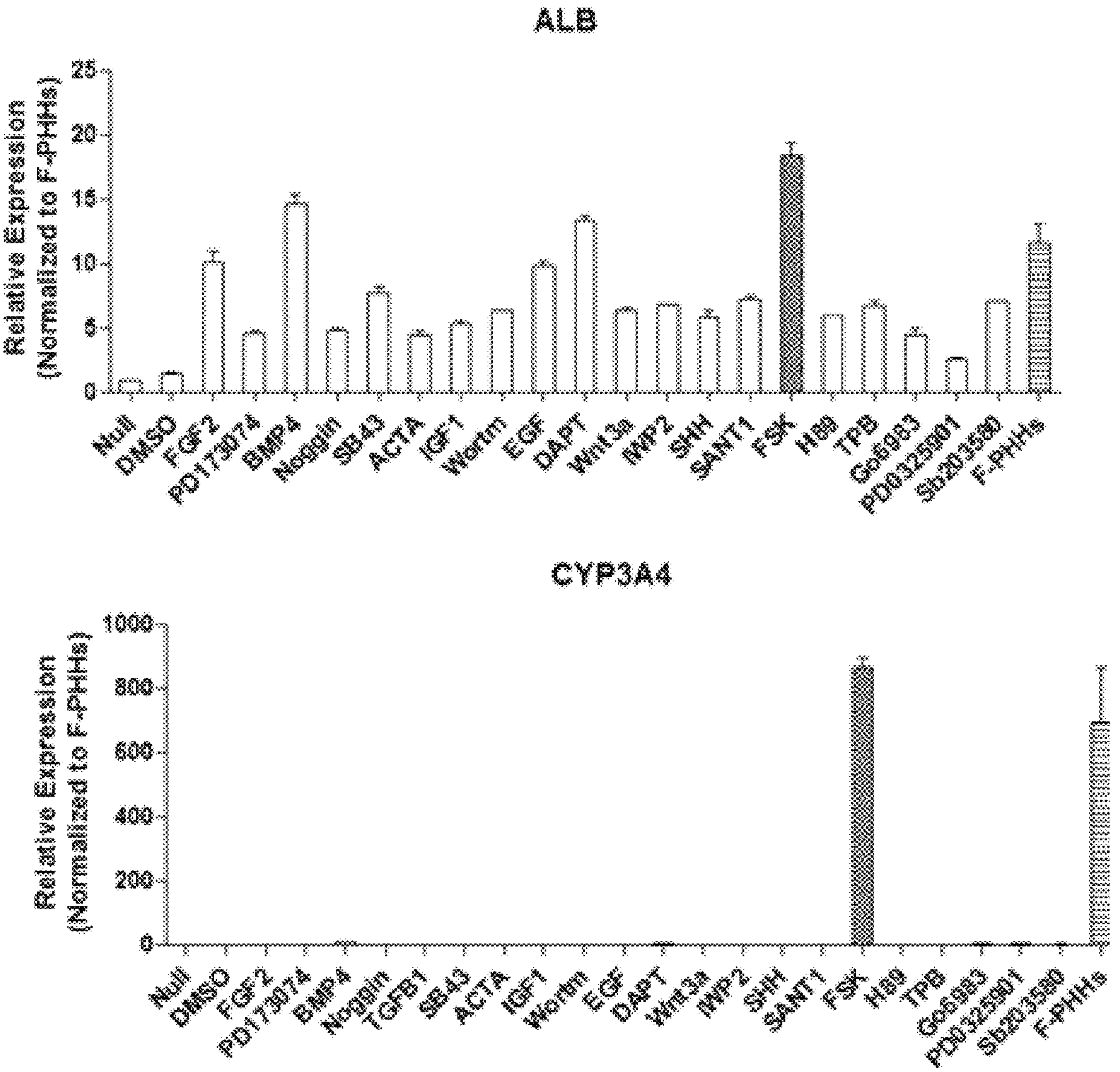
FIGS. 3A and 3B show identification of cAMP activator Forskolin as advantageous to PHH culture in vitro. Screen of a pool of small-molecules for candidates that effectively inhibit the expression of EMT master genes and maintain the expression of key hepatocyte genes. qRT-PCR analysis was performed at day 14 in culture; F-PHHs were used as positive control. Relative gene expression was normalized to Null. n=2.
Figure 3A:
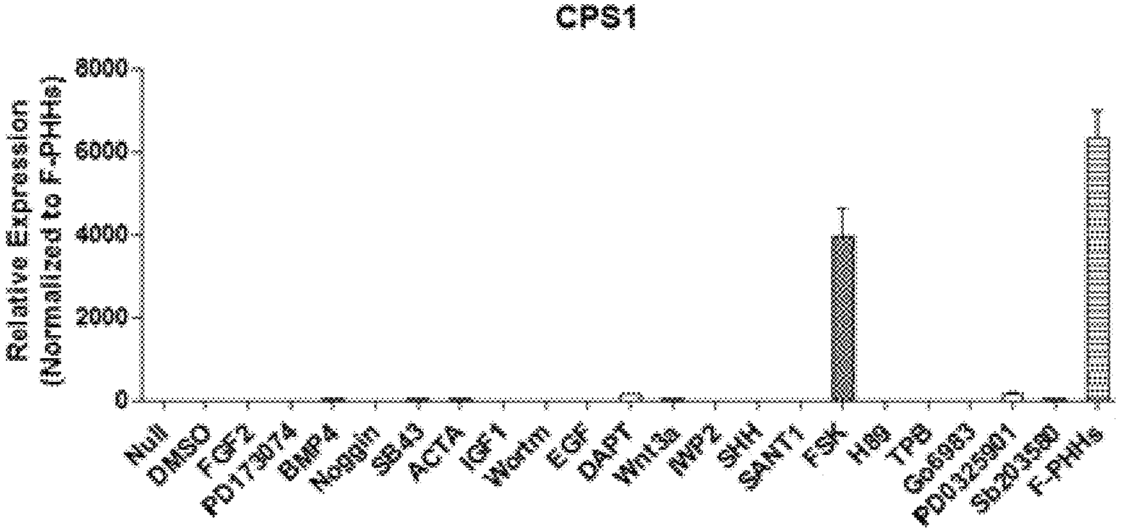
Figure 3A:
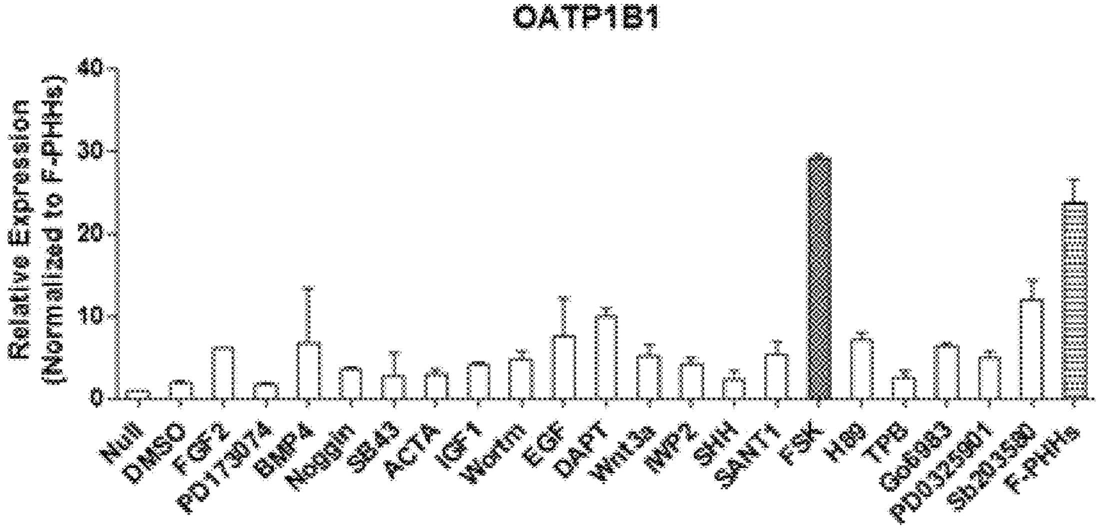
Figure 3B:
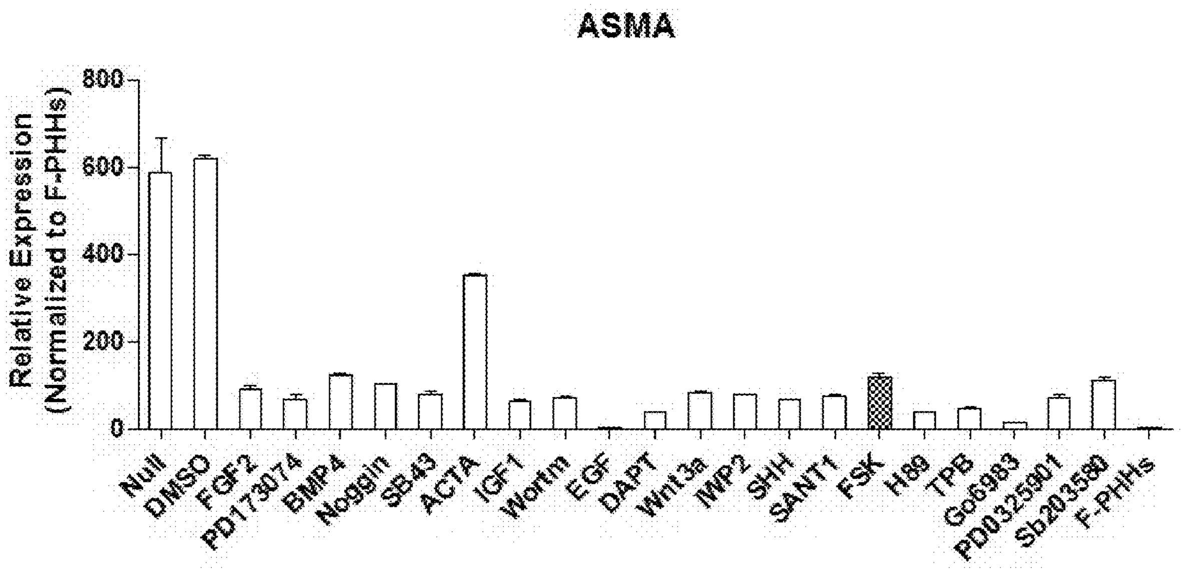
Figure 4A:
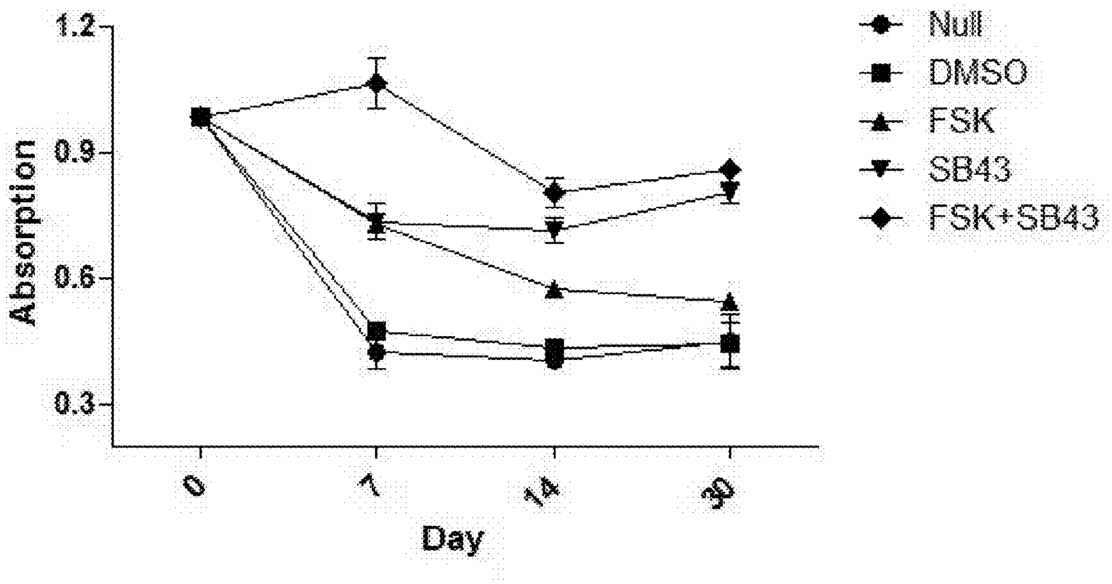
FIGS. 4A-4C show effects of the combination of FSK and SB43 on PHH maintenance.
Figure 4B:
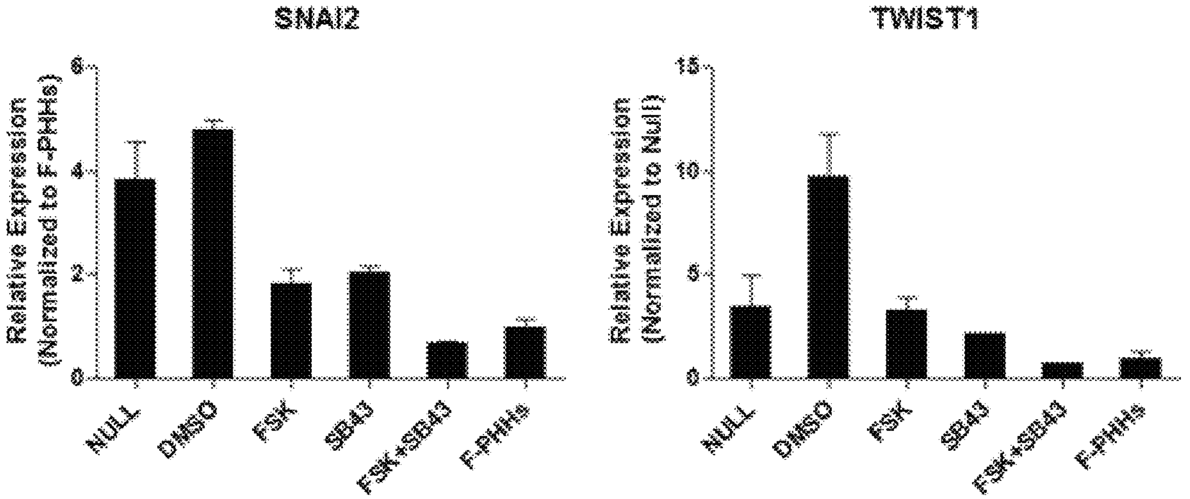
Figure 4C:
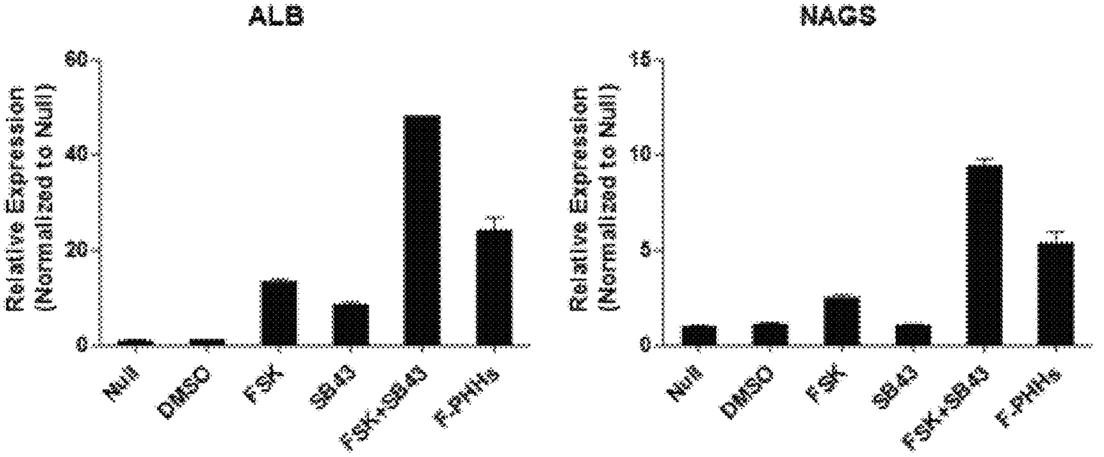
Figure 4C:
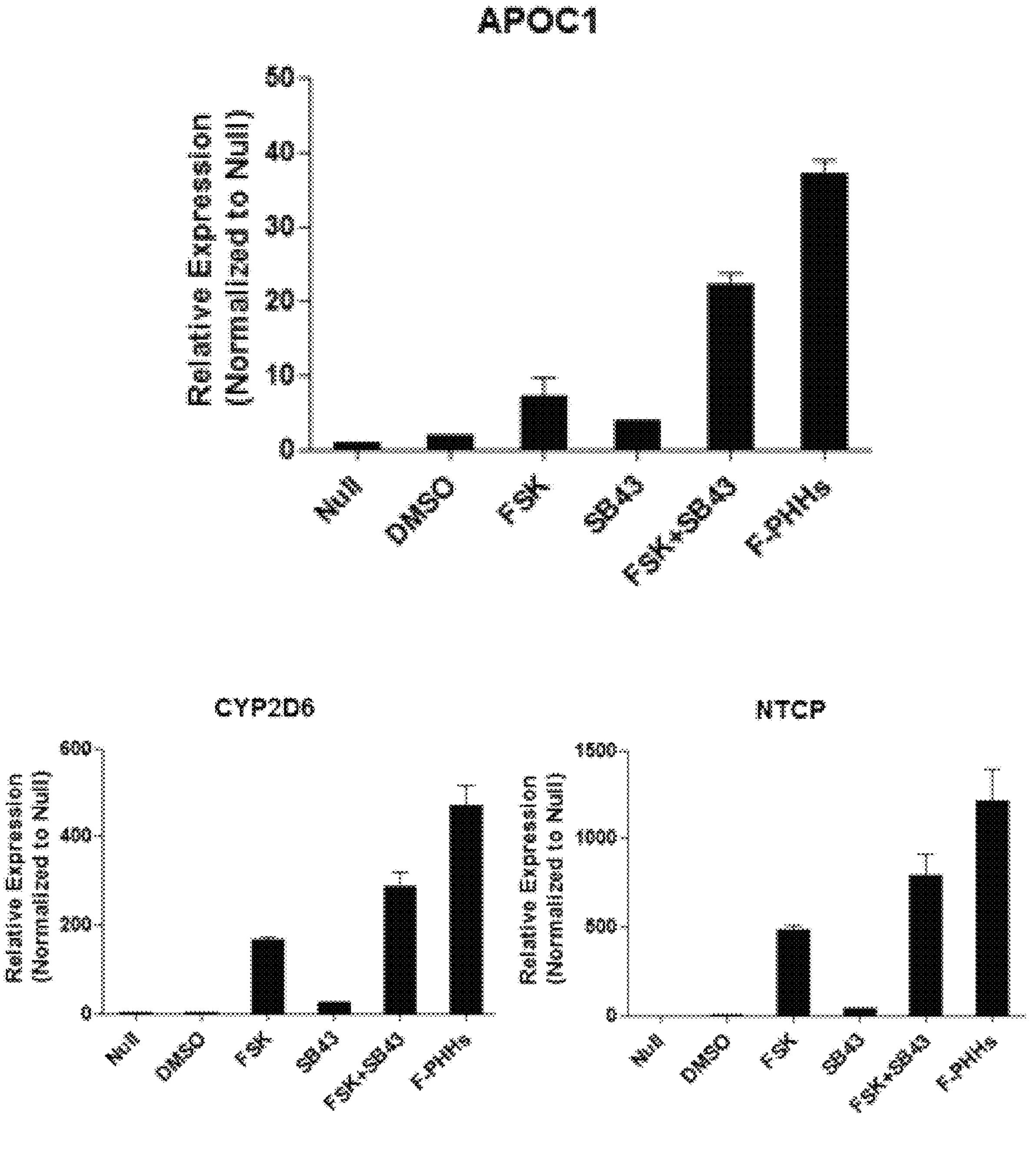
Figure 4D:
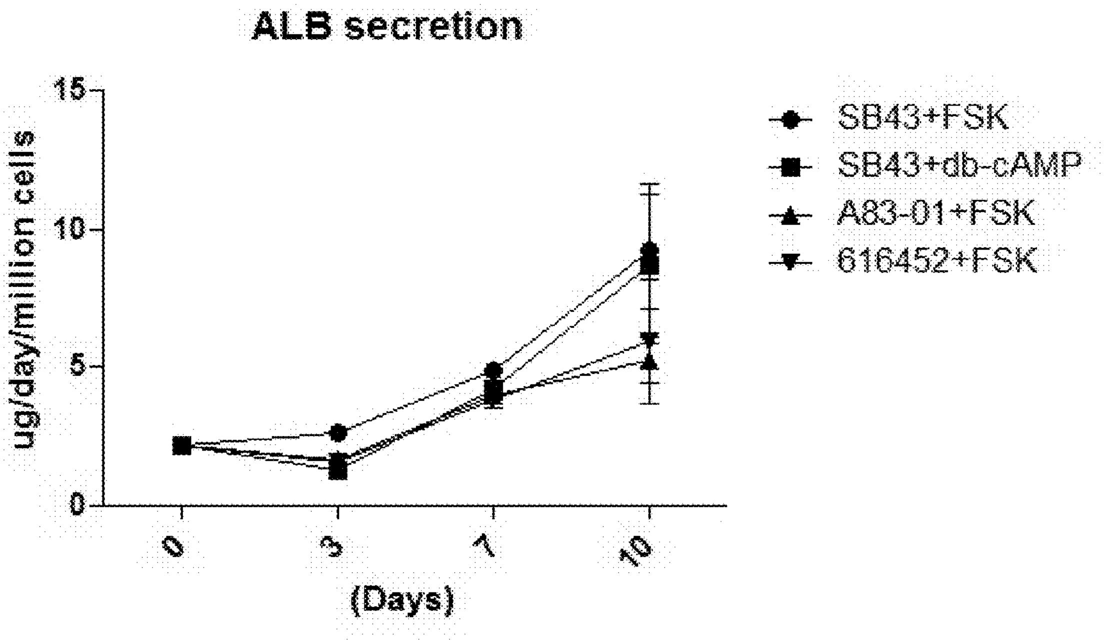
FIG. 4D is a line graph showing ALB secretion dynamics in PHHs cultured under different conditions. n=3 independent batches.

To identify other signaling pathways critical for maintaining functional PHHs, a chemical library of small molecules was screened by adding individual small molecules combined with SB43 to cultured hepatocytes. Forskolin (FSK), an activator of adenylate cyclase (AC), sustained hepatic functional gene expression (ALB; CSP1; CYP3A4; OATP1B1) and down-regulated EMT marker gene expression α-smooth muscle actin (ASMA) (FIGS. 3A and 3B), sustained PHH survival with maintenance of hepatic morphology. Under this two-chemical condition containing FSK and SB43 (herein, "2C"), we observed that hepatocytes exhibited typical hepatic polarized polygonal morphology and rare cell death after two weeks in culture. By contrast, in the absence of FSK and SB43, hepatocytes became morphologically depolarized in two weeks with a poor cell survival in culture PHHs Maintained Under 2C Condition (2C-PHHs) in the Long Term Possess the Functional Characteristics of their Freshly Isolated Counterparts Studies were conducted to test whether the 2C condition could sustain the functions of PHHs in the long term. The expression of a panel of key hepatic functional markers was first evaluated, including liver-synthesized and -secreted serum proteins (ALB and ApoC1), rate-limiting enzymes of nitrogen metabolism (NAGS, CPS1 and OTC), key xenobiotics metabolizing cytochrome P450 (CYP) enzymes (CYP3A4, CYP2D6 and CYP2C9) and transporters (NTCP, MRP2 and BSEP). By RT-qPCR analysis, the expression of these genes was comparable between 2C-PHHs and F-PHHs (FIG. 4B). A broad spectrum of other hepatic functional genes was further analyzed, such as genes involved in the metabolism of amino acid and fatty acids, as well as coagulation. The results showed that the gene expression profile of 2C-PHHs was similar to that of F-PHHs. To further confirm that 2C is functionally independent of basal medium types, 2C was tested with both WME and HCM. RT-qPCR analysis showed that after 4 weeks in culture, 2C-PHHs expressed hepatic genes at a comparable level to F-PHHs with 2C treatment in both HCM and WME (FIG. 4C; bottom panel). This result indicates that 2C worked independently of the type of culture medium, and the following experiments were based on WME. Importantly, FSK in combination with SB43 showed synergistic effects on hepatocyte maintenance (measured as upregulation of expression of ALB; N-acetylglutamate synthase (NAGS), Apolipoprotein C—I (APOC1); CYP2D6; NTCP; and down regulation of SNAI2 and TWIST1 in FSK+SB43 treatment compared FSK or SB43 alone) potentially by activating cAMP (FIG. 4A-D).

Collectively, these data indicate that the 2C condition effectively maintained key hepatic functional gene expressions of long-term cultured PHHs.

Figure 4E:
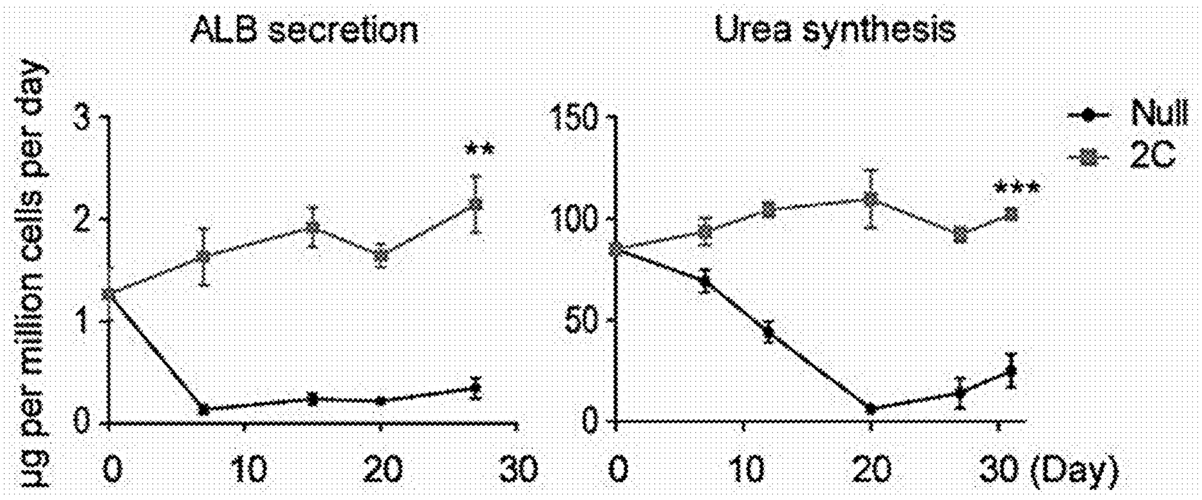
FIG. 4E is a line graph showing albumin secretion and urea synthesis in cultured PHHs. n=2.

Next, the albumin (ALB) secretion, which represents the capacity of protein synthesis and secretion, and urea synthesis, which represents the capacity of nitrogen metabolism in human hepatocytes, was quantified. The secretion of ALB dramatically decreased within a week in hepatocytes without 2C, but was well maintained in 2C-PHHs for about four weeks. Similar results were obtained for urea synthesis. These results were reproducible on the different batches of PHHs (FIG. 4E).

Figure 4F:
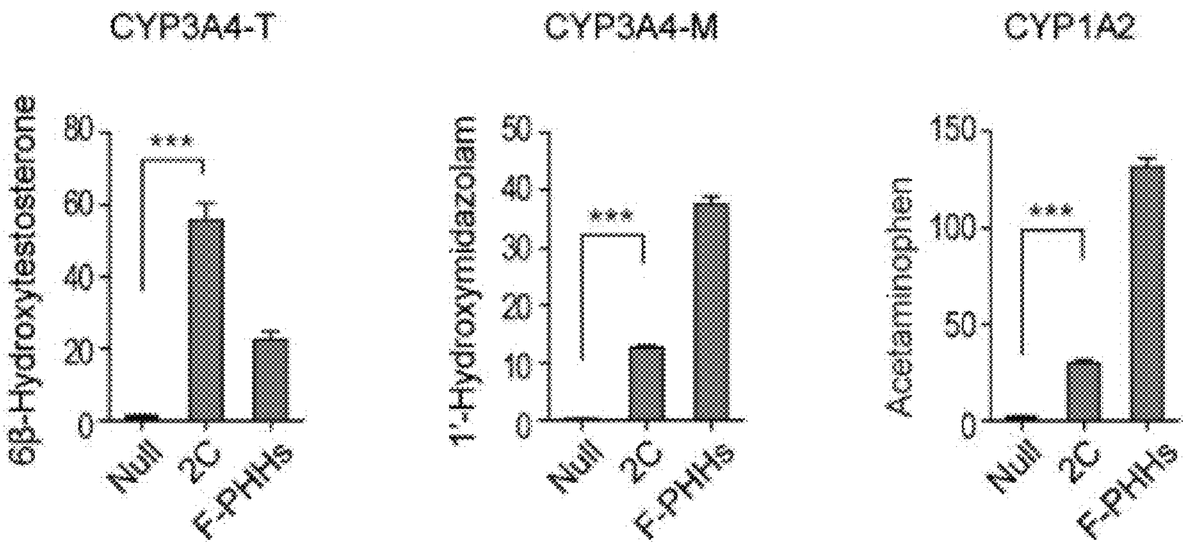
FIG. 4F shows drug metabolizing activities of CYP enzymes in PHHs cultured under different conditions measured by LC/MS. Specific activities of CYP3A4 were measured using testosterone (CYP3A4-T) and midazolam (CYP3A4-M). The results are presented as pmol/min per million cells. n=3.
Figure 4F:
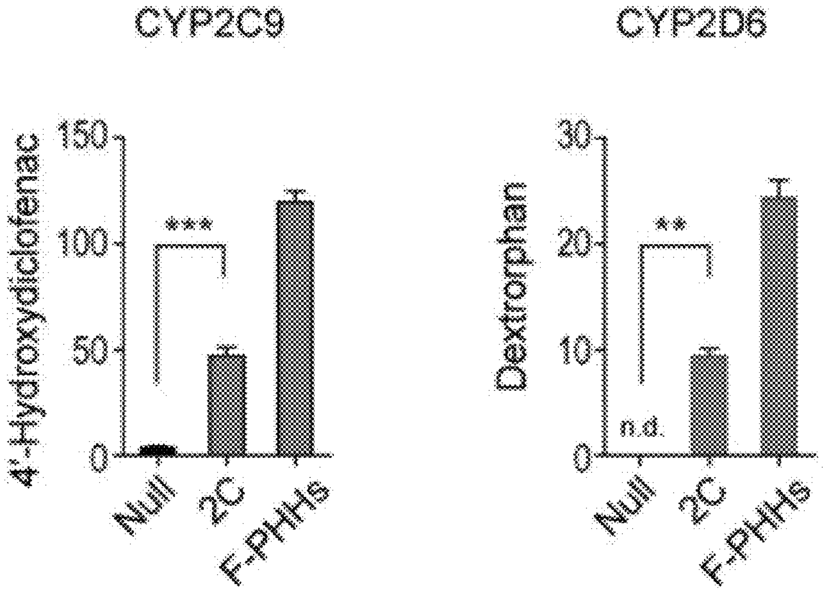
Figure 4G:
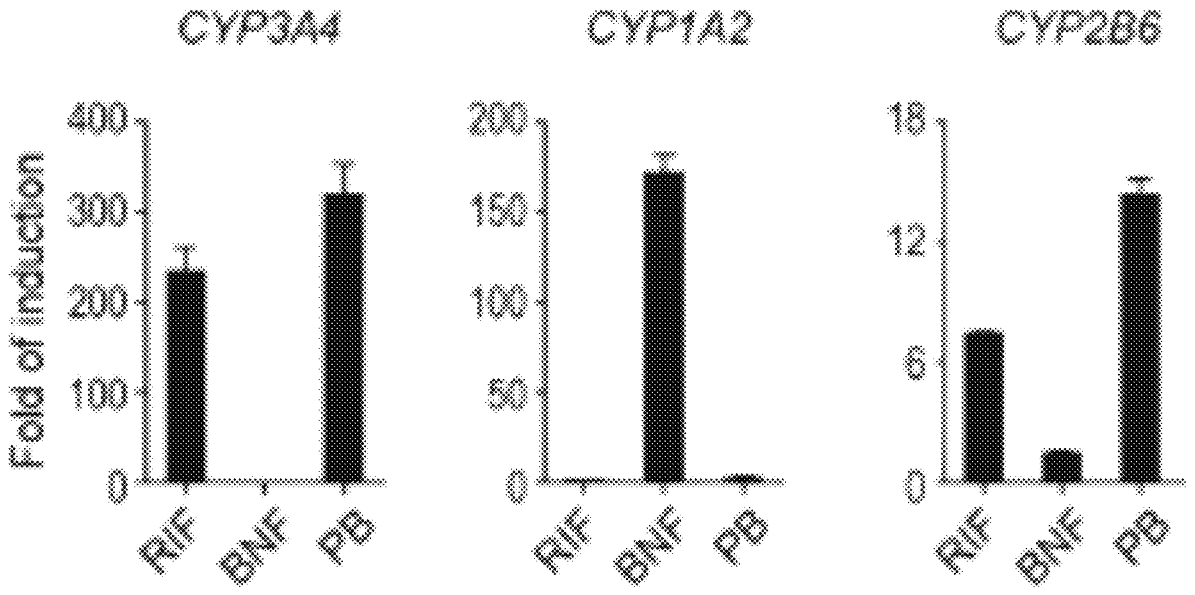
FIGS. 4G-I show induction of CYP450 activities in 2C-PHHs detected by qRT-PCR (FIG. 4G) and LC/MS (FIG. 4H). Rif, Rifampin; PB, Phenobarbital; ETOH, Ethanol; BNF, β-Naphthoflavone. n≥2.
Figure 4H:
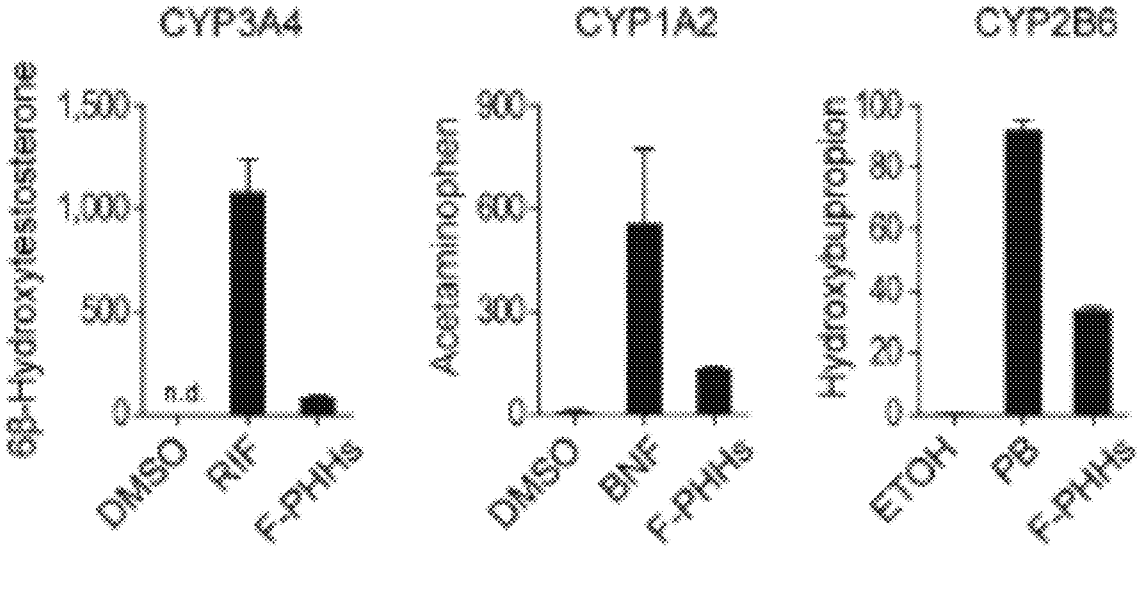
Figure 4I:
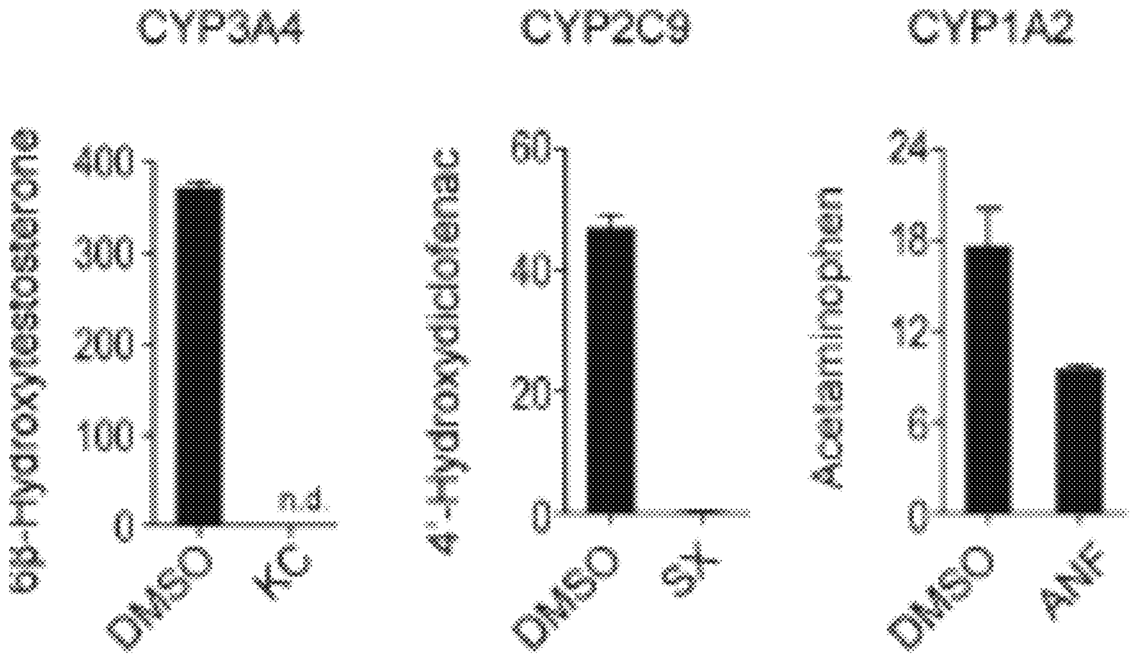
Figure 4J:
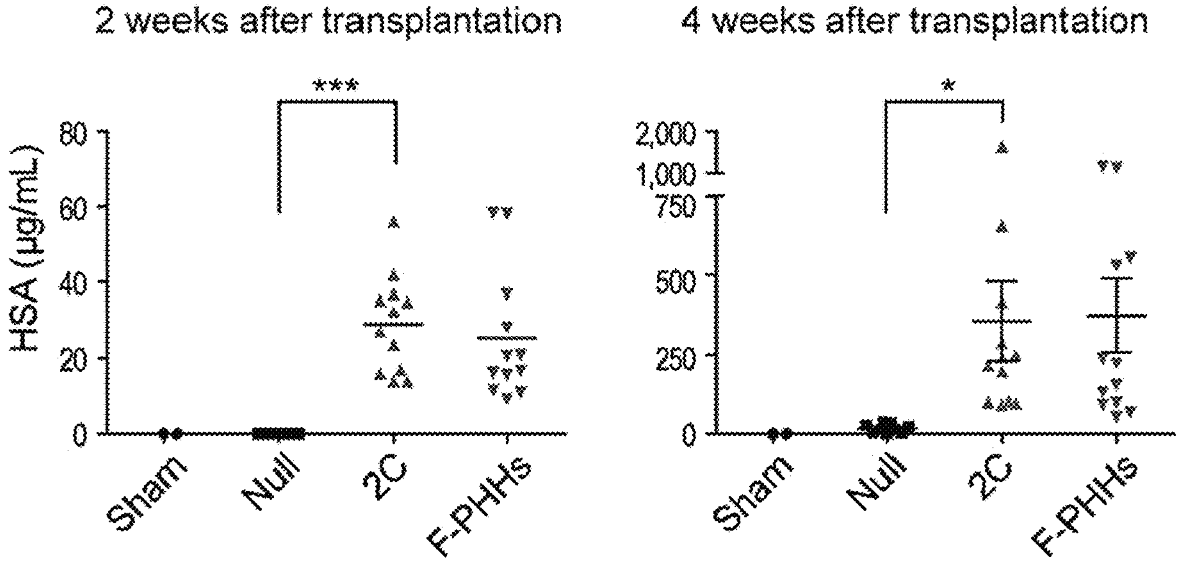
FIG. 4J is the result of an ELISA of human albumin in mouse serum at two and four weeks after transplantation of 4-week cultured PHHs.

The in vivo engraftment ability of 2C-PHHs was tested. After 4 weeks, 2C-PHHs robustly repopulated the recipient mouse liver and secreted human serum albumin (HSA) at the levels comparable to F-PHHs. By contrast, the hepatocytes cultured without 2C poorly repopulated the mouse liver, as indicated by the fact that after 2-week transplantation, HSA could not be detected, and after 4-week transplantation, HSA level was barely detected in contrast with 2C-PHHs (FIG. 4J). Collectively, these data indicated that 2C could support the functional maintenance of PHHs in vitro for at least 4 weeks.

Figure 4K:
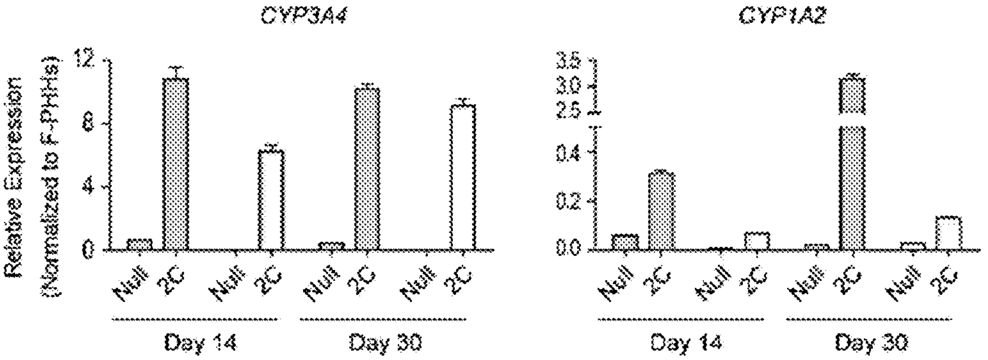
FIG. 4K show expression of major CYP enzymes in PHHs cultured in 2C condition for 14-days and/or 30-days detected by qRT-PCR. Two basal mediums, William's medium E (WME) and HCM were applied. Relative gene expression is normalized to F-PHHs
Figure 4K:
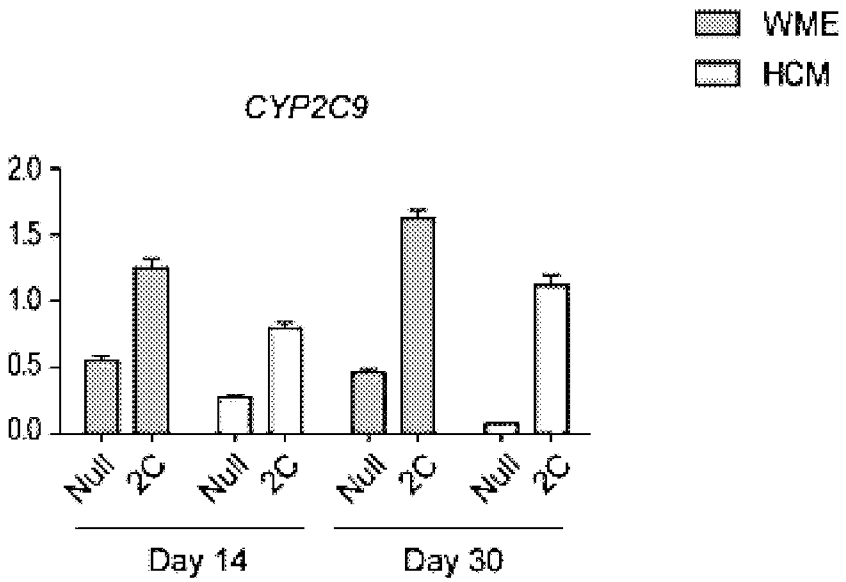
Figure 4K:
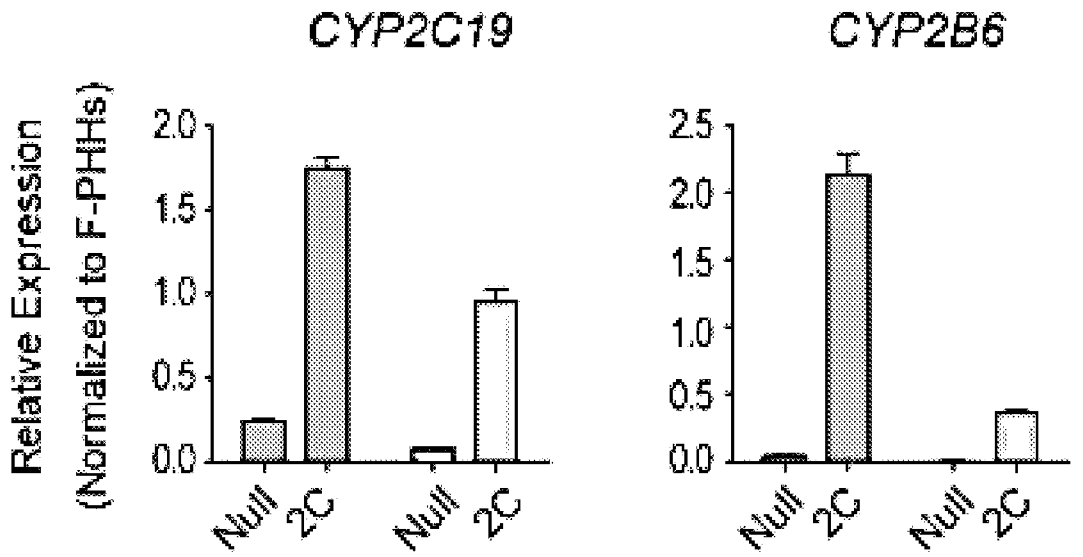
Figure 4K:
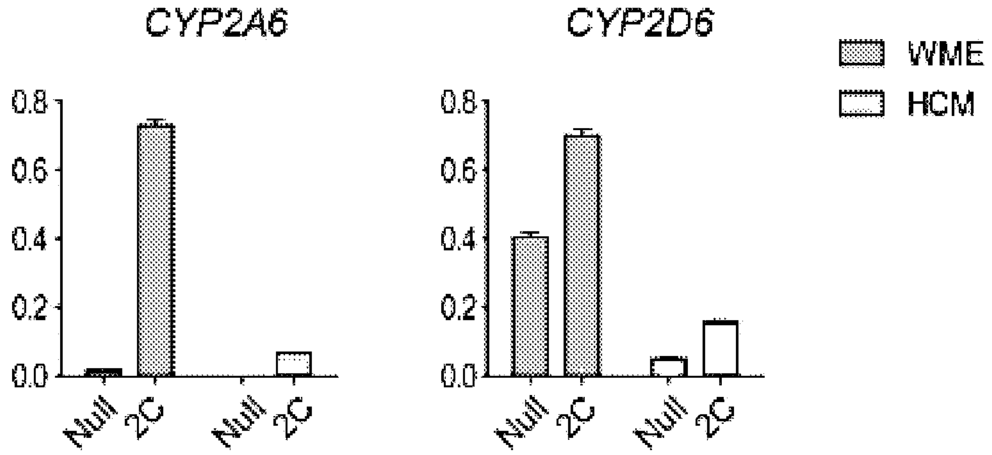

Maintenance of the Drug Metabolizing Ability of Cultured Hepatocytes in 2C Condition To evaluate the drug metabolizing ability of 2C-PHHs, the expression of key CYP enzymes was quantified by RT-qPCR. After one month in culture, the expression of CYP3A4, CYP1A2, CYP2C9, CYP2D6, CYP2B6 and CYP2C19 in 2C-PHHs was comparable to that of F-PHHs (FIG. 4K). To further evaluate the drug metabolizing activities, a liquid chromatography mass spectrometry (LC/MS) assay was used. The data showed that after one month culture, the metabolizing activities of CYP3A4, CYP2D6, CYP2C9 and CYP1A2 in 2C-PHHs, responsible for over 80% of human drug oxidation were comparable to those of F-PHHs, while hepatocytes cultured without 2C lost these metabolizing activities (FIG. 4F).

Further experiments were conducted to test whether 2C-PHHs could be applied to predict drug-drug interaction (DDI). The potent CYP enzyme inhibitors and inducers commonly used in DDI testing were applied (Baranczewski et al., PR, 58:453-472, (2006)), and the results showed that 2C-PHHs effectively responded to these inhibitors and inducers (FIGS. 4G, 4H and 4I). The drug-metabolizing activities of 2C-PHHs were dramatically suppressed by specific inhibitors of the CYP enzyme (FIG. 4I). Additionally, after one month culture, the gene expression level and metabolizing activities of the three major CYP enzymes, CYP3A4, CYP1A2 and CYP2B6, in 2C-PHHs were well responsive to the specific inducers (FIGS. 4G and 4H). Collectively, these data suggest that 2C could support the maintenance of drug metabolizing activities of PHHs in vitro.

Maintenance of Cryopreserved Recovered Hepatocytes by 2C with Additional Small Molecules Considering that 2C enabled a robust functional maintenance of PHHs for a long time, we then tested whether 2C could support the maintenance of cryopreserved primary human hepatocytes (Cryo-PHHs), which are major resources of human hepatocytes in applications. However, Cryo-PHHs are more difficult to stably maintain in vitro due to poor viability and functionality, which is caused by the process of cryopreservation (Donato et al., Current Drug Metabolis, 9:1-11 (2008b); Terry et al., Mol. Cell Transplantation, 16:639-647 (2017)). Under the 2C condition, we observed an improved survival of cultured Cryo-PHHs. However, they lost polygonal morphology after 4 weeks in culture (data not shown), suggesting EMT occurred in 2C-treated Cryo-PHHs.

Figure 5A:
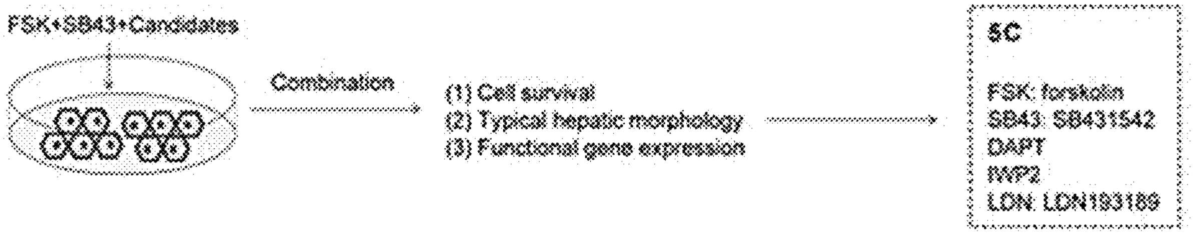
FIGS. 5A-5E show identification of the optimal configuration (5C condition) for maintaining PHHs.
Figure 5B:
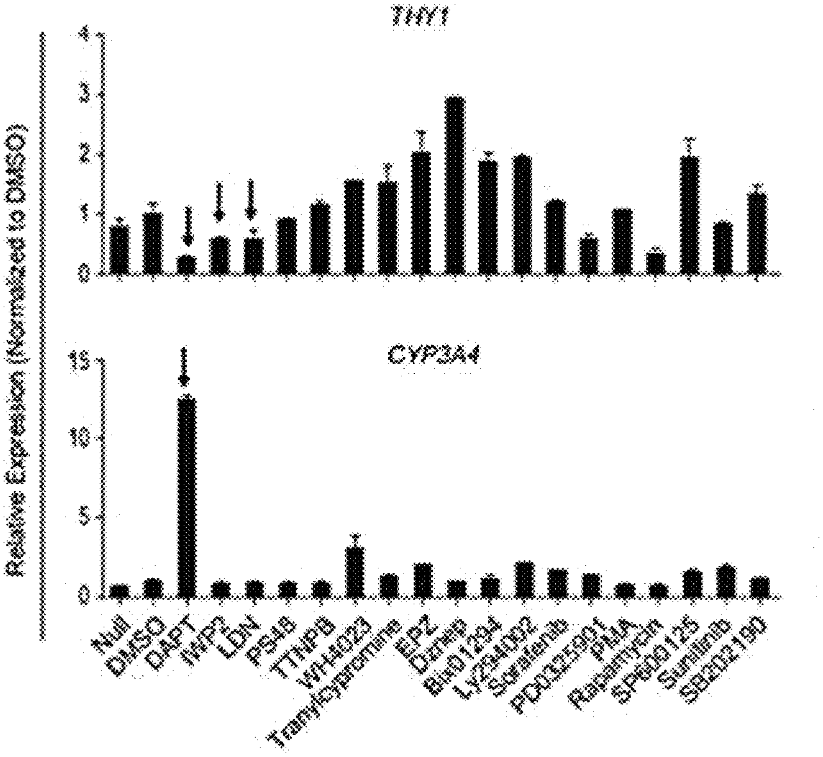
Figure 5B:
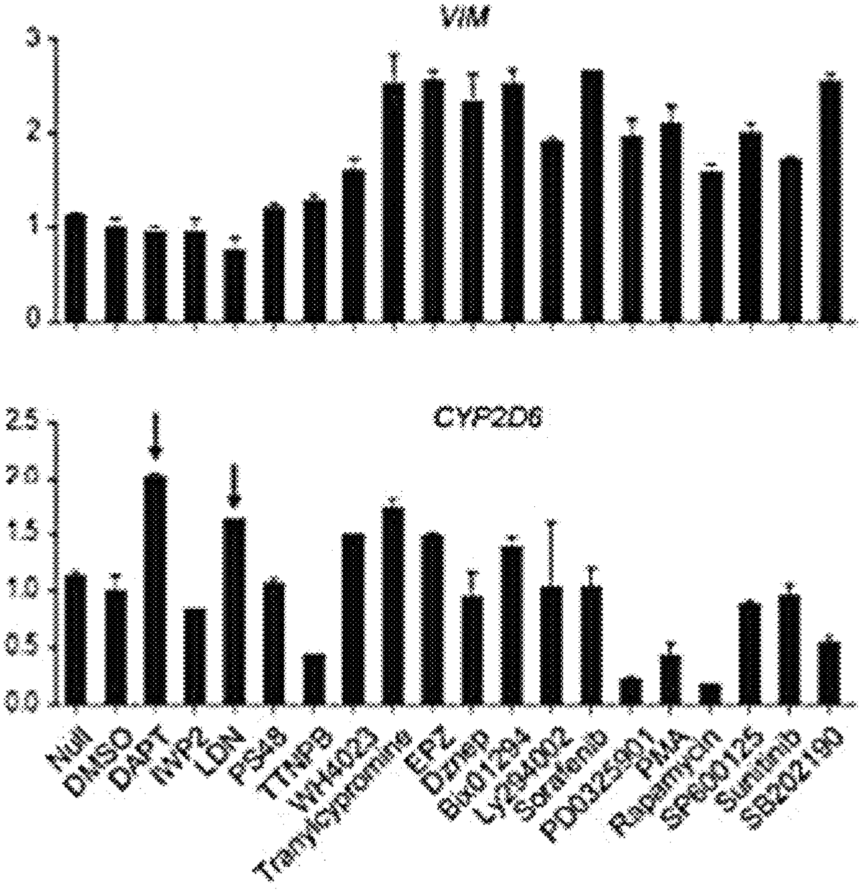
Figure 5C:
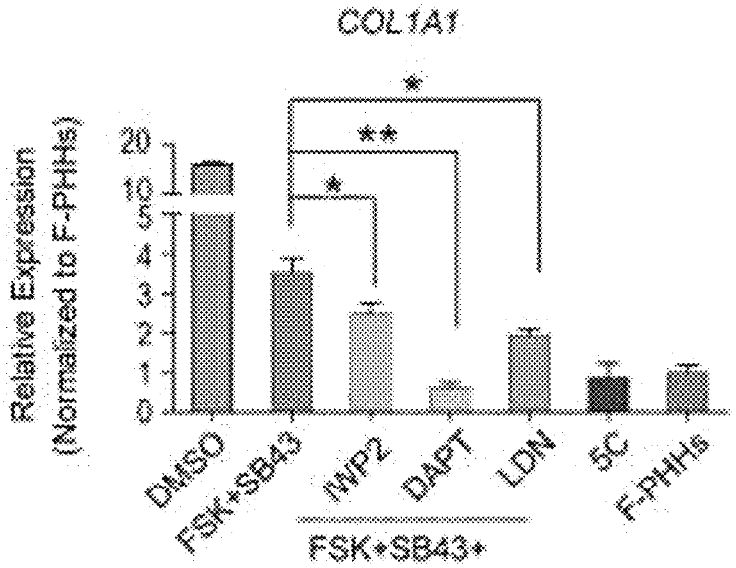
Figure 5D:
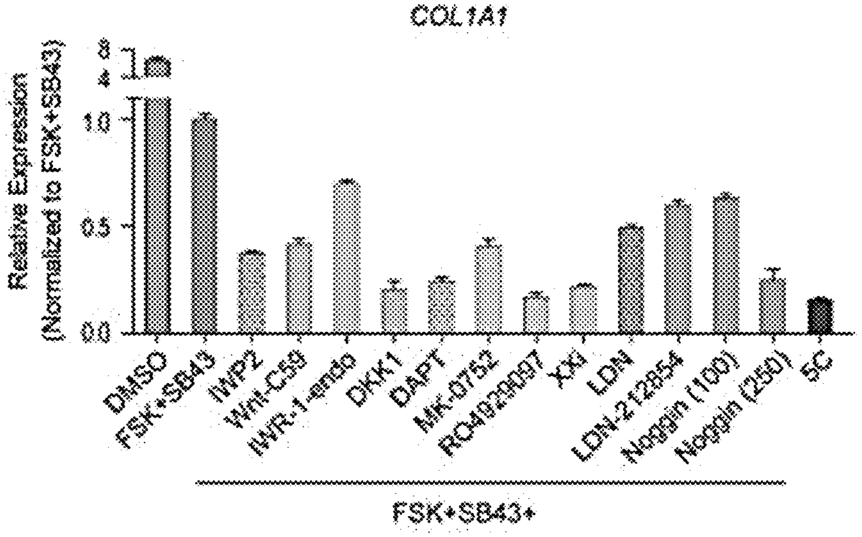
Figure 5D:
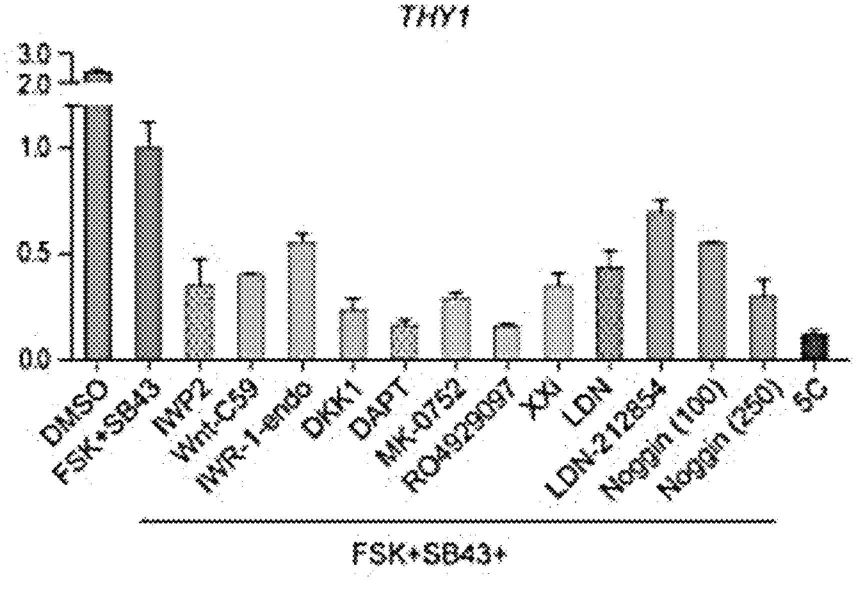
Figure 5E:
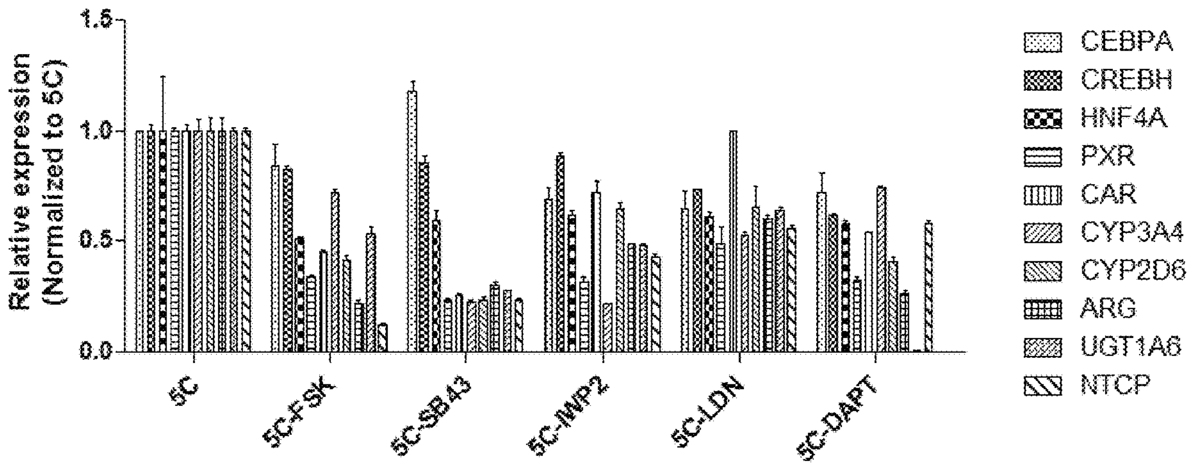
Figure 6A:
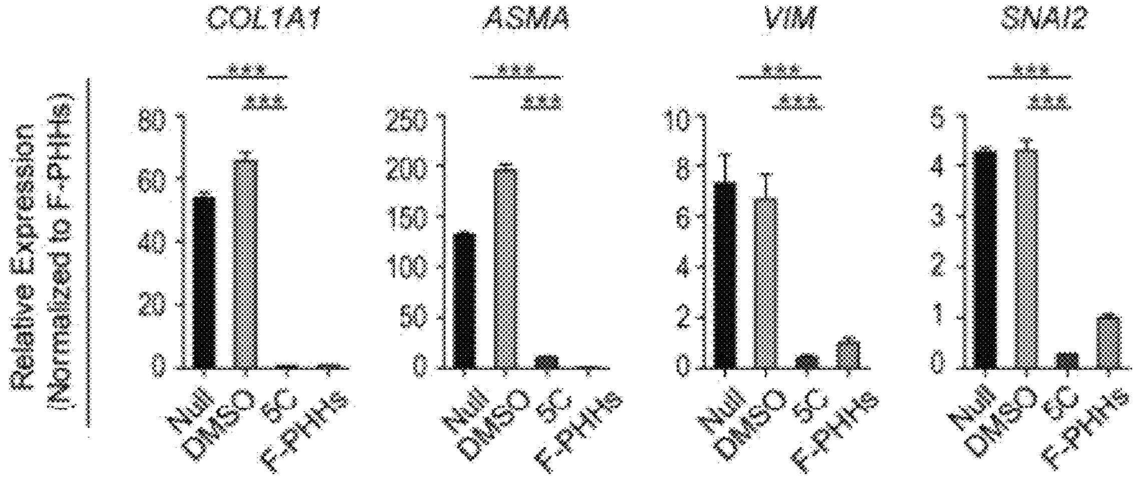
FIG. 6A shows qRT-PCR analysis for mesenchymal marker genes of cryo-PHHs cultured in hepatocyte culture medium (Null) and the 5C culture condition (5C) for 2 weeks. DMSO was used as vehicle control. n=3. Similar results were obtained in 3 independent batches.
Figure 6B:
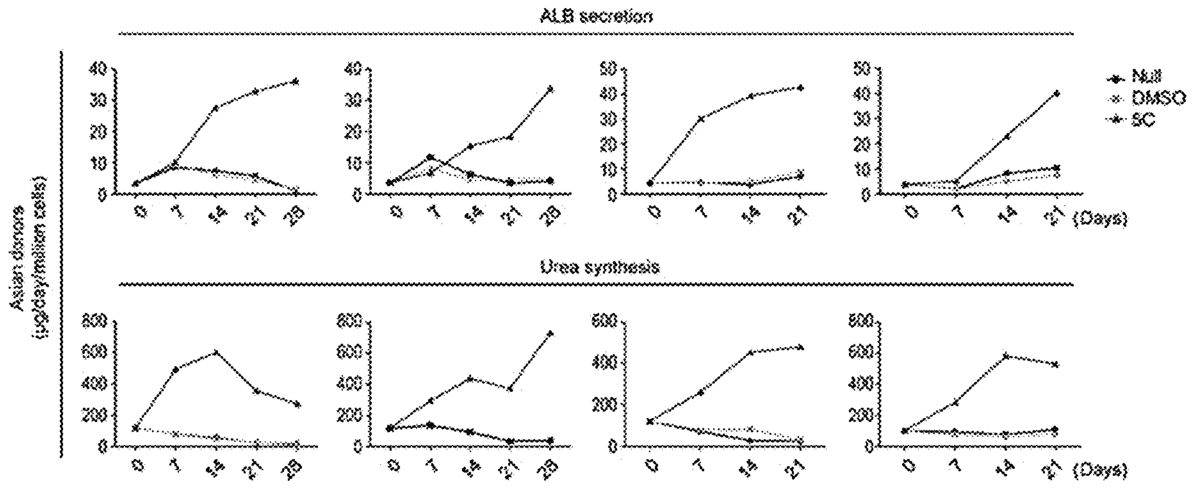
FIGS. 6B and 6C show time-course analysis of human albumin secretion and urea synthesis of freshly isolated PHHs from Asian donors (FIG. 6B) and recovered cryopreserved PHHs from Caucasian donors (FIG. 6C) maintained in 5C and control conditions. n=3.
Figure 6C:
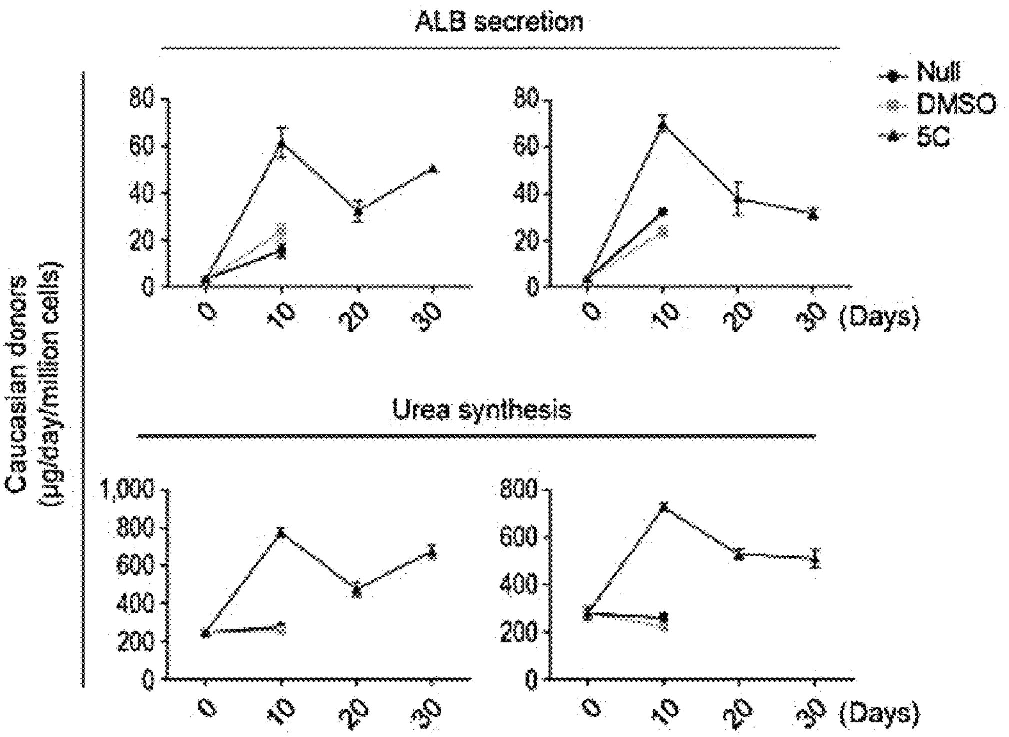
Figure 6D:
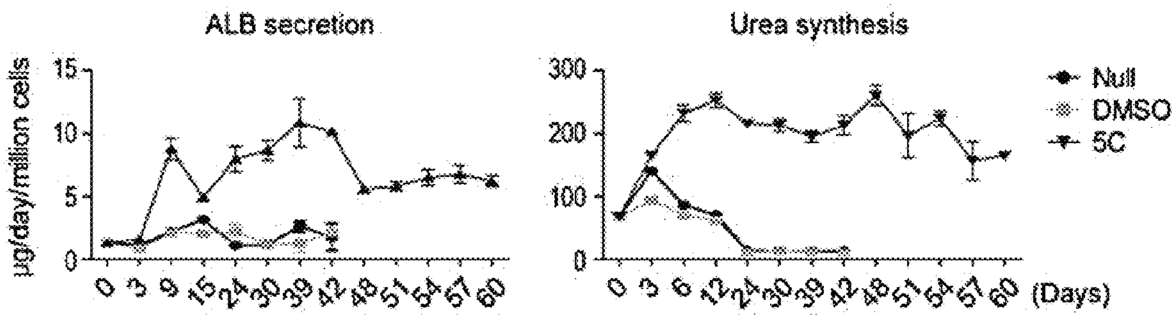
FIGS. 6D and 6E show studies on 5C supported PHH maintenance for over 2 months.
Figure 6E:
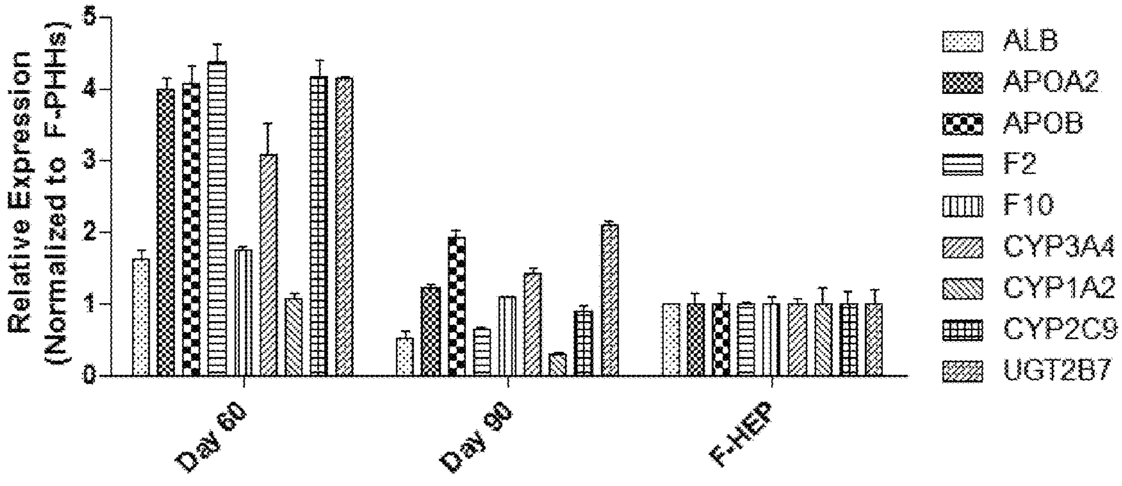

Based on this SB43 and FSK combination, a further chemical screening was performed, and it showed that DAPT (Notch inhibitor), IWP 2 (Wnt inhibitor) and LDN193189 (BMP inhibitor) further blocked the expression of EMT marker genes (Collagen type I alpha 1 (COL1A1); thymus cell antigen 1 (Thy1); Vimentin (VIM)) (FIG. 5A-C). Notably, small molecules or cytokines targeting the same signaling pathways resulted in similar suppression of EMT genes (FIG. 5D). This minimal condition consisting of the five chemicals (5C) FSK, SB43, DAPT, IWP 2 and LDN193189 effectively blocked the expression of EMT genes in cultured cryopreserved primary human hepatocytes (Cryo-PHHs) (FIGS. 6A and 5E) (the expression of COL1A1, a typical biomarker of mesenchymal, was effectively down-regulated after 5C treatment) and supported the maintenance of the typical polygonal shapes of both F-PHHs and Cryo-PHHs for 4 weeks (data not shown). Moreover, 5C cultured PHHs (5C-PHHs) expressed surrogate hepatic functional markers (ALB, AAT (Alpha 1-antitrypsin), CPS1, CYP3A4; CYP1A2) with polarization after 4 weeks culture, measured as deposition of CDFDA at the cell-cell boundary (data not shown) Albumin secretion and urea synthesis in 5C-PHHs were also maintained for at least 3 weeks, reproducible on 9 batches of PHHs (FIG. 6B-6E). Interestingly, batches of PHHs that have high viability could be functionally maintained for 2 months under the 5C condition.

Figure 7:
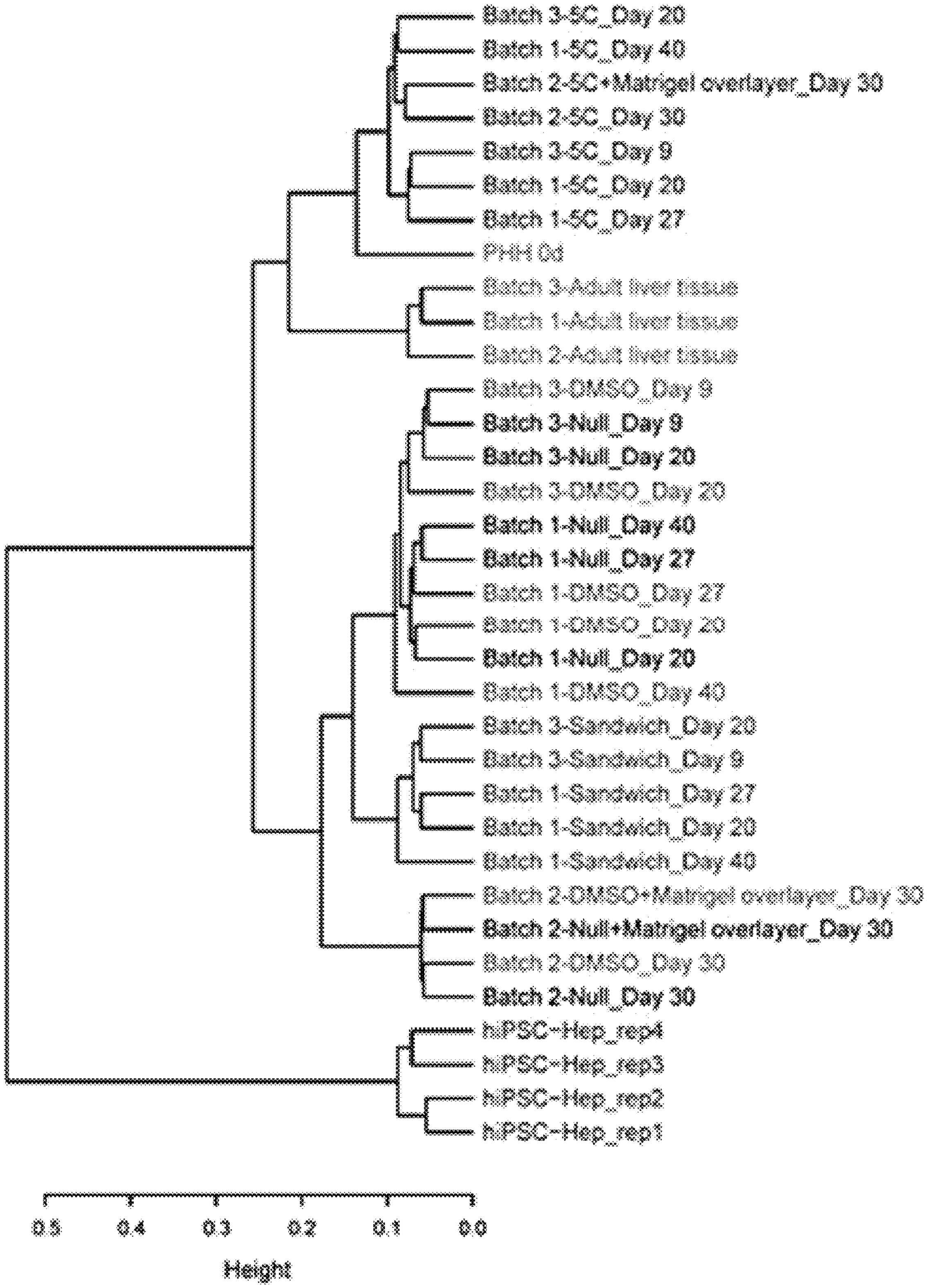
FIG. 7 shows hierarchical clustering to compare the global gene expression profiles of PHHs cultured under different conditions, hepatocytes derived from pluripotent stem cells (hiPSC-Hep_rep1/2/3/4), freshly isolated human hepatocytes (PHH Od) and adult liver tissues. Three independent batches of PHHs were applied and corresponding adult liver tissues were used as the positive control. The expression profiles of PHH Od and hiPSC-Hep_rep1/2/3/4 were RNA-seq data obtained from Gao et al., *Stem Cell Reports* 9, 1813-1824 (2017).
Figure 8A:
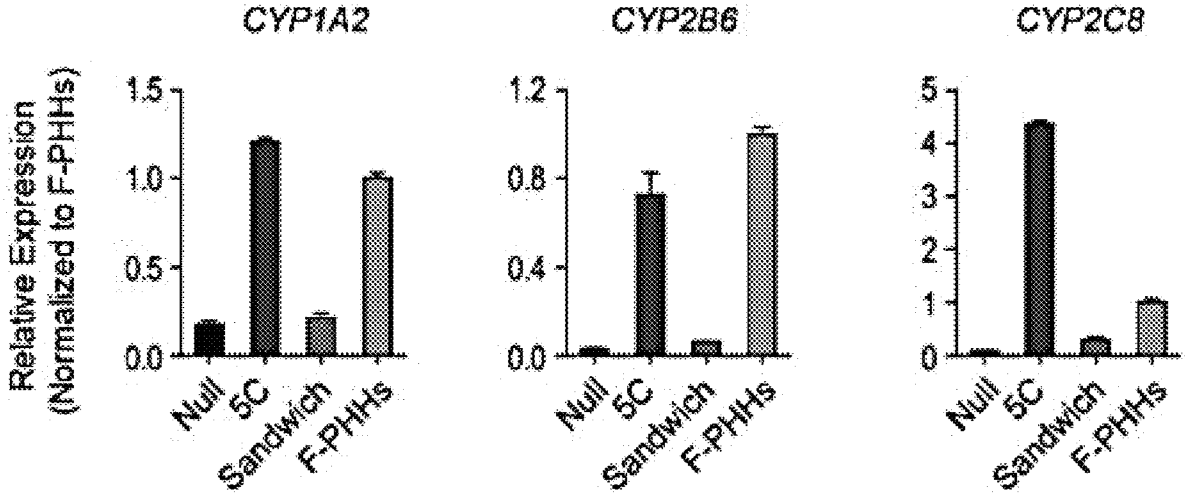
FIG. 8A shows gene expression analysis of hepatic surrogate functional markers and mesenchymal marker in 5C-PHHs and PHHs maintained under sandwich culture by qRT-PCR. qRT-PCR analysis was performed at day 15. Relative expression level was normalized to F-PHHs. n=2.
Figure 8A:
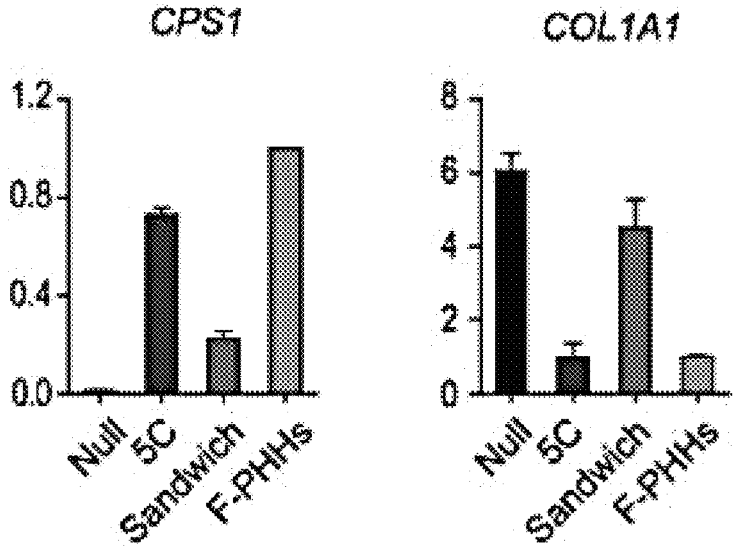
Figure 8B:
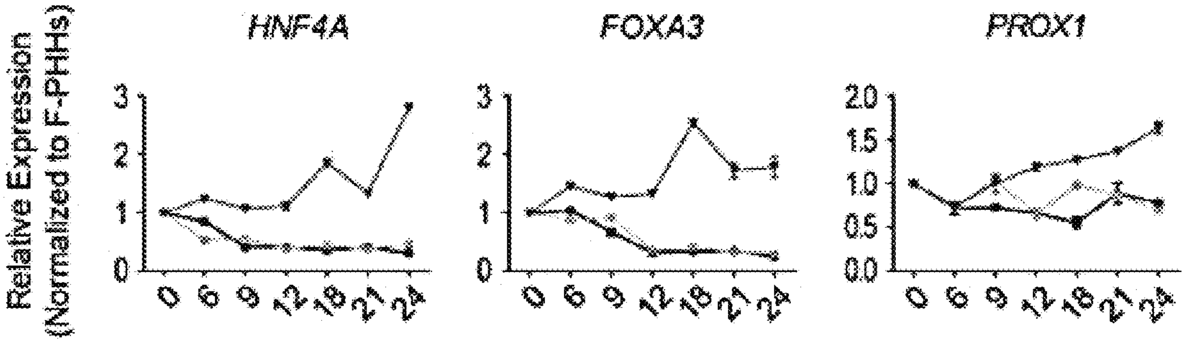
FIG. 8B shows gene expression analysis of hepatic transcription factors by qRT-PCR. Relative expression level was normalized to F-PHHs. n=2. Similar results were obtained in 2 independent batches.
Figure 8B:
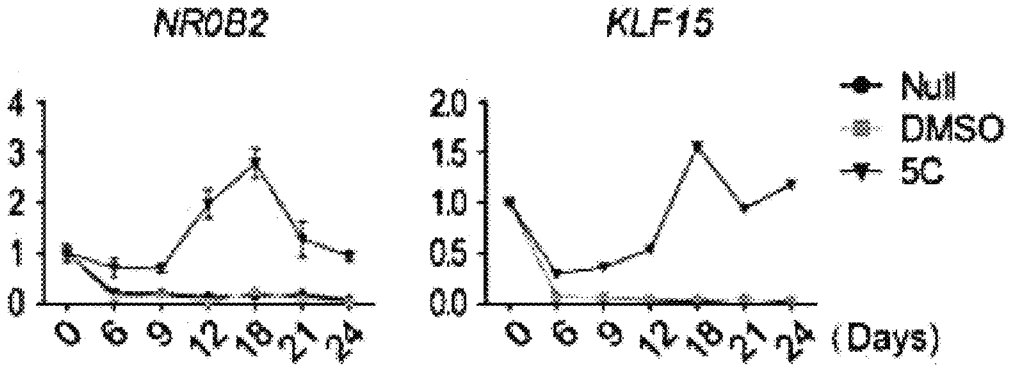
Figure 8C:
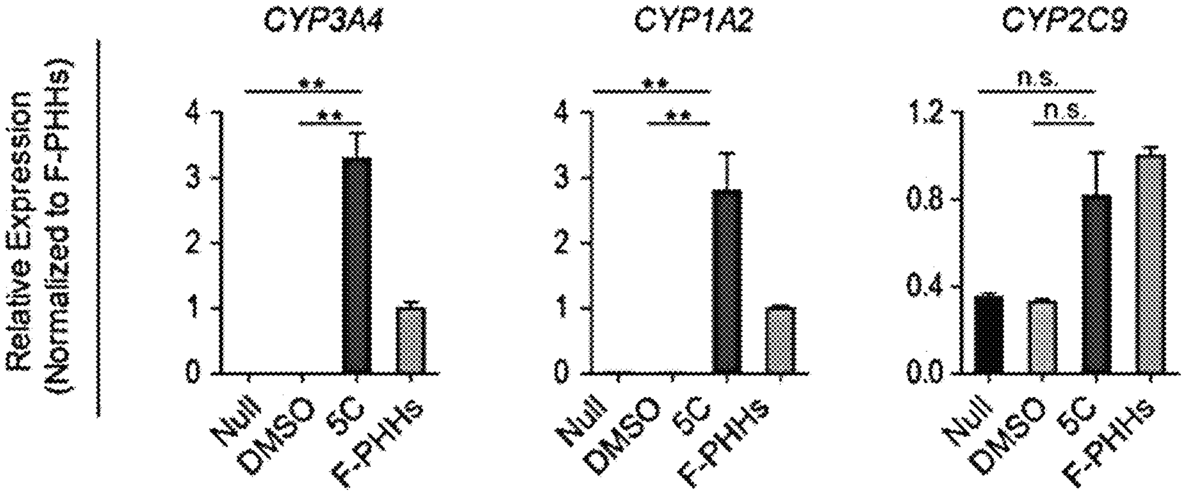
FIG. 8C shows the effect of 5C on the drug-metabolizing activities of cultured human hepatocytes, in vitro measured as gene expression analysis for five core CYP450 enzymes by qRT-PCR after 4 weeks culture. n=3.
Figure 8C:
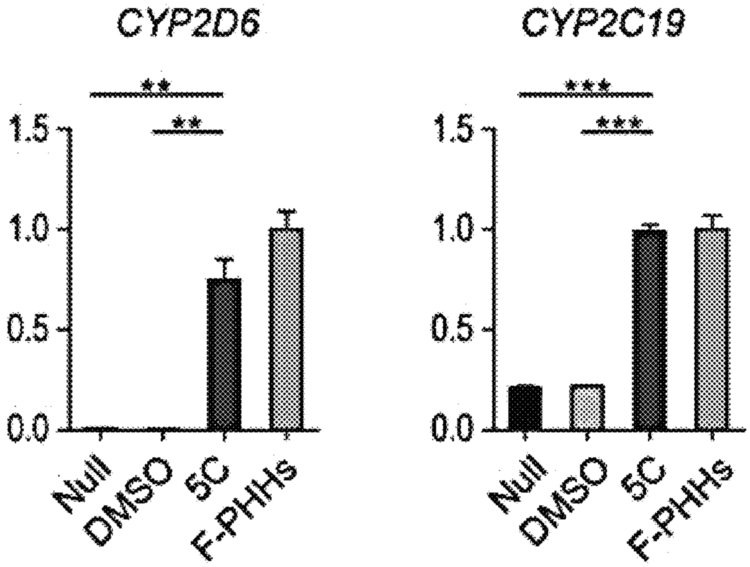

A time-course analysis of global gene expression profiling was next performed by RNA-Seq for 5C-PHHs over the course of one month from isolation. The sandwich culture approach (i.e., culture of hepatocytes between two layers of gelled collagen), an often-used hepatocyte culture condition (Dunn, et al., *Biotechnol. Prog.,* 7:237-245 (1991)), was similarly analyzed for comparison. Hierarchical clustering illustrated that with prolonged culture after 12 hours, only 5C-PHHs were clustered with F-PHHs, whereas the transcriptomes of PHHs in sandwich culture resembled that of the Null and DMSO groups. Of note the sandwich culture was not combined with 5C. The capacity of the 5C condition in supporting global hepatic gene expression was reproducible on another three independent batches of PHHs (FIG. 7). Additionally, qRT-PCR analysis further confirmed that the 5C condition, compared with sandwich approach, was more effective in maintaining the expression of surrogate hepatocyte functional markers and suppressing the expression of mesenchymal marker gene (FIG. 8A). Furthermore, 5C efficiently maintained the expression of transcription factors playing key roles in hepatocyte function (FIG. 8B). Collectively, these results indicated that the 5C condition was able to maintain the global gene expression pattern of human hepatocytes in vitro long-term.

Figure 8D:
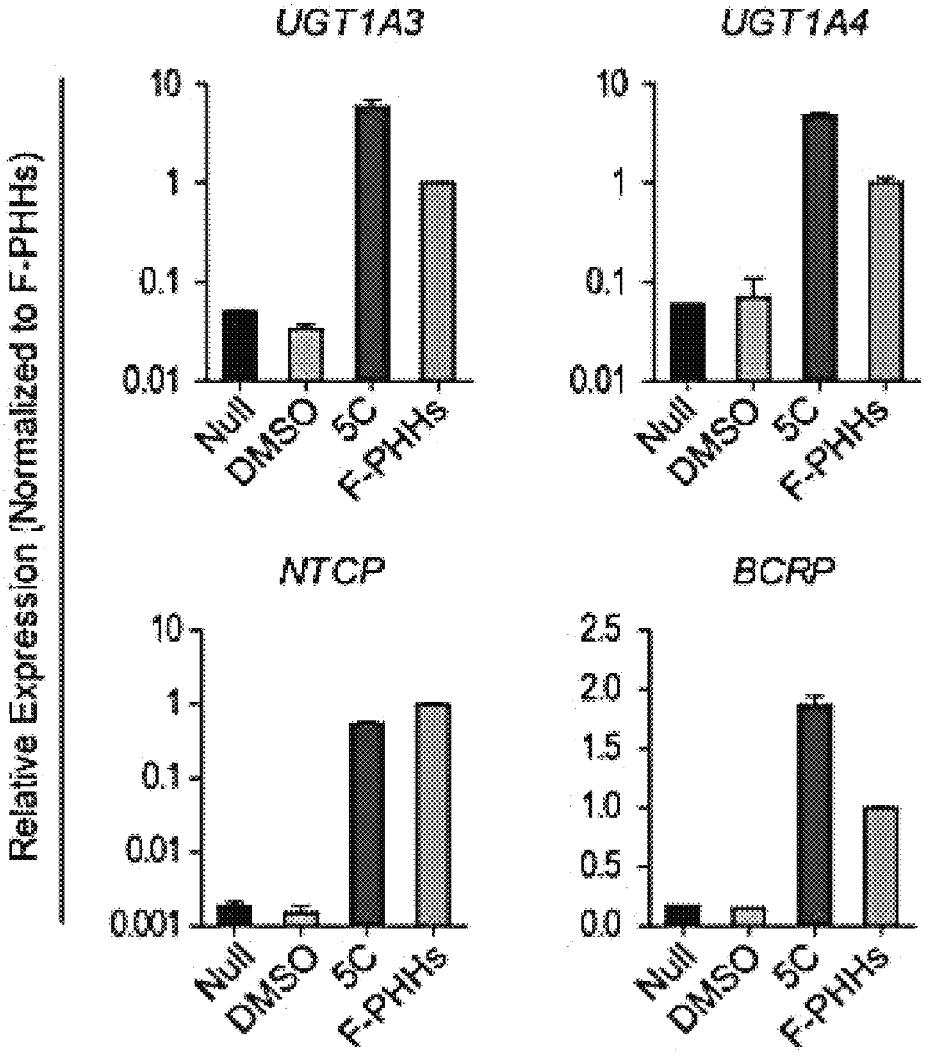
FIG. 8D shows qRT-PCR analysis of the major Phase II enzymes and Phase III transporters in 5C-PHHs after 4 weeks culture. Relative expression level was normalized to F-PHHs. n=2. Similar results were obtained in at least 3 independent batches.
Figure 8D:
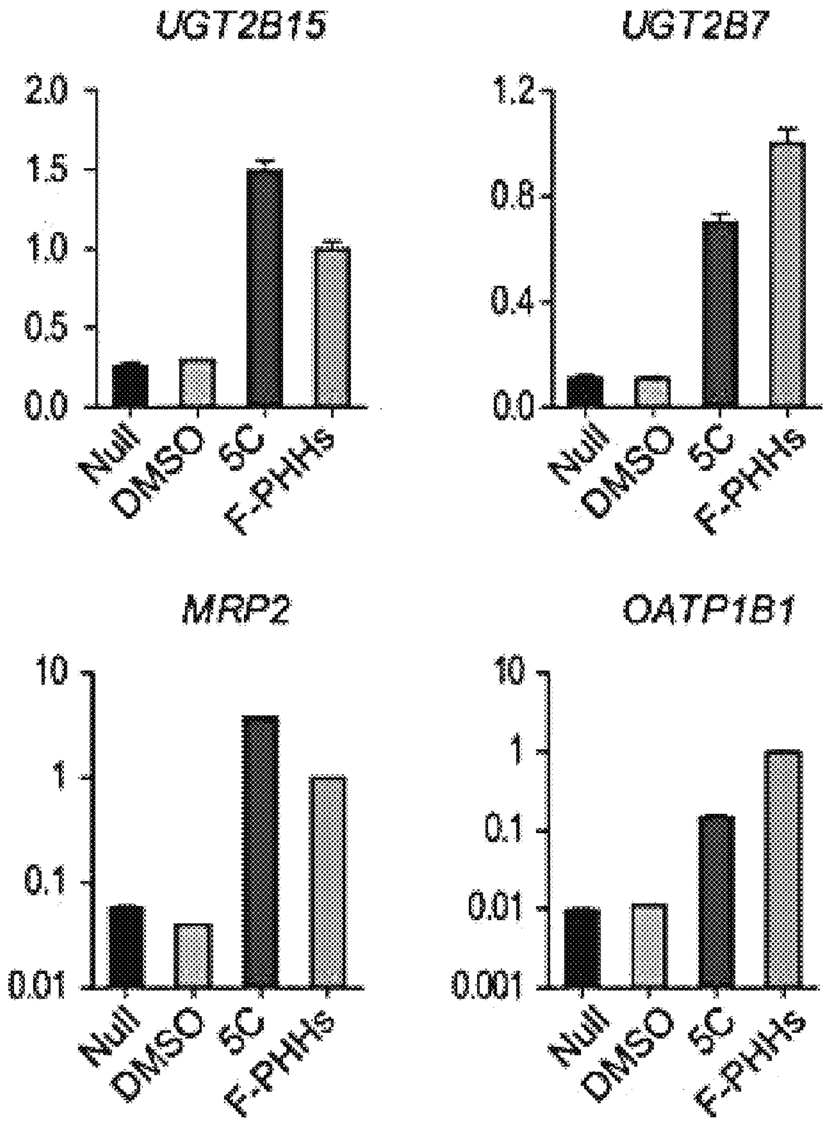
Figure 8E:
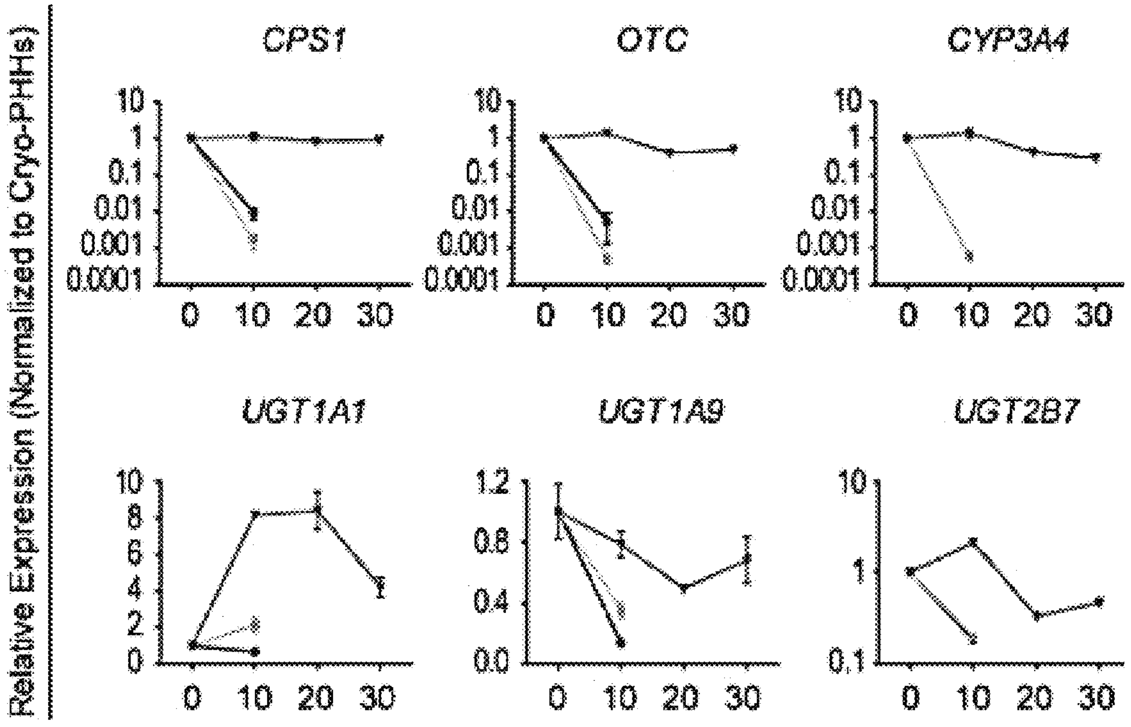
FIG. 8E shows dynamic gene expression analysis of drug metabolism associated genes by qRT-PCR in Cryo-PHHs under different conditions. Recovered cryopreserved PHHs showed severe cell death after 1 week of culture in control conditions (Null and DMSO), thus no data is presented after Day 10. Relative gene expression was normalized to Cryo-PHHs. n=2.
Figure 8E:
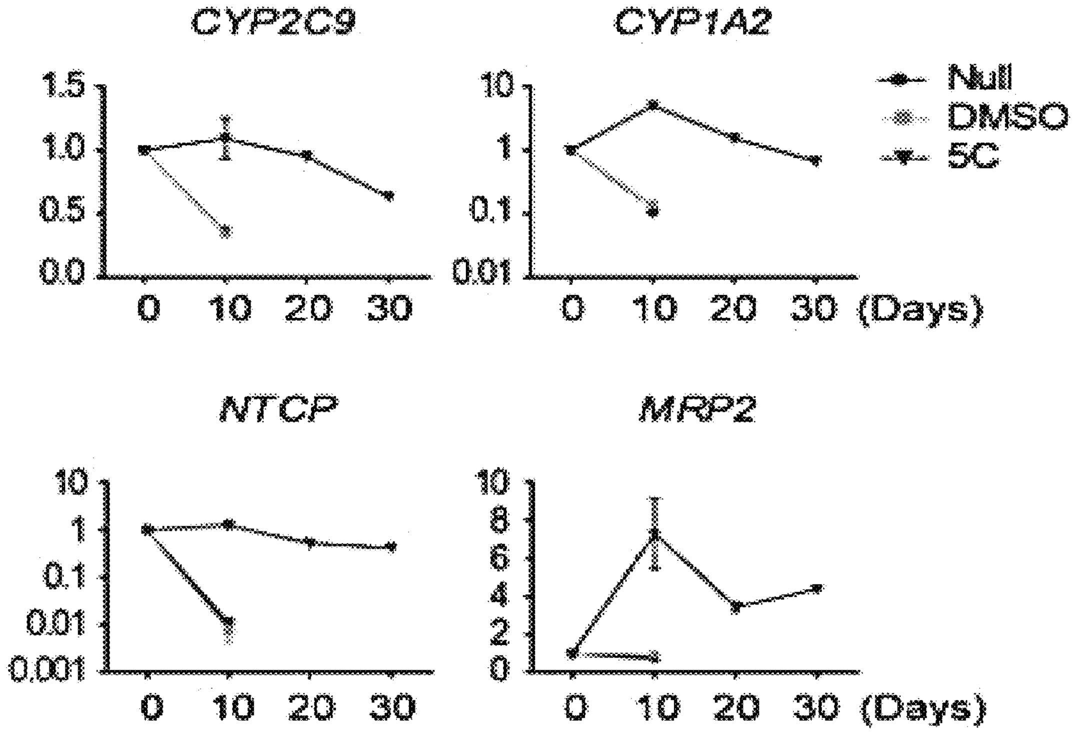

Hepatocytes are known to be important for the metabolism and detoxifying of exogenous drugs; however, the metabolizing activities of CYPs of hepatocytes are rapidly lost during culture (FIG. 1). In the disclosed 5C system, PHHs that had been cultured for 4 weeks were found to express the core CYP enzymes at a comparable level with F-PHHs. Additionally, the major phase II drug-metabolizing enzymes and phase III drug-metabolizing-associated transporters in 5C-PHHs were expressed at similar levels to F-PHHs (FIGS. 8D and 8E). These data suggested that 5C effectively preserved the expression of drug-metabolizing genes.

Figure 8F:
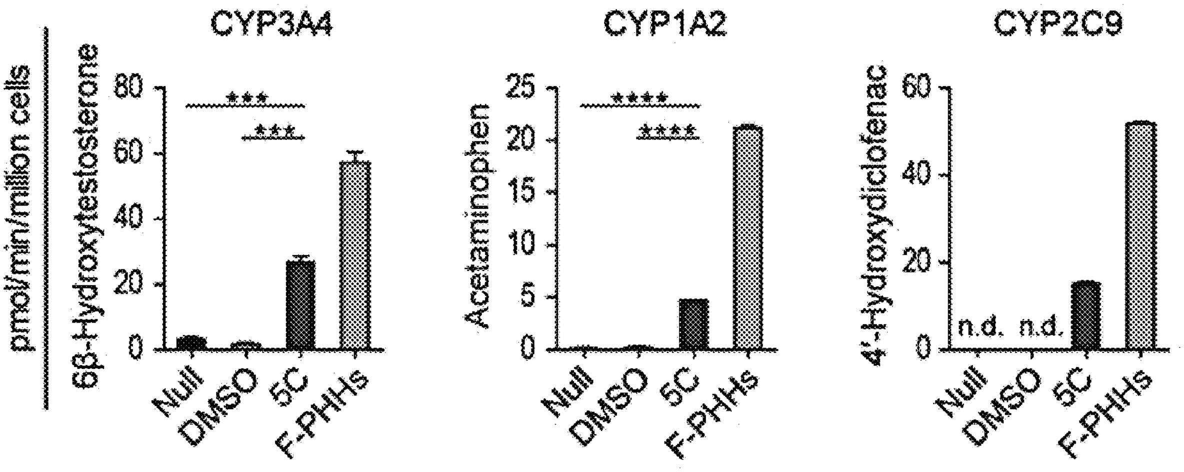
FIG. 8F shows the effect of 5C on the drug-metabolizing activities of cultured human hepatocytes in vitro measured as drug-metabolizing activities of five core CYP450 enzymes as measured by LC-MS after 2 weeks culture. n=3. Data not detected were labeled "n.d."
Figure 8F:
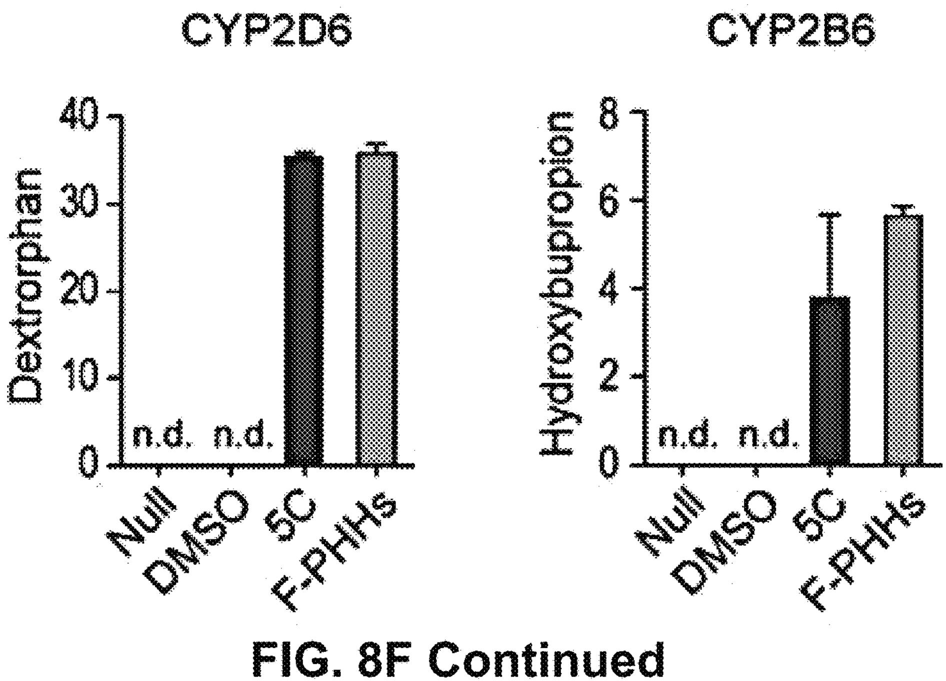

Key CYP enzymes, including CYP3A4, CYP1A2, CYP2C9, CYP2D6 and CYP2B6, responsible for the metabolism of approximately 80-90% of clinical drugs in humans were then characterized. Liquid chromatography-mass spectrometry analysis showed that, after 2 weeks in culture, the metabolizing activities of these major enzymes in 5C-PHHs were comparable to those of F-PHHs (FIG. 8F). In contrast, the metabolizing activities of PHHs cultured in control groups were almost undetectable (FIG. 8F). These results were reproducible on three different batches of PHHs. Collectively, these results indicated that 5C maintained the drug-metabolizing activities of cultured human hepatocytes in vitro.

Figure 9A:
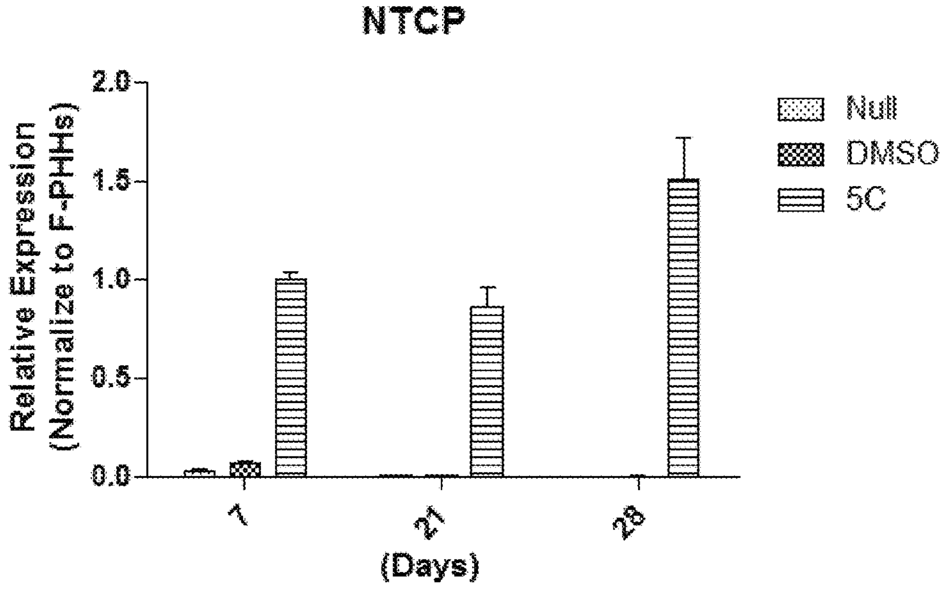
FIGS. 9A-F show that 5C supported of an entire life cycle of HBV infection in PHHs.
Figure 9B:
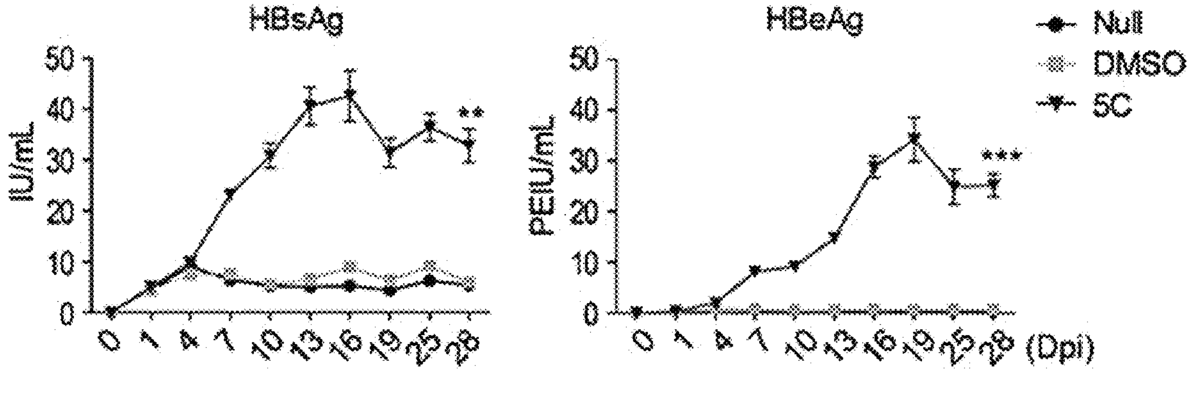
Figure 9C:
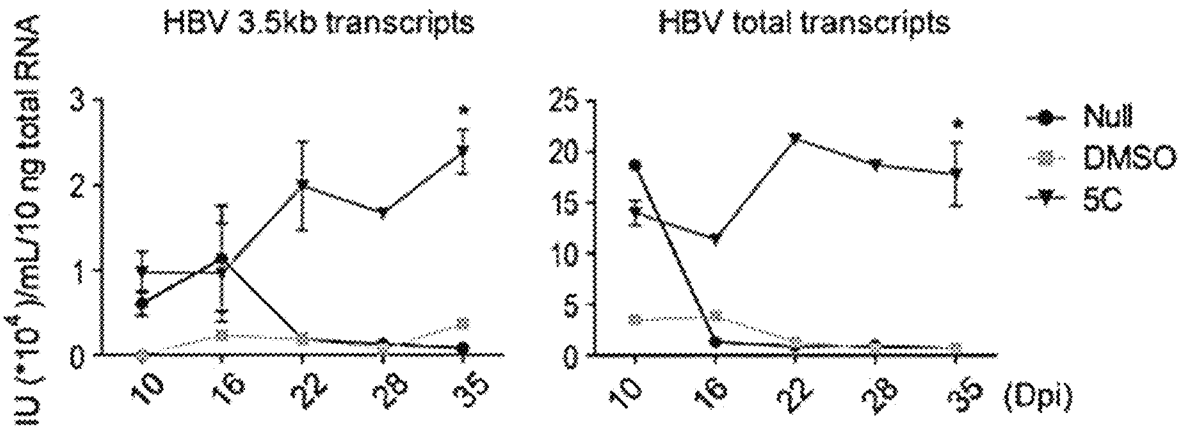
Figure 9D:
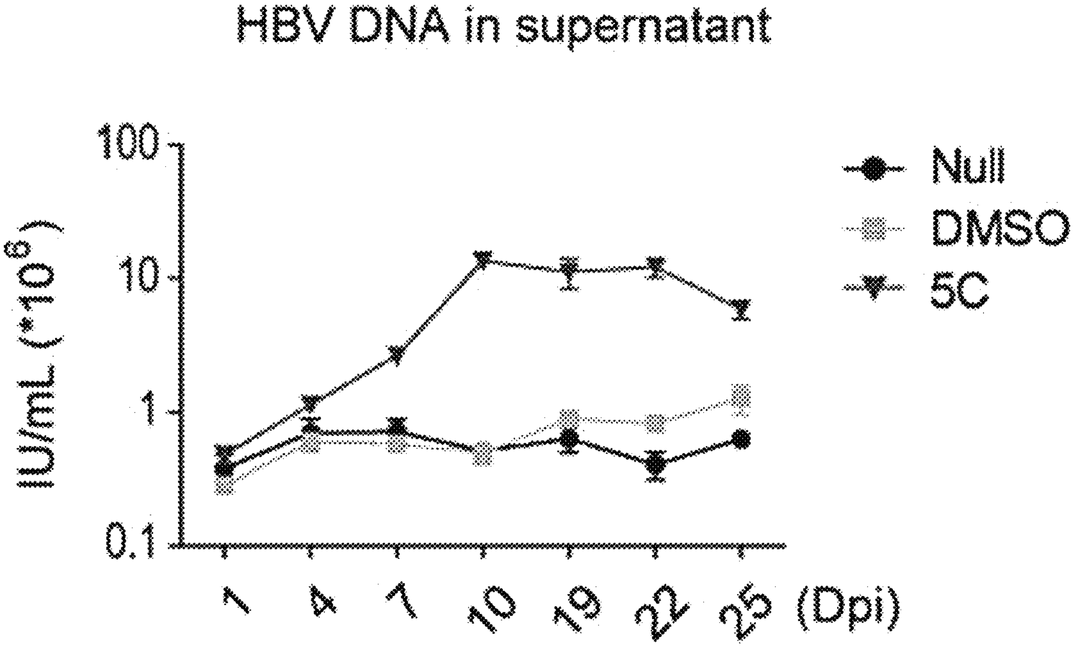
Figure 9E:
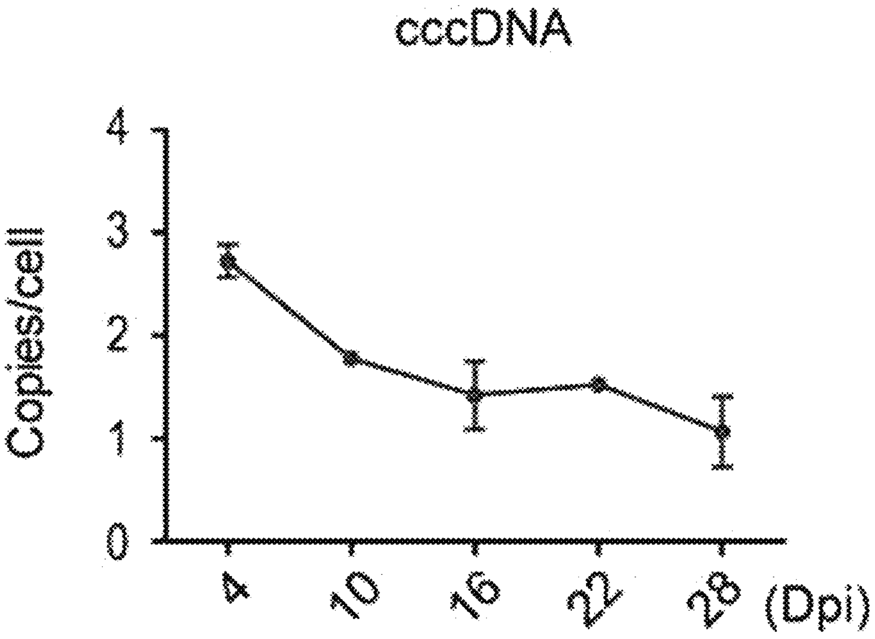
Figure 9F:
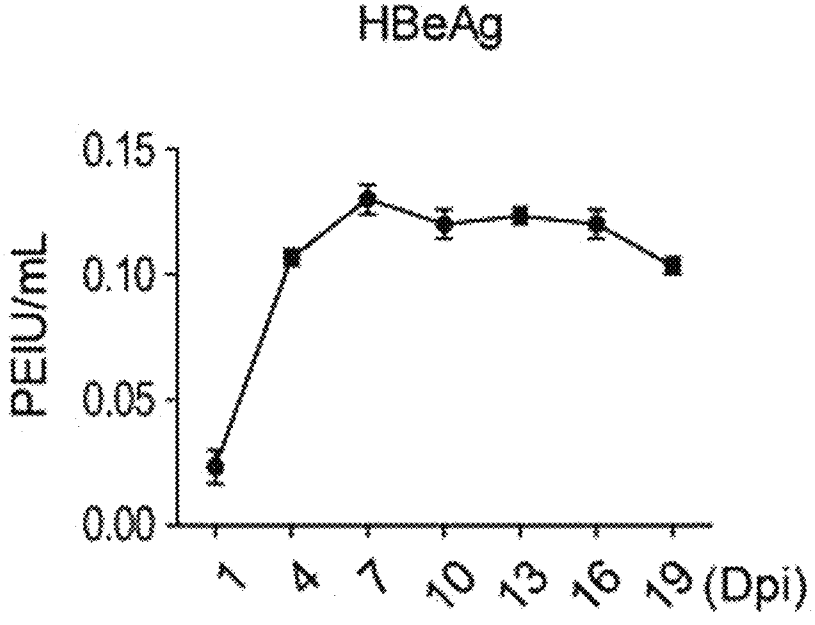
Figure 9G:
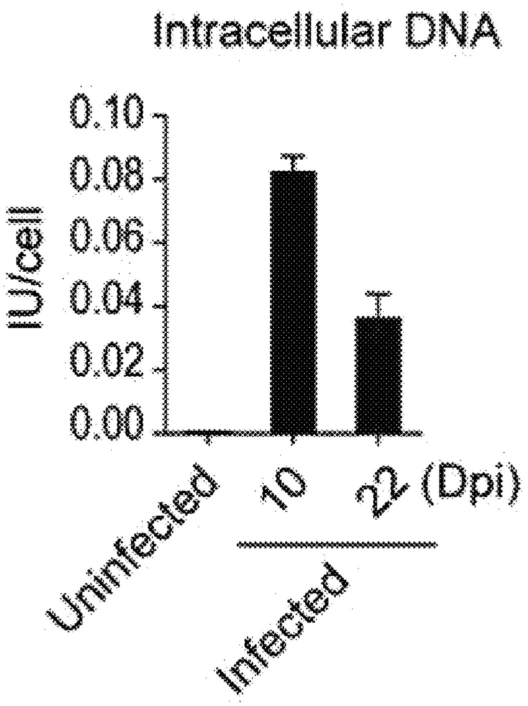
Figure 9H:
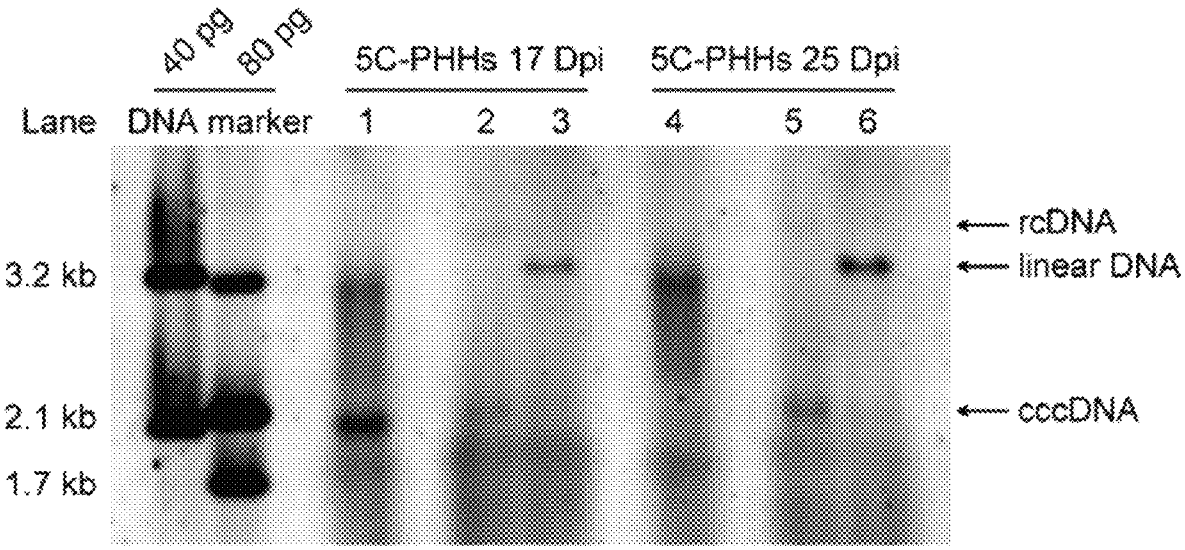
FIG. 9H is a Southern Blot analysis for HBV cccDNA in infected 5C-PHHs. HBV DNA was extracted by the core DNA extraction method (Lane 1 and 4) and an improved Hirt DNA extraction method (Lane 2, 3, 5 and 6). To confirm the identity of cccDNA, Hirt DNA preparations extracted from 5C-PHHs without treatment (Lanes 2 and 5) and with SpeI digestion (Lanes 3 and 6) were separated on an agarose gel. Dpi, days post infection.
Figure 10A:
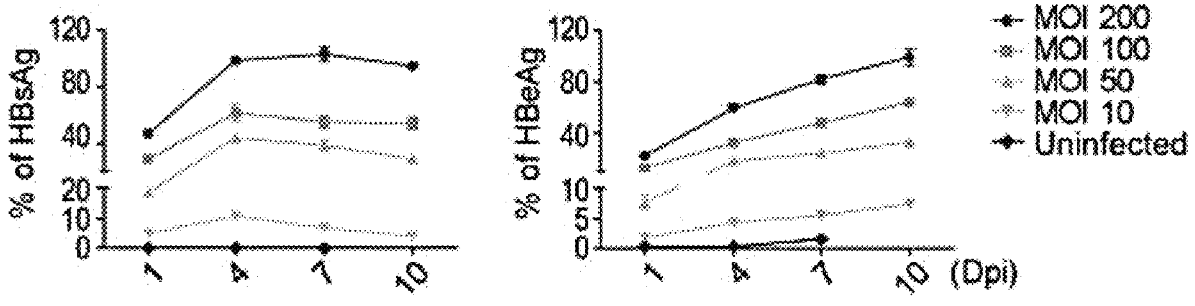
FIGS. 10A-B show HBV infection of 5C-PHHs with reduced multiplicity of infection (MOI).HBV infection was detected by secreted HBV antigens (HBsAg and HBeAg) (FIG. 10A) and intracellular HBV transcripts (FIG. 10B). n=3.
Figure 10B:
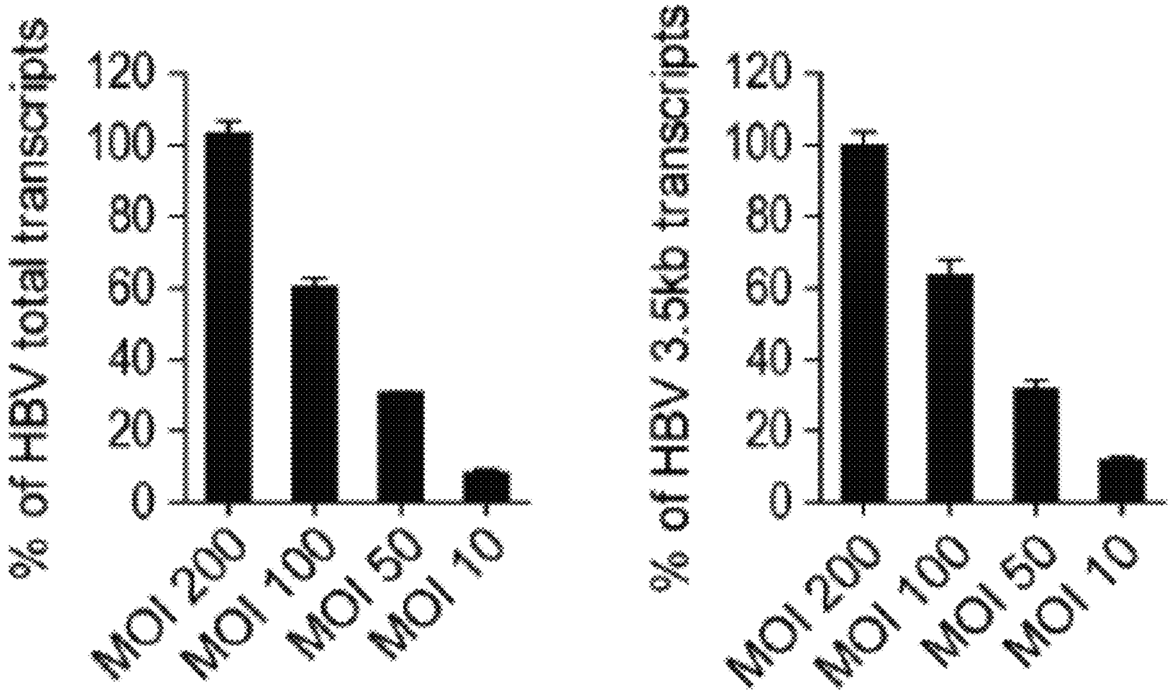

The robust functional maintenance of human hepatocytes by the 5C culture condition provides a platform for modelling HBV infection in vitro. qRT-PCR analysis confirmed the comparable expression level of NTCP between F-PHHs and PHHs cultured under 5C condition for 4 weeks (FIG. 9A). Next, by inoculation of PHHs with plasma from HBV-infected patients, successful HBV infection was achieved with HBV products (secreted HBsAg, HBeAg and DNA particles) detected in the supernatant of 5C-PHH culture (FIGS. 9B and 9D). Intracellular HBV-3.5 kb and HBVtotal RNA transcript levels also increased over time (FIG. 9C). The high-level generation of HBV products persisted for at least one month in 5C-PHHs. Importantly, the formation of HBV cccDNA was detectable by Southern Blot in 5C-PHHs (FIG. 9H) and qPCR analysis showed that cccDNA was persistently detectable at 4 weeks culture under 5C condition (FIG. 9E). Efficient HBV infection of 5C-PHHs was demonstrated by immunostaining for HBV core antigen (HBcAg) (data not shown). Furthermore, 5C-PHHs were still sensitive to HBV infection when MOI was reduced to 10 (FIGS. 10A and 10B). 5C-supported HBV infection was well reproduced in additional batches (>5 batches) of PHHs, including Cryo-PHHs (FIG. 11A-E). Importantly, 5C was able to stably support HBV infection from various sources, including HBV of various genotypes and from in vitro producer cell line HepAD38 (FIG. 11A-D).

Figure 11A:
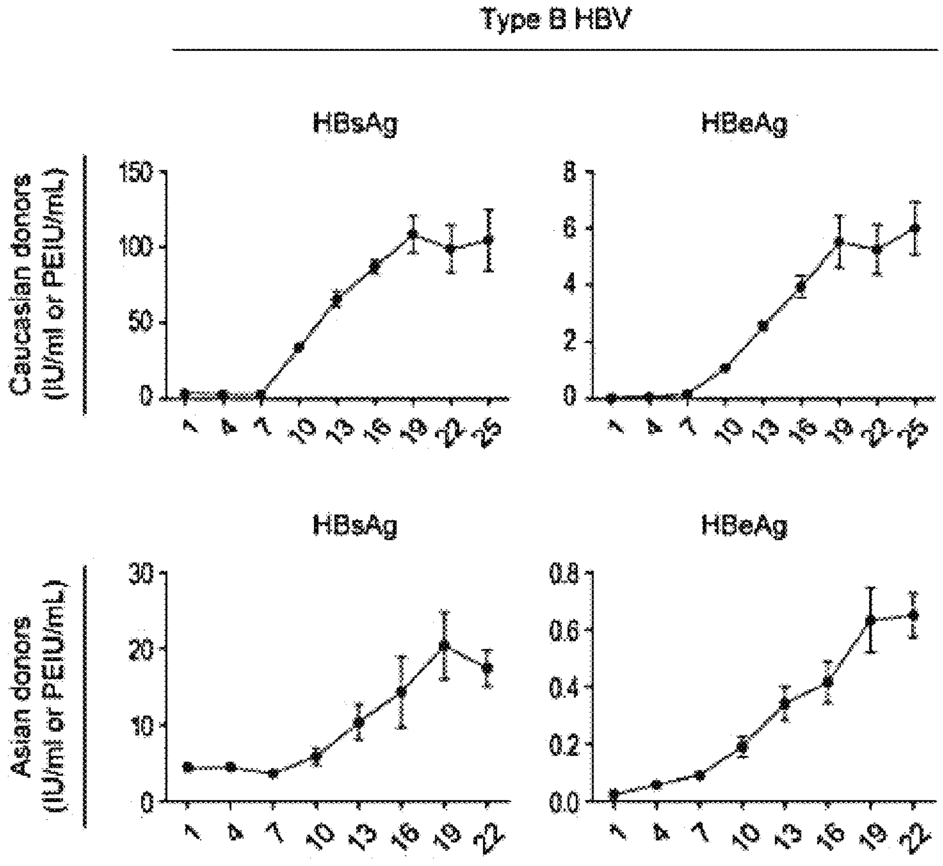
FIG. 11A shows HBsAg and HBeA in PHHs isolated from Caucasian donors and Asian donors were infected with type B or C HBV and further cultured in 5C. n=3.
Figure 11A:
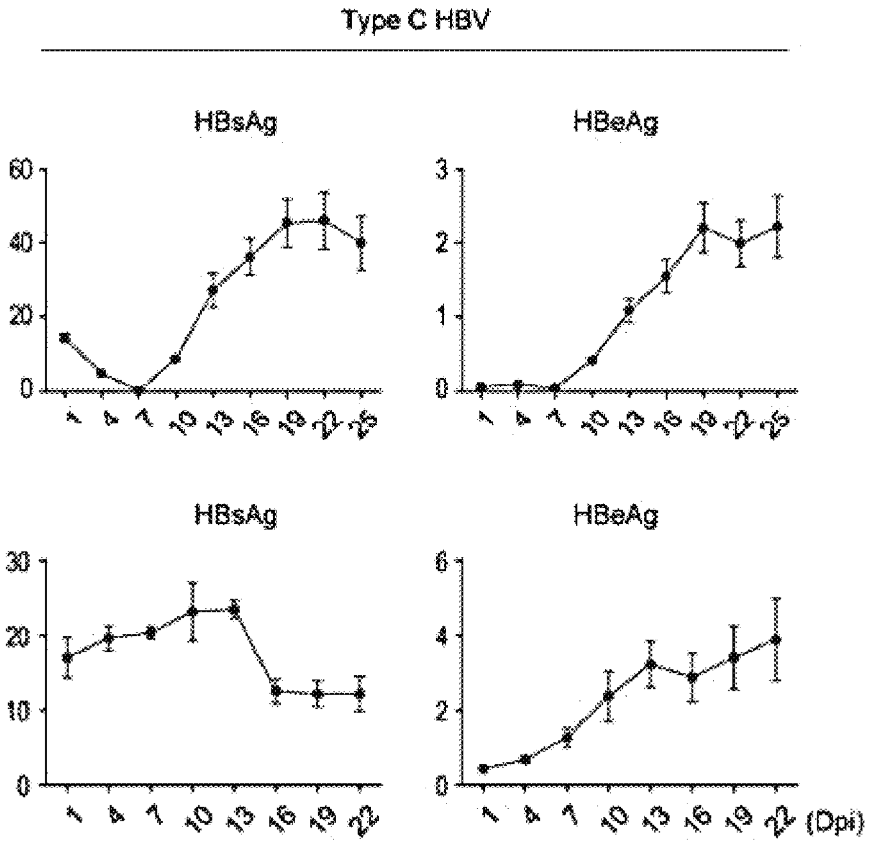
Figure 11B:
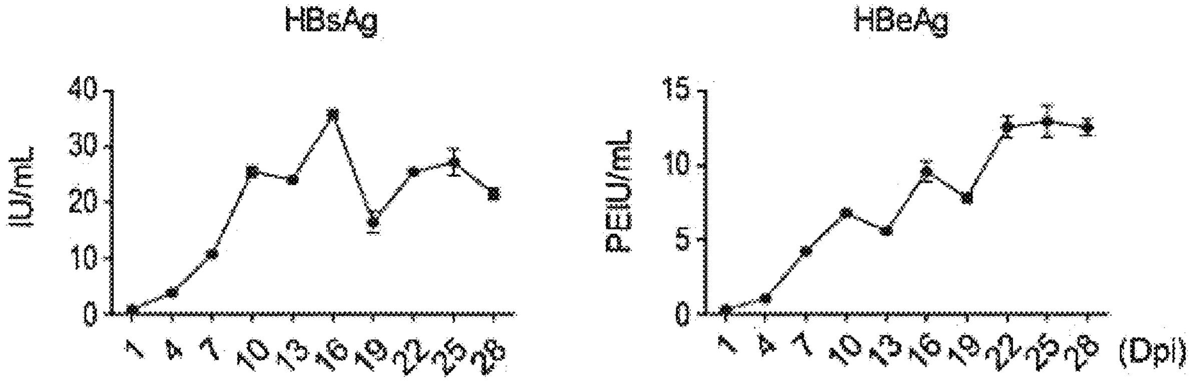
(FIG. 11B) Time course analysis of HBsAg and HBeAg levels in the supernatant of 5C-PHHs. n=3.
Figure 11C:
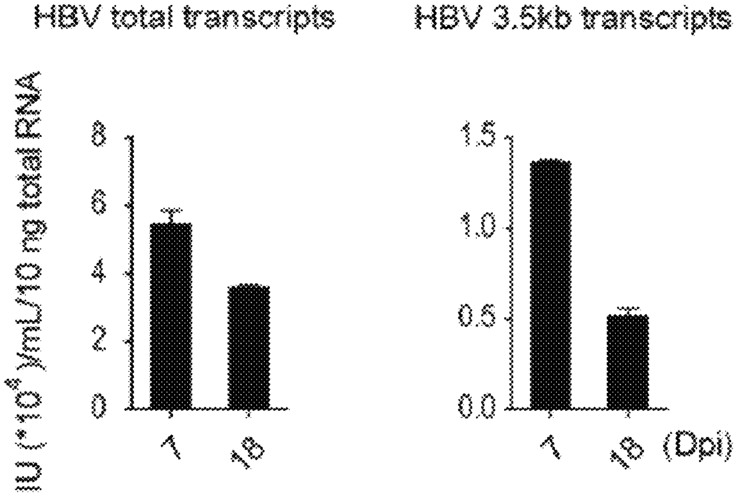
(FIG. 11C) HBV RNA, (FIG. 11D) HBV intracellular DNA and cccDNA were detected at 7 dpi and 18 dpi. n=3. Similar results were obtained in at least 3 independent batches.
Figure 11D:
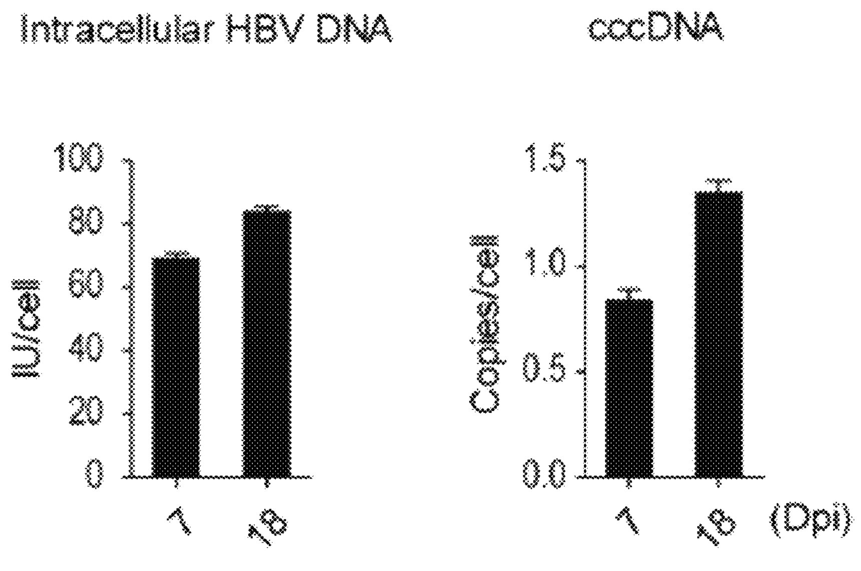
FIG. 11 B-D show the effect of 5C-PHHs infected with HBV particles generated from HepAD38.
(FIG. 11E) Time-course analysis of HBeAg of 5C-PHHs infected at various MOI. Neutralizing antibody (anti-S antibody) was added from 1 Dpi. n=3.
(FIG. 11F) Quantification of HBcAg positive cells at Dpi 28. n=3.
Figure 11E:
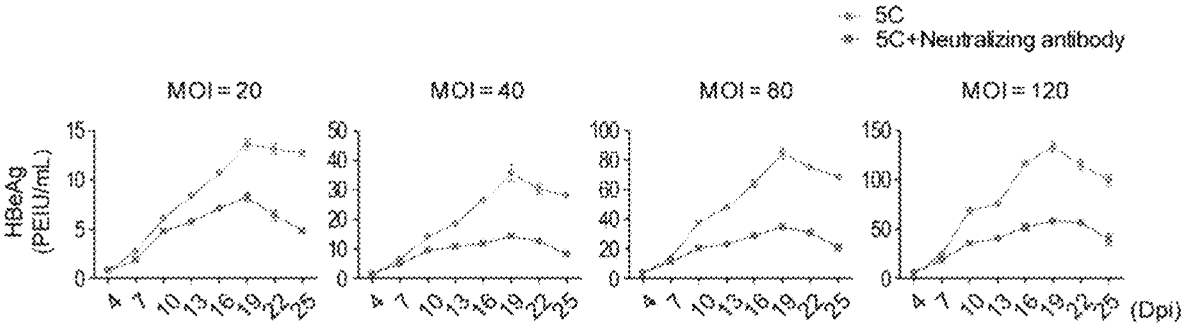
Figure 11F:
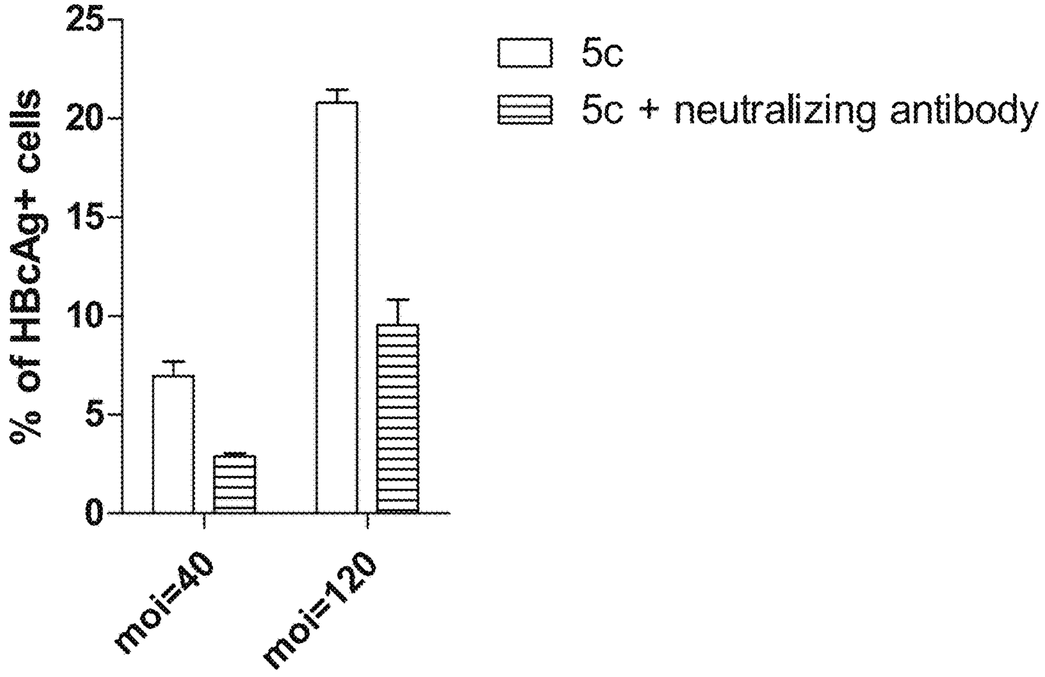
Figure 12A:
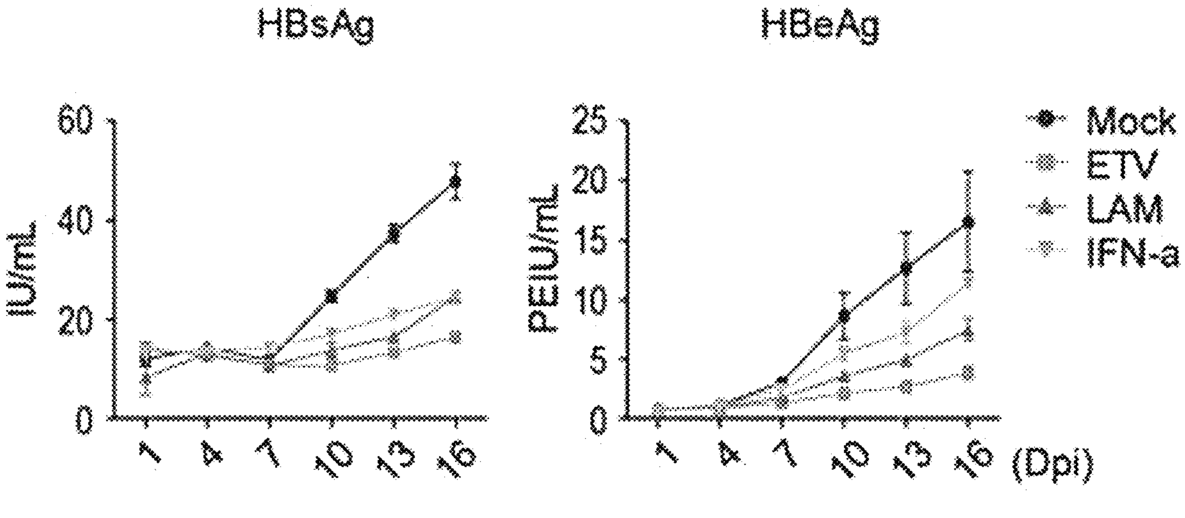
FIGS. 12A-D show HBV-infected 5C-PHHs response to anti-HBV drugs.
Figure 12B:
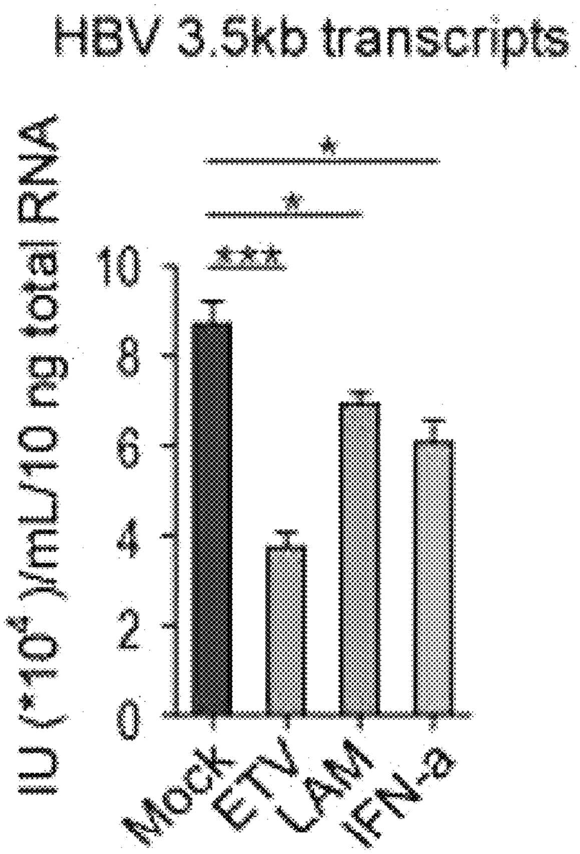
Figure 12C:
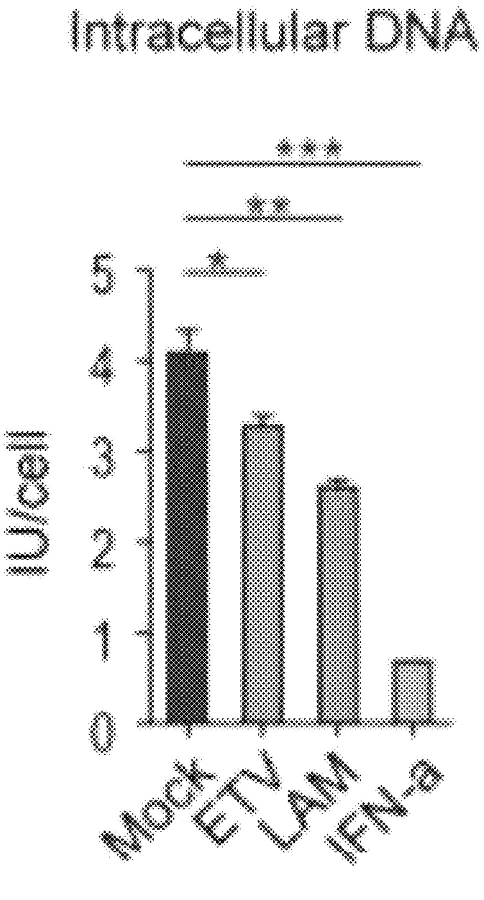
Figure 12D:
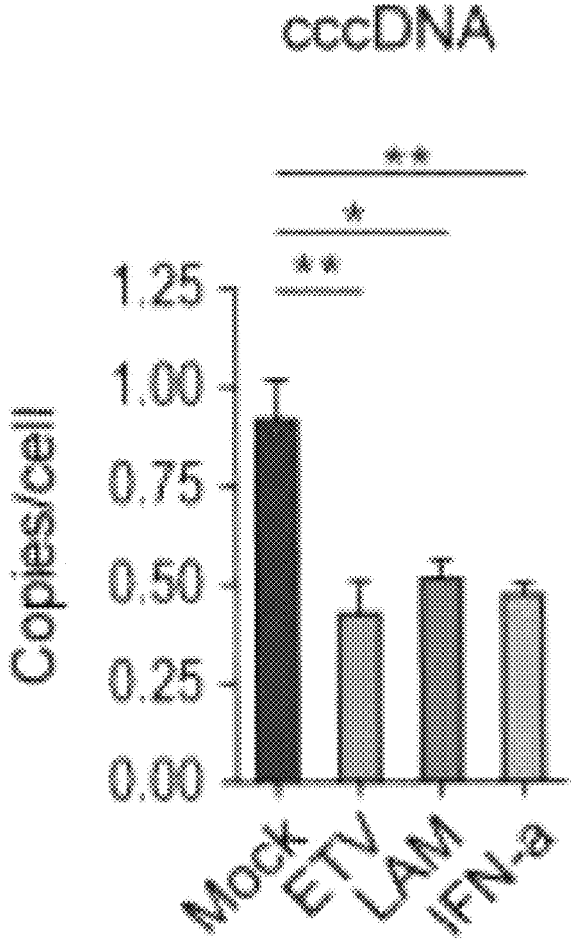

Viral particles were harvested from the supernatants of the HBV-infected 5C-PHHs and used them to inoculate naïve PHHs. HBeAg and HBV DNA were detected in PHHs inoculated with the supernatant of HBV-infected 5C-PHHs (FIG. 9F-G), indicating that 5C-PHHs could support the entire HBV life cycle and generate infectious particles of HBV. Additionally, the proportion of HBV infected 5C-PHHs increased with prolonged culture time (data not shown; FIG. 11E), suggesting HBV spread possibly via cell-to-cell transmission and/or by de novo infection of HBV particles.

Figure 13A:
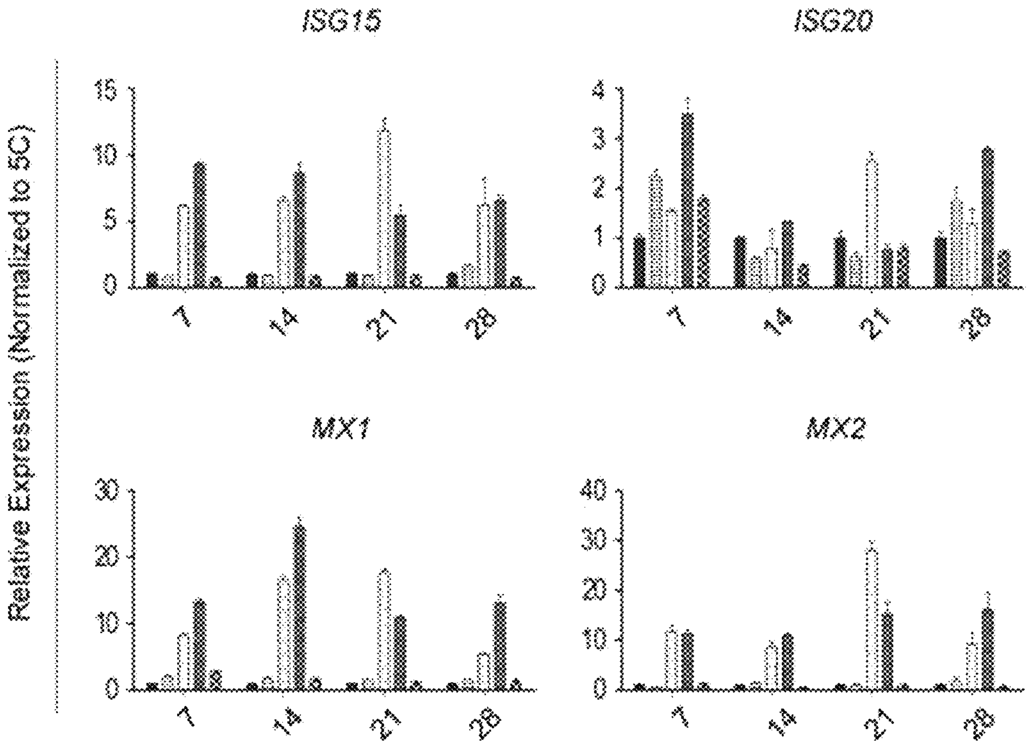
FIG. 13A is a time course analysis of inflammatory response in cultured 5C-PHHs. Relative gene expression was normalized to 5C. n=3. Similar results were obtained in 3 independent batches.
Figure 13A:
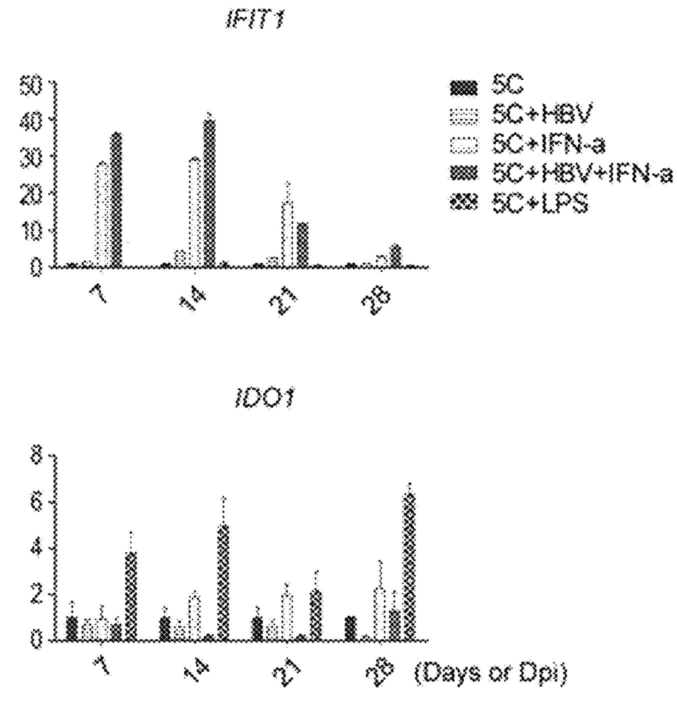

The 5C-PHH infection model was found to sensitively respond to two classes of clinical anti-HBV drugs: interferon-α (IFN-α) and nucleos(t)ide reverse transcriptase inhibitors, such as entecavir (ETV) and lamivudine (LAM). Treatment of HBV infected 5C-PHHs with all three drugs (ETV, LAM and IFN-α) led to the reduction of HBV products (FIG. 12A-D). Similar results were obtained with cryopreserved PHHs cultured in 5C, whereby IFN-α led to the significant reduction of cccDNA. Additionally, while interferon-stimulated genes (ISGs) significantly upregulated in long-term cultured 5C-PHHs when treated with IFN-α, they responded weakly to HBV infection, in line with previous reports of HBV evasion from innate immunity of hepatocytes (FIG. 13A) (Cheng, et al., *Hepatol.,* 66:1779-1793 (2017)).

Figure 13B:
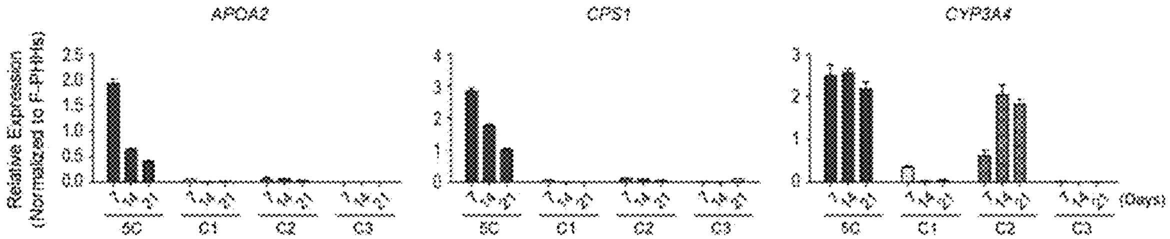
FIGS. 13B-D is a comparison of 5C with three other reported PHH culture conditions on long-term hepatocyte maintenance and HBV permissiveness. Condition 1, C1 (Winer et al., *Nat Comm.* 8:125 (2017)); Condition 2, C2 (Lucifora, et al., *Science,* 343:1221-28 (2014)) and Condition 3, C3 (Xia, et al., *J. Hepatol.,* 66:494-503 (2017)).
Figure 13C:
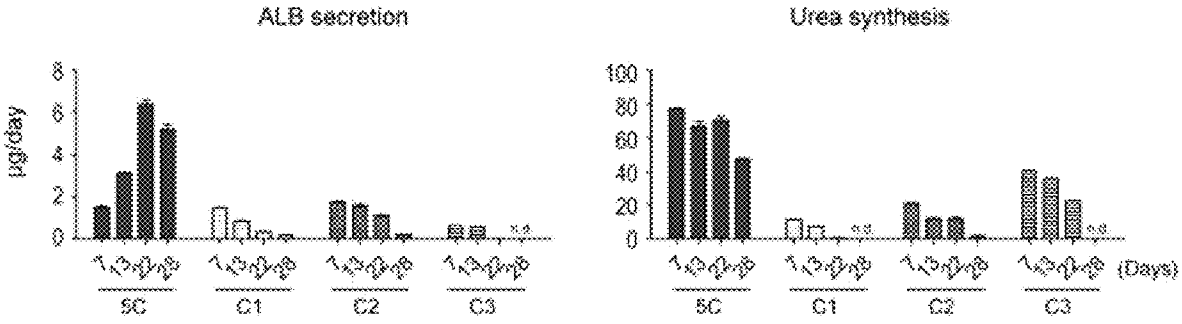
Figure 13D:
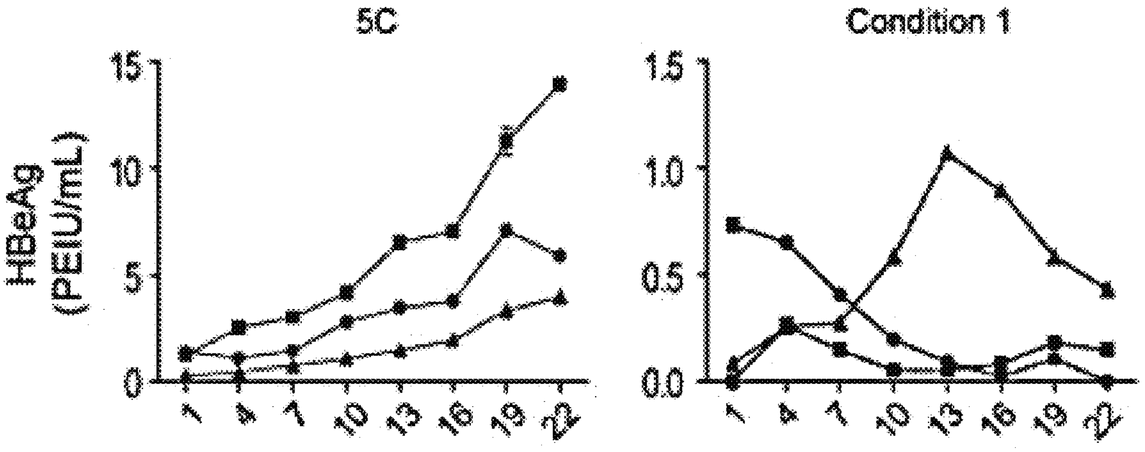
Figure 13D:
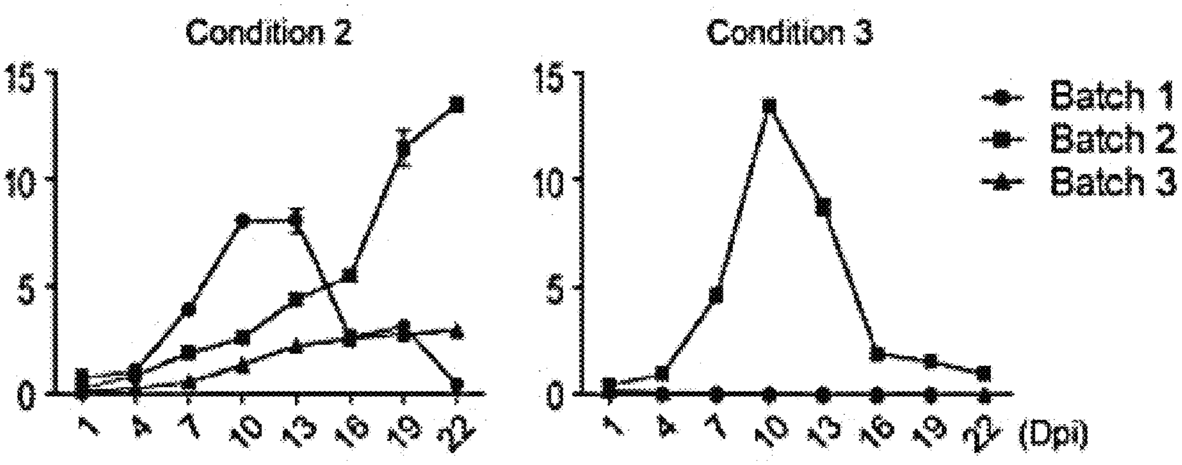
Figure 14A:
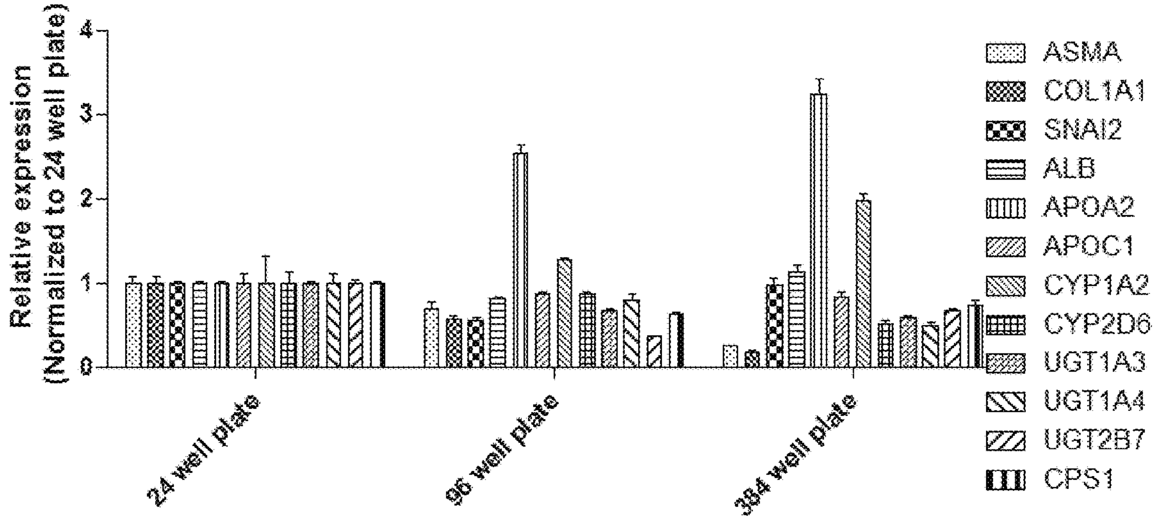
FIGS. 14A-C show application of the 5C culture condition to various plating formats. PHHs were plated in microwell plates (96-well plate and 384-well plate) and further cultured in 5C.
Figure 14B:
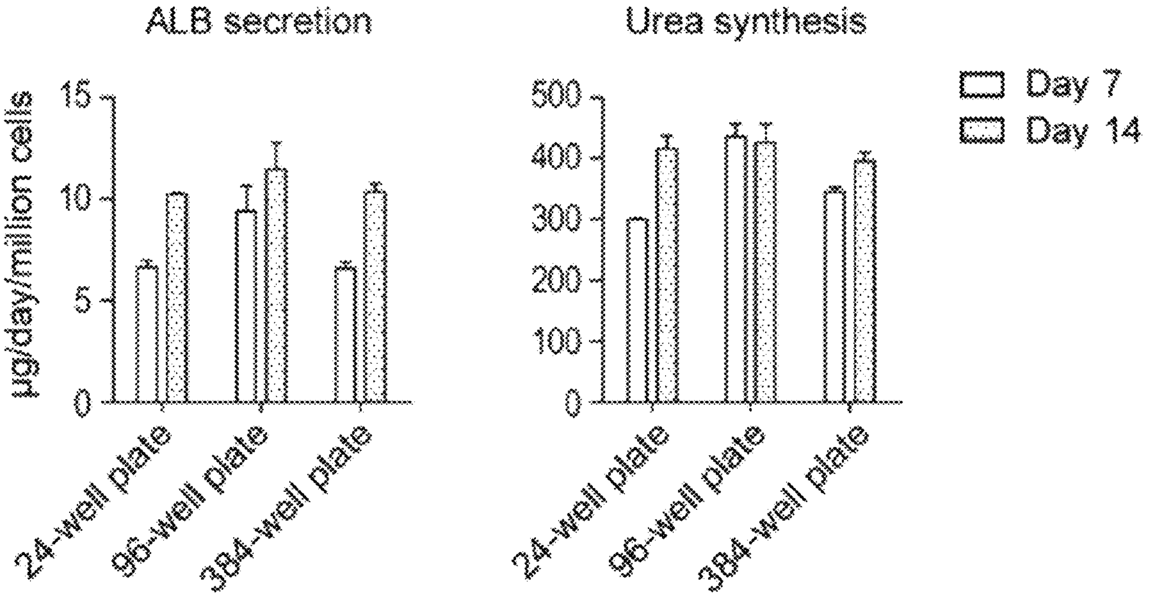
Figure 14C:
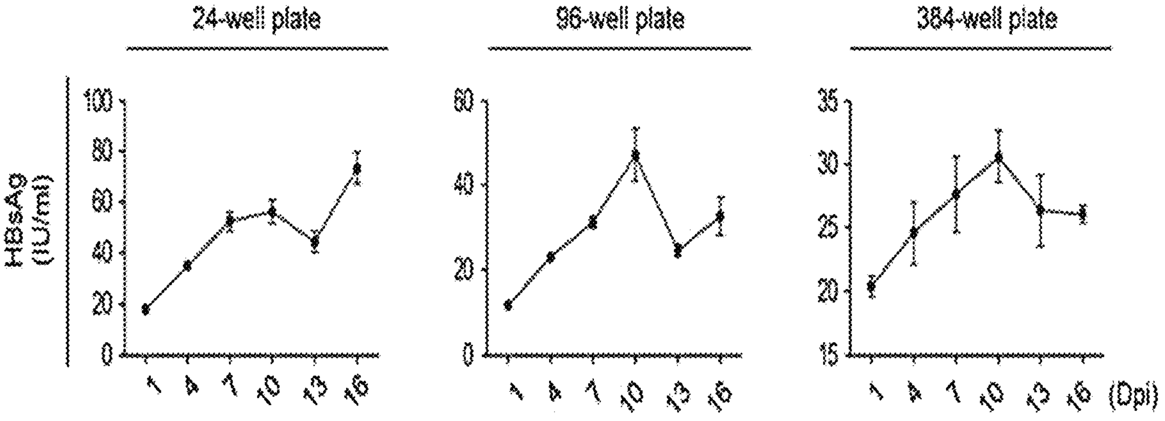
Figure 14C:
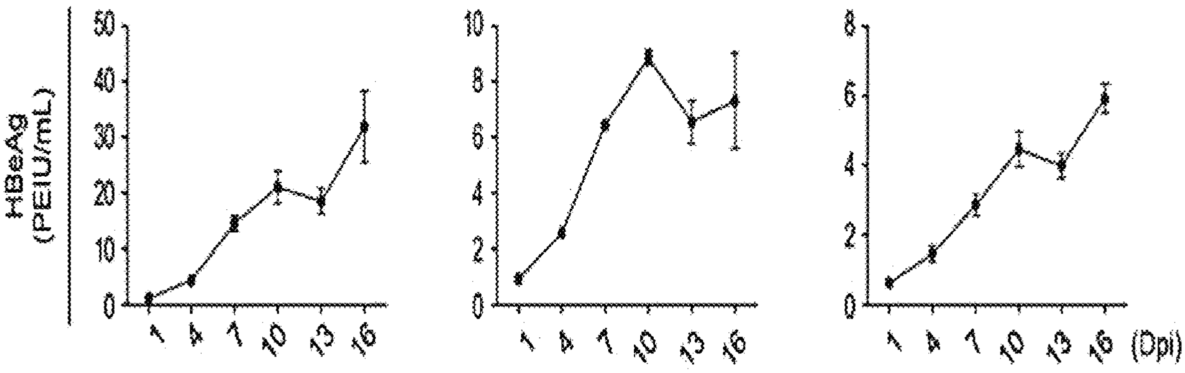

The culture condition was further compared with other reported culture conditions for long-term HBV infection in PHHs (Lucifira, et al., *Science,* 343:1221-1228 (2014), Winner, et al., *Nat. Comm.,* 8:1256 (2017), Xia, et al., *J. Hepatol.,* 656:494-5603 (2017)) and found that 5C showed clear advantages, particularly in the long-term maintenance of hepatic function and the stable support of HBV infection (data not shown; FIGS. 13B, 13C and 13D). Importantly, the 5C condition could be downscaled to the microwell format, amenable to high throughput applications (FIG. 14A-C). These results further establish 5C as a simple yet highly effective and stable culture condition for the long-term maintenance of PHHs in vitro, and of great value to the study of HBV infection.

Figure 15A:
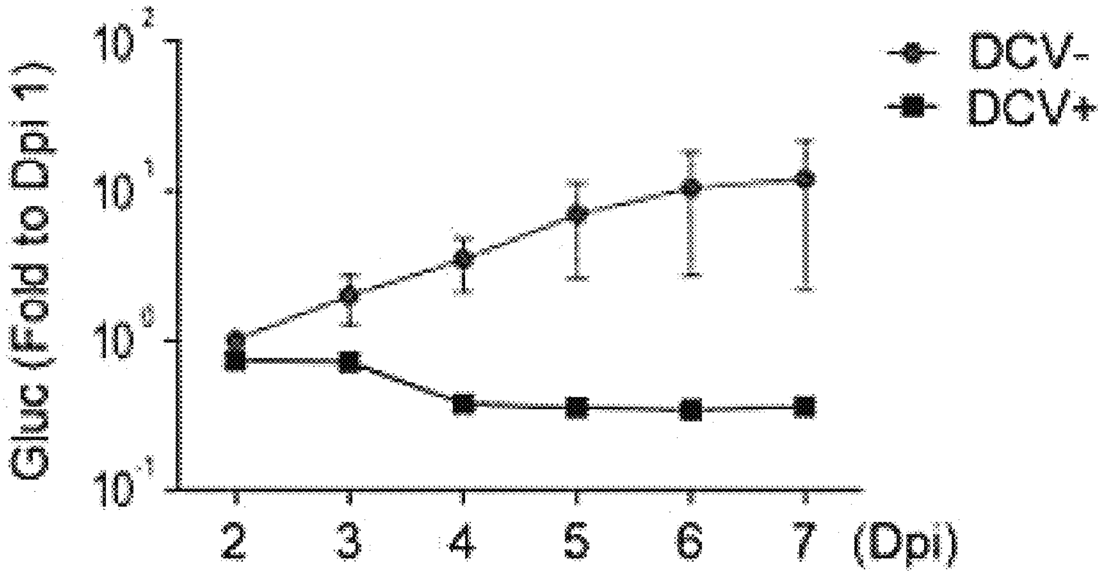
FIGS. 15A-C show the effect of 5C on infection of HCV in Cryo-PHHs. Cryo-PHHs were infected with HCVcc (MOI=2) and further cultured in 5C with or without DCV treatment.
Figure 15B:
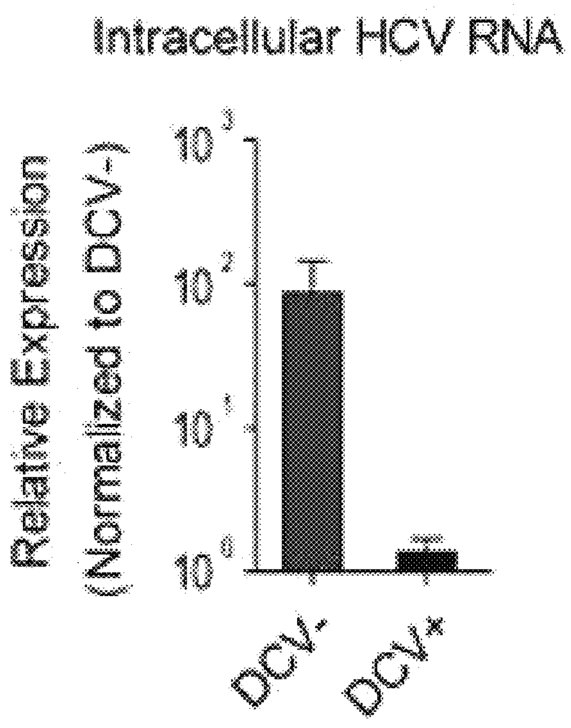
Figure 15C:
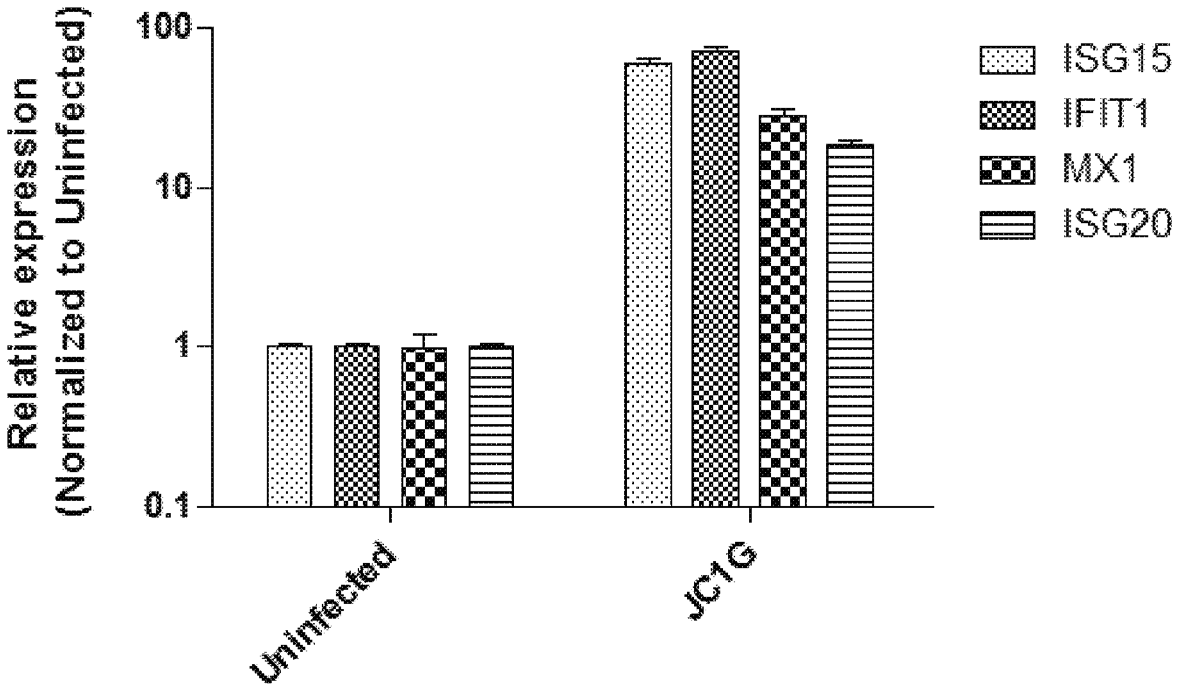

In addition to HBV, 5C-PHHs could also be infected with other hepatitis viruses, such as the hepatitis C virus (HCV). 5C-PHHs were exposed to infectious viral particles of the HCV Jc1G expressing a secreted Gaussia luciferase (Gluc) reporter. Viral replication was detected in 5C-PHHs, and was effectively blocked by DCV, a direct acting antiviral for hepatitis C treatment (FIGS. 15A and B). Unlike HBV, HCV induced robust ISG expression in 5C-PHHs (FIG. 15C). Collectively, these results show that 5C-PHHs could serve as an effective model for modeling hepatotropic infection and investigating antiviral strategies.

In summary, a chemical approach to maintain long-term the functionality of primary human hepatocytes long term has been developed. Using this platform, a persistent HBV infection that extends over the entire viral life cycle in PHHs and releases viral progeny in vitro was demonstrated. Notably, the formation of HBV cccDNA was captured in PHHs, which is key for HBV to re-enter the viral lifecycle and induce a relapse of HBV in the human liver. This platform is simple and easily applied to high throughput screening for devising new antiviral strategies, particularly for cccDNA targeting compounds, which may likely prove essential for finding a cure to chronic hepatitis. Methodologically, small molecules have highly tunable functionalities that precisely balance cell signals and modulate molecular networking to stabilize cell identity and functionality of mature cells, a strategy that could be extended to the maintenance of other functional cell types.

Global Gene Expression of Hepatocytes Cultured in 2C and 5C Conditions

To monitor the dynamic gene expression changes of PHHs during the whole culture process, hepatocytes of two different batches (B1 and B2) that were cultured with or without 2C and 5C, respectively, were harvested at days 1.5, 3, 5, 8, 15 and 27 for gene expression profiling by RNA-Seq. Both F-PHHs and Cryo-PHHs were used as positive controls. Hierarchical clustering illustrated that 2C-PHHs and 5C-PHHs had similar global gene expression profiles to their freshly isolated counterparts (data not shown). Consistent with the functional maintenance, the results showed that 2C and 5C condition maintained the expression of key transcription factors (TFs) of hepatocytes, the expression level of which were comparable to those of F-PHHs (data not shown). These data show that 2C/5C support the long-term maintenance of the global gene expression profile of cultured PHHs similar to that of F-PHHs.

Both CAMP-PKA and cAMP-EPAC are Indispensable for Maintenance of PHHs

To investigate the potential mechanism underlying our chemical conditions; the core small molecule combination maintaining human hepatocytes, FSK and SB43 were substituted with their analogues either blocking or stimulating the same signaling pathways. Meanwhile, the gene expression repertoire of cultured hepatocytes was profiled by RNA-Seq. Hierarchical clustering analysis showed that FSK played a pivot role in maintenance of PHHs (data not shown). NKH477 (cAMP agonist) and db-CAMP (cAMP analogue) replaced FSK to maintain the global gene expression of PHHs. By contrast, hepatocytes treated with 1,9-Dideoxyforskolin (1,9-dFSK), the inactive analogue of FSK, induced expression profiles similar to control groups without FSK. The effect of db-CAMP on hepatic marker genes expression, ALB secretion and urea synthesis was investigated (data not shown). The data indicated that FSK was an essential small molecule in PHHs maintenance and that it functioned through activation of AC (data not shown).

Down-stream targets of cAMP were further investigated. The results showed that inhibition of either PKA or EPAC individually boosted the expression of mesenchymal markers, indicating occurrence of EMT during hepatocyte culture (data not shown). Additionally, activation of either PKA or EPAC individually could not fully compensate for the withdrawal of FSK from 2C (data not shown). These data suggest that cAMP could be the central signaling hub of PKA, EPAC, and cAMP downstream pathways, which are synergistic but non-redundant in PHHs maintenance.

Chemical Cocktail Promoted Functional Maturation of hESC Derived Hepatocytes

Considering 2C could maintain the mature function of human hepatocytes, studies were conducted to test whether the disclosed chemical culture condition could promote the maturation of human embryonic stem cell-derived hepatocytes (hESC-Heps). hESC-Heps were generated using a modification of established protocols (Zhao et al., Cell Res., 23:157-161 (2013)). Immunofluorescence analyses showed that hESC-Heps expressed the hepatocyte-specific TFs FOXA2, HNFA4, HNF6, PROX1 and CEBPA (data now shown). Albumin was detected in hESC-Heps. hESC-Heps were immunopositive for AFP and ALB (data not shown) and CYP3A4, but not for CYP1A2, CYP2C9, CYP2A6 or CYP2E1 (data not shown). These data indicated hallmarks of fetal-like function of hESC-Heps.

Figure 16:
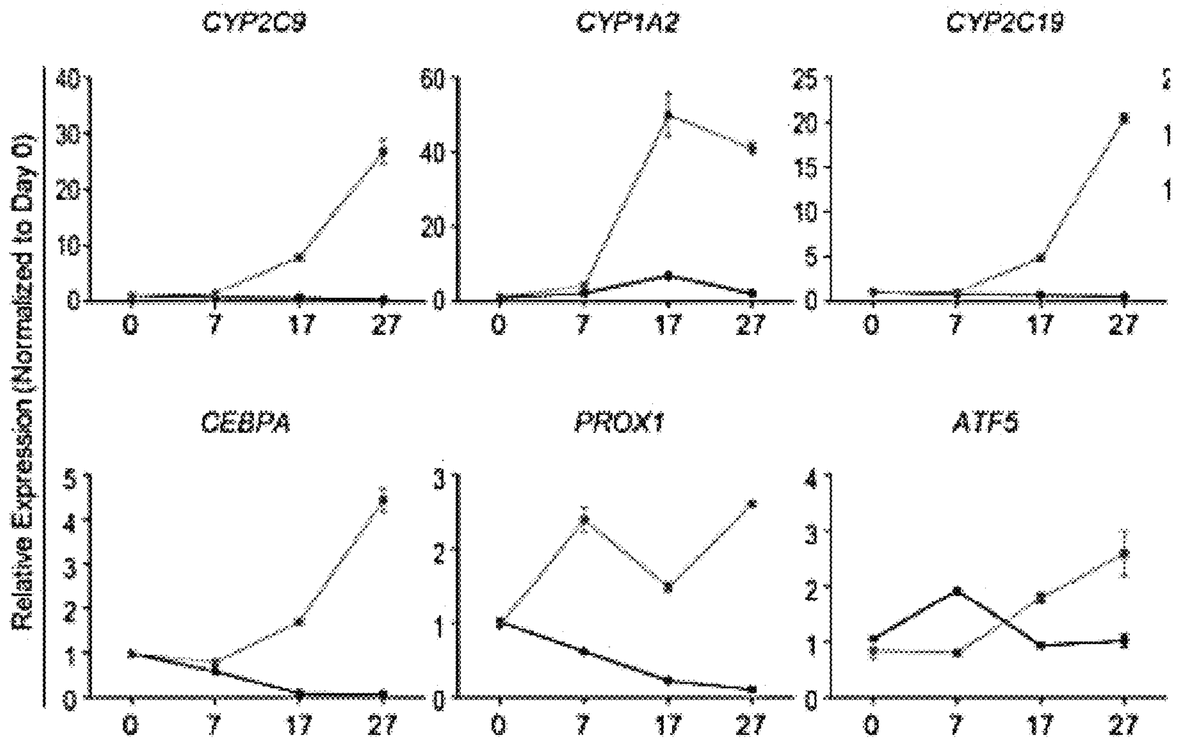
FIG. 16 shows the kinetics of the expression of a panel of CYP enzymes, drug metabolizing nuclear receptors, and key transcription factors in human embryonic stem cell-derived hepatocytes (hESC-Heps) cultured in 2C condition. Relative gene expression was detected by qRT-PCR and was normalized to Day 0. n=2.
Figure 16:
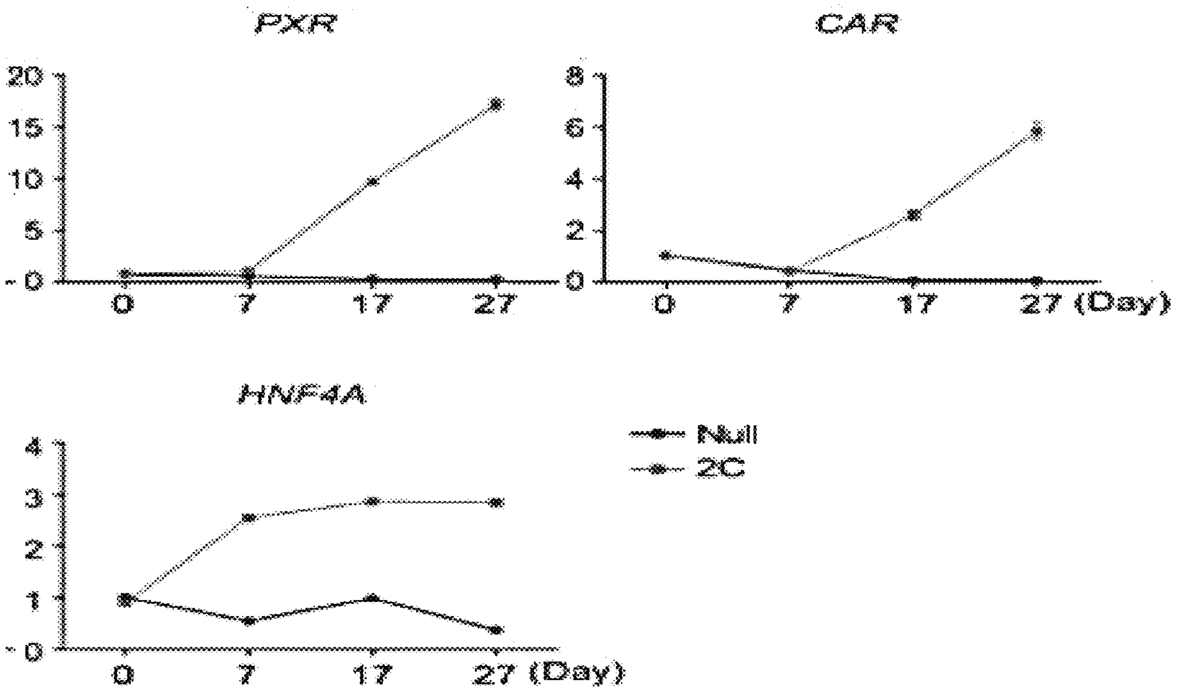

By contrast, after transferring hESC-Heps to the 2C condition, hESC-Heps acquired a polygonal-like morphology with a small nucleus-cytoplasm ratio (data now shown). Additionally, hepatic functional marker genes (HNFA4, HNF6, PROX1, CEBPA, CYP2C9, CYP2A6, CYP1A2, etc.) were gradually up-regulated from day 7 in culture with 2C (data not shown and FIG. 16). Notably, intercellular bile canaliculi were constituted after 2 weeks in culture (data not shown) and had a declined AFP expression (data not shown). Importantly, 2C-cultured hESC-Heps expressed a spectrum of CYP enzymes, including CYP3A4, CYP1A2, CYP2C9, CYP2C19, CYP2A6 and CYP2E1 (data not shown). PXR and CAR, two pivotal nuclear receptors associated with drug metabolism, were markedly up-regulated under the 2C condition (FIG. 16). Under the 2C condition, the expression of HNF4A, a master regulator of adult hepatocyte-specific genes, was observed, and the expression of maturation factors, including CEBPA, PROX1 and ATF5, was increased. Otherwise the hepatocyte-specific genes gradually decreased without 2C treatment (FIG. 16). Collectively, these data show that the disclosed chemical condition for adult hepatocytes promoted the functional maturation of hPSC-Heps closely to a stated to that of adult hepatocytes.

We claim:

1. A supplemented primary hepatocyte cell culture composition comprising primary hepatocyte cells, and a combination of an activator of adenylate cyclase and a TGFβ inhibitor, in an effective amount to maintain functional hepatocyte function in vitro, for a long term of at least two week, measured as an increase in expression of at least one hepatocyte marker following at least two weeks of in vitro hepatocyte culture in the supplemented cell culture composition, compared to hepatocytes cultured in an unsupplemented culture composition without an activator of adenylate cyclase and a TGFβ inhibitor, wherein the primary hepatocyte cells express the hepatocyte marker at a level that is comparable or more to a level expressed by freshly isolated hepatocytes from the same organism.

2. The composition of claim 1 comprising a combination of at least one activator of adenylate cyclase, one TGFβ inhibitor, one Notch inhibitor, one Wnt inhibitor, and one BMP inhibitor.

3. The composition of claim 2, wherein the adenylate cyclase activator is forskolin, TGFP inhibitor is SB431542 (SB43); the Notch inhibitor is DAPT, the Wnt inhibitor is IWP 2 or the BMP inhibitor is LDN193189.

4. The composition of claim 2, wherein the hepatocytes express at least six hepatocyte functional proteins following at least 90 days in culture, at the same levels as F-PHHs from the same organism.

5. The composition of claim 1, wherein the hepatocyte functional protein is selected from the group consisting of albumin (ALB), CPS1, ARG, NAGS, PXR, CAR, APOA2, APOB, F2, F10, Cytochrome P450 (CYP) 3A4, CYP1A2, CYP2C9, CYP2D6, NTCP, PXR, CAR and UGT2B7.

6. The composition of claim 2, wherein the hepatocytes express at least 6 hepatocyte functional proteins following at least 60 days in culture, at the same levels as freshly isolated primary hepatocytes (F-PHHs) from the same organism.

7. Hepatocytes cultured by using the composition of claim 1.

8. The hepatocytes of claim 7, wherein the hepatocytes possess at least one characteristic selected from the group consisting of hepatocyte morphology (polygonal shape), established hepatocyte functions such as albumin secretion and urea synthesis, and expression at least one known hepatocyte marker, following at least two weeks of in vitro culture.

9. The hepatocytes of claim 8, wherein the hepatocytes possess at least one characteristic after three- to eight weeks in culture.

10. The hepatocytes of claim 8, wherein the at least one hepatocyte marker is selected from the group consisting of cytochrome P450 (CYP) 3A4; CYP1A2; CYP2C9; CYP2D6; CYP2B6; CYP2C19; UDP-glucuronosyltransferase (UGT) 1A3; UGT1A4; UGT2B15; UGT2B7, NTCP ($Na^+$-taurocholate cotransporting polypeptide) ABCG2 (ATP-binding cassette super-family G member 2; MRP2 (Multidrug resistance-associated protein 2); and organic-anion-transporting polypeptide (OATP) 1B1.

11. The hepatocytes of claim 7, expressing at least one, at least two, at least 3, at least four, at least five or at least six of the following hepatocyte markers: APOA2, APOB, F2, F10, CYP3A4, CYP1A2, CYP2C9 and UTG2B7 at levels comparable to freshly isolated hepatocytes obtained from the same organism, at 90 days in culture.

12. The hepatocytes of claim 7, comprising metabolically active CYP3A4, CYP1A2, CYP2C9, CYP2D6 and CYP2B6, after 2 weeks in culture, at levels comparable to those of F-PHHs.

13. A cell culture, produced by a method comprising inoculating the hepatocytes of claim 7 with a hepatic parasite for a time effective for parasite infection and culturing the parasite-infected cells in vitro in hepatocyte culture (HC) supplemented hepatic basal medium.

14. The cell culture of claim 13, wherein the parasite is a hepatitis virus, the method comprising inoculating the hepatocytes of claim 7 with a hepatitis virus for a time effective for virus infection and culturing the virus-infected cells in vitro in HC supplemented hepatic basal medium.

15. The cell culture of claim 14, wherein the hepatitis virus is hepatitis B, hepatitis D or hepatitis C.

16. The cell culture of claim 15, comprising hepatitis B virus (HBV) covalently closed circular DNA (cccDNA) at 4 weeks in vitro culture.

17. The cell culture of claim 13, wherein the parasite is a malaria parasite selected from the group consisting of *P. falciparum, P. vivax, P. ovale*, and *P. malariae*.

* * * * *

SEQUENCE LISTING

```
<160> NUMBER OF SEQ ID NOS: 84

<210> SEQ ID NO 1
<211> LENGTH: 22
<212> TYPE: DNA
```

-continued

<213> ORGANISM: Artificial
<220> FEATURE:
<223> OTHER INFORMATION: primer

<400> SEQUENCE: 1
gcacagaatc cttggtgaac ag 22

<210> SEQ ID NO 2
<211> LENGTH: 22
<212> TYPE: DNA
<213> ORGANISM: Artificial
<220> FEATURE:
<223> OTHER INFORMATION: primer

<400> SEQUENCE: 2
atggaaggtg aatgtttcag ca 22

<210> SEQ ID NO 3
<211> LENGTH: 21
<212> TYPE: DNA
<213> ORGANISM: Artificial
<220> FEATURE:
<223> OTHER INFORMATION: primer

<400> SEQUENCE: 3
ctgtgctact cctcaccatc t 21

<210> SEQ ID NO 4
<211> LENGTH: 21
<212> TYPE: DNA
<213> ORGANISM: Artificial
<220> FEATURE:
<223> OTHER INFORMATION: primer

<400> SEQUENCE: 4
ctctccacac atggctcctt t 21

<210> SEQ ID NO 5
<211> LENGTH: 21
<212> TYPE: DNA
<213> ORGANISM: Artificial
<220> FEATURE:
<223> OTHER INFORMATION: primer

<400> SEQUENCE: 5
tgctccactc actttaccgt c 21

<210> SEQ ID NO 6
<211> LENGTH: 21
<212> TYPE: DNA
<213> ORGANISM: Artificial
<220> FEATURE:
<223> OTHER INFORMATION: primer

<400> SEQUENCE: 6
tagcgtccag tgtgtactga c 21

<210> SEQ ID NO 7
<211> LENGTH: 21
<212> TYPE: DNA
<213> ORGANISM: Artificial
<220> FEATURE:
<223> OTHER INFORMATION: primer

<400> SEQUENCE: 7
tccagtgcct tggataagct g 21

<210> SEQ ID NO 8
<211> LENGTH: 19
<212> TYPE: DNA
<213> ORGANISM: Artificial
<220> FEATURE:
<223> OTHER INFORMATION: primer

<400> SEQUENCE: 8
ggctgatgag ttcccgagc 19

<210> SEQ ID NO 9
<211> LENGTH: 21
<212> TYPE: DNA
<213> ORGANISM: Artificial
<220> FEATURE:
<223> OTHER INFORMATION: primer

<400> SEQUENCE: 9
gtggaaactt gcatggacaa c 21

<210> SEQ ID NO 10
<211> LENGTH: 21
<212> TYPE: DNA
<213> ORGANISM: Artificial
<220> FEATURE:
<223> OTHER INFORMATION: primer

<400> SEQUENCE: 10
aatcctggca catcgggaat c 21

<210> SEQ ID NO 11
<211> LENGTH: 18
<212> TYPE: DNA
<213> ORGANISM: Artificial
<220> FEATURE:
<223> OTHER INFORMATION: primer

<400> SEQUENCE: 11
cagccaagca ctgtcagg 18

<210> SEQ ID NO 12
<211> LENGTH: 20
<212> TYPE: DNA
<213> ORGANISM: Artificial
<220> FEATURE:
<223> OTHER INFORMATION: primer

<400> SEQUENCE: 12
ccagagccat tgtcacacac 20

<210> SEQ ID NO 13
<211> LENGTH: 20
<212> TYPE: DNA
<213> ORGANISM: Artificial
<220> FEATURE:
<223> OTHER INFORMATION: primer

<400> SEQUENCE: 13
ctatgaggtc cttgggggag 20

<210> SEQ ID NO 14
<211> LENGTH: 20
<212> TYPE: DNA
<213> ORGANISM: Artificial
<220> FEATURE:

<223> OTHER INFORMATION: primer

<400> SEQUENCE: 14
ctcgctcagt catccagtca 20

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
ctgagatcct gagcctttgg 20

<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
aagccattgg tgtttccttg 20

<210> SEQ ID NO 17
<211> LENGTH: 18
<212> TYPE: DNA
<213> ORGANISM: Artificial
<220> FEATURE:
<223> OTHER INFORMATION: primer

<400> SEQUENCE: 17
gtcccacctg cccctttg 18

<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
agtggcgcct ctgagtcttg 20

<210> SEQ ID NO 19
<211> LENGTH: 22
<212> TYPE: DNA
<213> ORGANISM: Artificial
<220> FEATURE:
<223> OTHER INFORMATION: primer

<400> SEQUENCE: 19
acaagaacag caacgagtac cg 22

<210> SEQ ID NO 20
<211> LENGTH: 21
<212> TYPE: DNA
<213> ORGANISM: Artificial
<220> FEATURE:
<223> OTHER INFORMATION: primer

<400> SEQUENCE: 20
cattgtcact ggtcagctcc a 21

<210> SEQ ID NO 21
<211> LENGTH: 20
<212> TYPE: DNA
<213> ORGANISM: Artificial
<220> FEATURE:
<223> OTHER INFORMATION: primer

<400> SEQUENCE: 21
cacacgtctc ggtcatggta 20

<210> SEQ ID NO 22
<211> LENGTH: 20
<212> TYPE: DNA
<213> ORGANISM: Artificial
<220> FEATURE:
<223> OTHER INFORMATION: primer

<400> SEQUENCE: 22
aagaggaagg ccaagtcgag 20

<210> SEQ ID NO 23
<211> LENGTH: 22
<212> TYPE: DNA
<213> ORGANISM: Artificial
<220> FEATURE:
<223> OTHER INFORMATION: primer

<400> SEQUENCE: 23
aatgaggtgg gcttaaagca ag 22

<210> SEQ ID NO 24
<211> LENGTH: 21
<212> TYPE: DNA
<213> ORGANISM: Artificial
<220> FEATURE:
<223> OTHER INFORMATION: primer

<400> SEQUENCE: 24
agttccactc cacagttcag a 21

<210> SEQ ID NO 25
<211> LENGTH: 20
<212> TYPE: DNA
<213> ORGANISM: Artificial
<220> FEATURE:
<223> OTHER INFORMATION: primer

<400> SEQUENCE: 25
gccctgcctc tcctatcatc 20

<210> SEQ ID NO 26
<211> LENGTH: 20
<212> TYPE: DNA
<213> ORGANISM: Artificial
<220> FEATURE:
<223> OTHER INFORMATION: primer

<400> SEQUENCE: 26
acggtgagat tgcatcgtgg 20

<210> SEQ ID NO 27
<211> LENGTH: 20
<212> TYPE: DNA
<213> ORGANISM: Artificial
<220> FEATURE:
<223> OTHER INFORMATION: primer

<400> SEQUENCE: 27
cttcgtaaac cagtggcagg 20

<210> SEQ ID NO 28
<211> LENGTH: 20
<212> TYPE: DNA
<213> ORGANISM: Artificial
<220> FEATURE:
<223> OTHER INFORMATION: primer

<400> SEQUENCE: 28
agggcttgtt aatggcagtg 20

<210> SEQ ID NO 29
<211> LENGTH: 20
<212> TYPE: DNA
<213> ORGANISM: Artificial
<220> FEATURE:
<223> OTHER INFORMATION: primer

<400> SEQUENCE: 29
gagttcctgt cactgttgcg 20

<210> SEQ ID NO 30
<211> LENGTH: 20
<212> TYPE: DNA
<213> ORGANISM: Artificial
<220> FEATURE:
<223> OTHER INFORMATION: primer

<400> SEQUENCE: 30
gtcctggcag gtgtttcatc 20

<210> SEQ ID NO 31
<211> LENGTH: 21
<212> TYPE: DNA
<213> ORGANISM: Artificial
<220> FEATURE:
<223> OTHER INFORMATION: primer

<400> SEQUENCE: 31
ccggggatat ggtgtgatct t 21

<210> SEQ ID NO 32
<211> LENGTH: 21
<212> TYPE: DNA
<213> ORGANISM: Artificial
<220> FEATURE:
<223> OTHER INFORMATION: primer

<400> SEQUENCE: 32
ccgaagtccc tcatagtggt c 21

<210> SEQ ID NO 33
<211> LENGTH: 21
<212> TYPE: DNA
<213> ORGANISM: Artificial
<220> FEATURE:
<223> OTHER INFORMATION: primer

<400> SEQUENCE: 33
gaagaggagc attgaggacc g 21

<210> SEQ ID NO 34
<211> LENGTH: 20

<212> TYPE: DNA
<213> ORGANISM: Artificial
<220> FEATURE:
<223> OTHER INFORMATION: primer

<400> SEQUENCE: 34
gcccaggatg aaagtgggat 20

<210> SEQ ID NO 35
<211> LENGTH: 20
<212> TYPE: DNA
<213> ORGANISM: Artificial
<220> FEATURE:
<223> OTHER INFORMATION: primer

<400> SEQUENCE: 35
ctcgggactt tatggattgc 20

<210> SEQ ID NO 36
<211> LENGTH: 20
<212> TYPE: DNA
<213> ORGANISM: Artificial
<220> FEATURE:
<223> OTHER INFORMATION: primer

<400> SEQUENCE: 36
cagtgccaac caagttttca 20

<210> SEQ ID NO 37
<211> LENGTH: 21
<212> TYPE: DNA
<213> ORGANISM: Artificial
<220> FEATURE:
<223> OTHER INFORMATION: primer

<400> SEQUENCE: 37
gccacatgcc ctacacagat g 21

<210> SEQ ID NO 38
<211> LENGTH: 23
<212> TYPE: DNA
<213> ORGANISM: Artificial
<220> FEATURE:
<223> OTHER INFORMATION: primer

<400> SEQUENCE: 38
taatgtcaca ggtcactgca tgg 23

<210> SEQ ID NO 39
<211> LENGTH: 21
<212> TYPE: DNA
<213> ORGANISM: Artificial
<220> FEATURE:
<223> OTHER INFORMATION: primer

<400> SEQUENCE: 39
gtgtccaaca ggagatcgac g 21

<210> SEQ ID NO 40
<211> LENGTH: 21
<212> TYPE: DNA
<213> ORGANISM: Artificial
<220> FEATURE:
<223> OTHER INFORMATION: primer

<400> SEQUENCE: 40
cacctcatga atcacggcag t 21

<210> SEQ ID NO 41
<211> LENGTH: 20
<212> TYPE: DNA
<213> ORGANISM: Artificial
<220> FEATURE:
<223> OTHER INFORMATION: primer

<400> SEQUENCE: 41
agcctggtgc tcctctatct 20

<210> SEQ ID NO 42
<211> LENGTH: 20
<212> TYPE: DNA
<213> ORGANISM: Artificial
<220> FEATURE:
<223> OTHER INFORMATION: primer

<400> SEQUENCE: 42
cccttatggt aggacaaaat 20

<210> SEQ ID NO 43
<211> LENGTH: 20
<212> TYPE: DNA
<213> ORGANISM: Artificial
<220> FEATURE:
<223> OTHER INFORMATION: primer

<400> SEQUENCE: 43
cactggtcgc catctttgta 20

<210> SEQ ID NO 44
<211> LENGTH: 20
<212> TYPE: DNA
<213> ORGANISM: Artificial
<220> FEATURE:
<223> OTHER INFORMATION: primer

<400> SEQUENCE: 44
agtgcatgga agagacctgc 20

<210> SEQ ID NO 45
<211> LENGTH: 20
<212> TYPE: DNA
<213> ORGANISM: Artificial
<220> FEATURE:
<223> OTHER INFORMATION: primer

<400> SEQUENCE: 45
ggctcttcat gacaaagggt 20

<210> SEQ ID NO 46
<211> LENGTH: 20
<212> TYPE: DNA
<213> ORGANISM: Artificial
<220> FEATURE:
<223> OTHER INFORMATION: primer

<400> SEQUENCE: 46
atccgcatca ctgacaacat 20

<210> SEQ ID NO 47
<211> LENGTH: 20
<212> TYPE: DNA
<213> ORGANISM: Artificial

<220> FEATURE:
<223> OTHER INFORMATION: primer

<400> SEQUENCE: 47
gtggctccag gatgttagga 20

<210> SEQ ID NO 48
<211> LENGTH: 20
<212> TYPE: DNA
<213> ORGANISM: Artificial
<220> FEATURE:
<223> OTHER INFORMATION: primer

<400> SEQUENCE: 48
aggcctgagt tcatgttgct 20

<210> SEQ ID NO 49
<211> LENGTH: 20
<212> TYPE: DNA
<213> ORGANISM: Artificial
<220> FEATURE:
<223> OTHER INFORMATION: primer

<400> SEQUENCE: 49
gagatgccga aggggtatcg 20

<210> SEQ ID NO 50
<211> LENGTH: 21
<212> TYPE: DNA
<213> ORGANISM: Artificial
<220> FEATURE:
<223> OTHER INFORMATION: primer

<400> SEQUENCE: 50
tgattctccc ggtagtaagg g 21

<210> SEQ ID NO 51
<211> LENGTH: 20
<212> TYPE: DNA
<213> ORGANISM: Artificial
<220> FEATURE:
<223> OTHER INFORMATION: primer

<400> SEQUENCE: 51
ccatcctcaa agagctggag 20

<210> SEQ ID NO 52
<211> LENGTH: 20
<212> TYPE: DNA
<213> ORGANISM: Artificial
<220> FEATURE:
<223> OTHER INFORMATION: primer

<400> SEQUENCE: 52
gtgctgctgc aggtaggact 20

<210> SEQ ID NO 53
<211> LENGTH: 20
<212> TYPE: DNA
<213> ORGANISM: Artificial
<220> FEATURE:
<223> OTHER INFORMATION: primer

<400> SEQUENCE: 53
ccaaaaccct cgtcgacatg 20

<210> SEQ ID NO 54
<211> LENGTH: 23
<212> TYPE: DNA
<213> ORGANISM: Artificial
<220> FEATURE:
<223> OTHER INFORMATION: primer

<400> SEQUENCE: 54
ttctcaaatt ccagggtggt gta 23

<210> SEQ ID NO 55
<211> LENGTH: 19
<212> TYPE: DNA
<213> ORGANISM: Artificial
<220> FEATURE:
<223> OTHER INFORMATION: primer

<400> SEQUENCE: 55
tgtggaagtg gctgcagga 19

<210> SEQ ID NO 56
<211> LENGTH: 20
<212> TYPE: DNA
<213> ORGANISM: Artificial
<220> FEATURE:
<223> OTHER INFORMATION: primer

<400> SEQUENCE: 56
tgtgaagacc aacctgggct 20

<210> SEQ ID NO 57
<211> LENGTH: 21
<212> TYPE: DNA
<213> ORGANISM: Artificial
<220> FEATURE:
<223> OTHER INFORMATION: primer

<400> SEQUENCE: 57
cgaacactct tcgccatctt c 21

<210> SEQ ID NO 58
<211> LENGTH: 21
<212> TYPE: DNA
<213> ORGANISM: Artificial
<220> FEATURE:
<223> OTHER INFORMATION: primer

<400> SEQUENCE: 58
gttgctgacg gttgtgagct c 21

<210> SEQ ID NO 59
<211> LENGTH: 18
<212> TYPE: DNA
<213> ORGANISM: Artificial
<220> FEATURE:
<223> OTHER INFORMATION: primer

<400> SEQUENCE: 59
gtgagaagcc cttcgcct 18

<210> SEQ ID NO 60
<211> LENGTH: 20
<212> TYPE: DNA
<213> ORGANISM: Artificial
<220> FEATURE:
<223> OTHER INFORMATION: primer

<400> SEQUENCE: 60
cacacaggac actggtacgg 20

<210> SEQ ID NO 61
<211> LENGTH: 21
<212> TYPE: DNA
<213> ORGANISM: Artificial
<220> FEATURE:
<223> OTHER INFORMATION: primer

<400> SEQUENCE: 61
gggatctctt ccacactgga t 21

<210> SEQ ID NO 62
<211> LENGTH: 20
<212> TYPE: DNA
<213> ORGANISM: Artificial
<220> FEATURE:
<223> OTHER INFORMATION: primer

<400> SEQUENCE: 62
catacaggcc ctgaagagga 20

<210> SEQ ID NO 63
<211> LENGTH: 20
<212> TYPE: DNA
<213> ORGANISM: Artificial
<220> FEATURE:
<223> OTHER INFORMATION: primer

<400> SEQUENCE: 63
gttggagaag ctgccatcac 20

<210> SEQ ID NO 64
<211> LENGTH: 20
<212> TYPE: DNA
<213> ORGANISM: Artificial
<220> FEATURE:
<223> OTHER INFORMATION: primer

<400> SEQUENCE: 64
cgggaccttc agacactttt 20

<210> SEQ ID NO 65
<211> LENGTH: 20
<212> TYPE: DNA
<213> ORGANISM: Artificial
<220> FEATURE:
<223> OTHER INFORMATION: primer

<400> SEQUENCE: 65
agggaccatc ctcttcaacc 20

<210> SEQ ID NO 66
<211> LENGTH: 20
<212> TYPE: DNA
<213> ORGANISM: Artificial
<220> FEATURE:
<223> OTHER INFORMATION: primer

<400> SEQUENCE: 66
acttcacaca gcacccagtg 20

<210> SEQ ID NO 67

<211> LENGTH: 19
<212> TYPE: DNA
<213> ORGANISM: Artificial
<220> FEATURE:
<223> OTHER INFORMATION: primer

<400> SEQUENCE: 67
agggggacat gaacctcag 19

<210> SEQ ID NO 68
<211> LENGTH: 20
<212> TYPE: DNA
<213> ORGANISM: Artificial
<220> FEATURE:
<223> OTHER INFORMATION: primer

<400> SEQUENCE: 68
aggtccccat catagatccc 20

<210> SEQ ID NO 69
<211> LENGTH: 22
<212> TYPE: DNA
<213> ORGANISM: Artificial
<220> FEATURE:
<223> OTHER INFORMATION: primer

<400> SEQUENCE: 69
ttcaatcatg gaccaaaatc aa 22

<210> SEQ ID NO 70
<211> LENGTH: 20
<212> TYPE: DNA
<213> ORGANISM: Artificial
<220> FEATURE:
<223> OTHER INFORMATION: primer

<400> SEQUENCE: 70
tgagtgacag agctgccaag 20

<210> SEQ ID NO 71
<211> LENGTH: 20
<212> TYPE: DNA
<213> ORGANISM: Artificial
<220> FEATURE:
<223> OTHER INFORMATION: primer

<400> SEQUENCE: 71
acagggctct gaacatgcac 20

<210> SEQ ID NO 72
<211> LENGTH: 20
<212> TYPE: DNA
<213> ORGANISM: Artificial
<220> FEATURE:
<223> OTHER INFORMATION: primer

<400> SEQUENCE: 72
ggcattgaaa aactcccgta 20

<210> SEQ ID NO 73
<211> LENGTH: 19
<212> TYPE: DNA
<213> ORGANISM: Artificial
<220> FEATURE:
<223> OTHER INFORMATION: primer

<400> SEQUENCE: 73
gagtgtggat tcgcactcc 19

<210> SEQ ID NO 74
<211> LENGTH: 19
<212> TYPE: DNA
<213> ORGANISM: Artificial
<220> FEATURE:
<223> OTHER INFORMATION: primer

<400> SEQUENCE: 74
gaggcgaggg agttcttct 19

<210> SEQ ID NO 75
<211> LENGTH: 18
<212> TYPE: DNA
<213> ORGANISM: Artificial
<220> FEATURE:
<223> OTHER INFORMATION: primer

<400> SEQUENCE: 75
tcaccagcac catgcaac 18

<210> SEQ ID NO 76
<211> LENGTH: 18
<212> TYPE: DNA
<213> ORGANISM: Artificial
<220> FEATURE:
<223> OTHER INFORMATION: primer

<400> SEQUENCE: 76
aagccaccca aggcacag 18

<210> SEQ ID NO 77
<211> LENGTH: 23
<212> TYPE: DNA
<213> ORGANISM: Artificial
<220> FEATURE:
<223> OTHER INFORMATION: primer

<400> SEQUENCE: 77
gaattccaca acctttcacc aaa 23

<210> SEQ ID NO 78
<211> LENGTH: 27
<212> TYPE: DNA
<213> ORGANISM: Artificial
<220> FEATURE:
<223> OTHER INFORMATION: primer

<400> SEQUENCE: 78
gaattccact gcatggcctg aggatga 27

<210> SEQ ID NO 79
<211> LENGTH: 23
<212> TYPE: DNA
<213> ORGANISM: Artificial
<220> FEATURE:
<223> OTHER INFORMATION: primer

<400> SEQUENCE: 79
cccaggtagc tagagtcatt agt 23

<210> SEQ ID NO 80
<211> LENGTH: 26
<212> TYPE: DNA

-continued

```
<213> ORGANISM: Artificial
<220> FEATURE:
<223> OTHER INFORMATION: primer

<400> SEQUENCE: 80

aaggtcggtc gttgacattg cagaga                                            26


<210> SEQ ID NO 81
<211> LENGTH: 22
<212> TYPE: DNA
<213> ORGANISM: Artificial
<220> FEATURE:
<223> OTHER INFORMATION: primer

<400> SEQUENCE: 81

ggtatcgtgg aaggactcat ga                                                22


<210> SEQ ID NO 82
<211> LENGTH: 23
<212> TYPE: DNA
<213> ORGANISM: Artificial
<220> FEATURE:
<223> OTHER INFORMATION: primer

<400> SEQUENCE: 82

atgccagtgg cttcccgttc agc                                               23


<210> SEQ ID NO 83
<211> LENGTH: 27
<212> TYPE: DNA
<213> ORGANISM: Artificial
<220> FEATURE:
<223> OTHER INFORMATION: primer

<400> SEQUENCE: 83

ccctgtgagg aactactgtc ttcacgc                                           27


<210> SEQ ID NO 84
<211> LENGTH: 27
<212> TYPE: DNA
<213> ORGANISM: Artificial
<220> FEATURE:
<223> OTHER INFORMATION: primer

<400> SEQUENCE: 84

gctcatggtg cacggtctac gagacct                                           27
```